US008778974B2

(12) United States Patent
MacDonald et al.

(10) Patent No.: US 8,778,974 B2
(45) Date of Patent: Jul. 15, 2014

(54) TRISUBSTITUTED 1,2,4 TRIAZOLES

(75) Inventors: Gregor James MacDonald, Zoersel (BE); Johannes Wilhelmus John F. Thuring, Antwerpen (BE); Pauline Carol Stanislawski, Antwerpen (BE); Wei Zhuang, Antwepen (BE); Yves Emiel Maria Van Roosbroeck, Heist-op-den-Berg (BE); Frans Alfons Maria Van Den Keybus, Essen (BE)

(73) Assignee: Janssen Pharmaceutica NV, Beerse (BE)

( * ) Notice: Subject to any disclaimer, the term of this patent is extended or adjusted under 35 U.S.C. 154(b) by 350 days.

(21) Appl. No.: 12/866,054

(22) PCT Filed: Mar. 18, 2009

(86) PCT No.: PCT/EP2009/053186
§ 371 (c)(1),
(2), (4) Date: Aug. 4, 2010

(87) PCT Pub. No.: WO2009/115547
PCT Pub. Date: Sep. 24, 2009

(65) Prior Publication Data
US 2010/0324053 A1 Dec. 23, 2010

(30) Foreign Application Priority Data

Mar. 19, 2008 (EP) .................................. 08152987

(51) Int. Cl.
*A61K 31/4439* (2006.01)
*C07D 401/04* (2006.01)
(52) U.S. Cl.
USPC ........................................ 514/340; 546/272.4
(58) Field of Classification Search
USPC ........................................ 546/272.4; 514/340
See application file for complete search history.

(56) References Cited

U.S. PATENT DOCUMENTS

| 3,933,838 | A | 1/1976 | Manghisi et al. |
|---|---|---|---|
| 6,187,797 | B1 | 2/2001 | Pruitt et al. |
| 6,245,916 | B1 | 6/2001 | Fauchere et al. |
| 6,569,874 | B1 | 5/2003 | Pruitt et al. |
| 8,143,419 | B2 | 3/2012 | Thuring et al. |
| 2004/0073029 | A1 | 4/2004 | Pruitt et al. |
| 2004/0254236 | A1 | 12/2004 | Dong et al. |
| 2005/0004134 | A1 | 1/2005 | Tsutsumi et al. |
| 2006/0063756 | A1 | 3/2006 | Salituro et al. |
| 2010/0216846 | A1 | 8/2010 | Thuring et al. |
| 2010/0240707 | A1 | 9/2010 | Thuring et al. |
| 2011/0065683 | A1 | 3/2011 | Thuring et al. |
| 2011/0269748 | A1 | 11/2011 | Thuring et al. |
| 2012/0172354 | A1 | 7/2012 | Macdonald et al. |
| 2012/0238561 | A1 | 9/2012 | Macdonald et al. |

FOREIGN PATENT DOCUMENTS

| EP | 267986 A | 5/1988 |
|---|---|---|
| EP | 275312 A | 7/1988 |
| EP | 248523 B1 | 10/1991 |
| EP | 1205478 A | 5/2002 |
| EP | 1044970 | 1/2003 |
| EP | 1070708 A1 | 1/2004 |
| WO | WO 96/03392 A1 | 2/1996 |
| WO | WO 97/05131 A | 2/1997 |
| WO | WO 98/15543 A | 4/1998 |
| WO | WO 98/28282 A2 | 7/1998 |
| WO | WO 99/21555 A2 | 5/1999 |
| WO | WO 01/44207 A2 | 6/2001 |
| WO | WO 01/64674 A | 9/2001 |
| WO | WO 01/74793 A | 10/2001 |
| WO | WO 02/24200 A | 3/2002 |
| WO | WO 02/42298 A | 5/2002 |
| WO | WO 02/057240 | 7/2002 |
| WO | WO 03/015773 | 2/2003 |
| WO | WO 03/062215 | 7/2003 |
| WO | WO 03/094831 | 11/2003 |
| WO | WO 2004/096225 | 11/2004 |
| WO | WO 2004/110350 | 12/2004 |
| WO | WO 2005/012263 | 2/2005 |
| WO | WO 2005/051917 | 6/2005 |
| WO | WO 2006/064375 | 6/2005 |
| WO | WO 2005/070926 | 8/2005 |
| WO | WO 2006/047256 | 5/2006 |
| WO | WO 2007/031440 A2 | 3/2007 |
| WO | WO 2007/118903 A1 | 10/2007 |
| WO | WO 2009/127678 | 10/2009 |
| WO | WO 2009/135944 | 11/2009 |
| WO | WO 2012/113850 | 8/2012 |

OTHER PUBLICATIONS

Yu et al., "Physical characterization of, etc.," PSTT, vol. 1(3), 118-127 (1998).*
Guillory (in Brittain ed.), "Polymorphism, etc.," NY: Marcel Dekker, Inc., 1999, 1-2, 125-181, 183-226.*
Vippagunta et a;. "Crystalline Solid" Advanced Drug Delivery Reviews 48 (2001) 3-26.*
Chen, C., et al., "1-Alkyl-3-Amino-5-Aryl-1H-[1,2,4]triazoles: Novel Synthesis Via Cyclization of N-Acyl-S-Methylisothioureas with Alkyhydrazines and Their Potent Corticotropin-Releasing Factor-1 ($CRF_1$) Receptor Antagonist Activities", Bioorganic & Medicinal Chemistry Letters 11 (2001) pp. 3165-3168.
Makara, G., et al. "Solid-Phase Synthesis of 3-Alkylamino-1,2,4-Triazoles", Organic Letters, vol. 4, No. 10 (2002) pp. 1751-1754.

(Continued)

*Primary Examiner* — Patricia L Morris
(74) *Attorney, Agent, or Firm* — Peter Herridge

(57) ABSTRACT

The present invention relates to 1-aryl-3-aniline-5-alkyl-1,2,4-triazole derivatives and analogues or pharmaceutically acceptable salts thereof, processes for preparing them, pharmaceutical compositions containing them and their use in therapy, according to Formula (I).

The invention particularly relates to potent positive allosteric modulators of nicotinic acetylcholine receptors, such positive allosteric modulator having the capability to increase the efficacy of nicotinic receptor agonists.

4 Claims, No Drawings

(56) References Cited

OTHER PUBLICATIONS

Banerjee, Carolin et al., "Cellular Expression of α7 Nicotinic Acetylcholine Receptor Protein in the emporal Cortex in Alzheimer's and Parkinson's Disease—A Stereological Approach", Neurobiology of Disease, (2000), pp. 666-672, vol. 7.

Bickford, Paula C. et al., "Restoration of sensory gating of auditory evoked response by nicotine in fimbria-fornix lesioned rats", Brain Research, (1995), pp. 235-240, vol. 705.

Brown, D.J. et al., "The Chemistry of heterocyclic compounds: Fused Pyrimidines", Book—The Chemistry of Heterocyclic compounds, (1971), pp. 261-304, Chapter IV.

Burghaus, Lothar et al., "Quantitative assessment of nicotinic acetylcholine receptor proteins in the cerebral cortex of Alzheimer patients", Molecular Brain Research, (2000), pp. 385-388, vol. 76.

Dalack, Gregory W. et al., "Nicotine Dependence in Schizophrenia: Clinical Phenomena and Laboratory Findings", Am J Psychiatry, Nov. 1998, pp. 1490-1500, vol. 155:11.

Dani, John A. et al., "Variations in desensitization of nicotinic acetylcholine receptors from hippocampus and midbrain dopamine areas", European Journal of Pharmacology, (2000), pp. 1-38, vol. 393.

Freedman, Robert et al., "Evidence in Postmortem Brain Tissue for Decreased Numbers of Hippocampal Nicotinic Receptors in Schizophrenia", Biol Psychiatry, (1995), pp. 22-33, vol. 38.

Freedman, Robert et al., "Linkage of a neurophysiological deficit in schizophrenia to a chromosome 15 locus", Proc. Natl. Acad. Sci. USA, Jan. 1997, pp. 587-592, vol. 94.

Gol'din et. al.. Hcaplus Abstract 1974:437516, "Synthesis of triazolones and C-aminotriazoles by the thermal condensation of carbamidoamidrazones", 1974.

Griffith, Jay M. et al., "Nicotinic Receptor Desensitization and Sensory Gating Deficits in Schizophrenia", Biol Psychiatry, 1998, pp. 98-106, vol. 44.

Guan, Zhi-Zhong et al., "Decreased protein level of nicotinic receptor α7 subunit in the frontal cortex from schizophrenic brain", NeuroReport, Jun. 3, 1999, pp. 1779-1782, vol. 10 No. 8.

Hamill, O. P. et al., "Improved Patch-Clamp Techniques for High-Resolution Current Recording from Cells and Cell-Free Membrane Patches", Pflugers Arch, (1981) pp. 85-100, vol. 391.

Intelihealth, "Alzheimer's disease," online, accessed Jun. 30, 2008, http://www.intelihealth.com/IH/intlhIWSIHWOOO/8303/9117/195703.html?d=dmtHealthAZ.

Intelihealth, "Dementia," online, accessed Sep. 22, 2009, http://www.intelihealth.com/IH/ihtIHIWSIHWOOO/24479/11184.html.

Intelihealth, "Parkinson's disease," online, accessed Sep. 22, 2009, http://www.intelihealth.com/IH/ihtIH?d=dmtHealthAZ&c=201957.

Intelihealth, "Schizophrenia" online, accessed Oct. 4, 2011, http://www.intelihealth.com/IH/ihtIHIWSIHWOOO/8271 /8694/1 8801 O. html?d=dmtHealthAZ#prevent.

Leonard, Sherry et al., "Association of Promoter Variants in the α7 Nicotinic Acetylcholine Receptor Subunit Gene With an Inhibitory Deficit Found in Schizophrenia", Arch Gen Psychiatry, Dec. 2002, pp. 1085-1096, vol. 59.

Lin et. al., "Recent developments in neuronal nicotinic acetycholine receptor modulators", 1998, 8 (8), pp. 991-1015.

Marutle, Amelia et al., "Laminar distribution of nicotinic receptor subtypes in cortical regions in schizophrenia", Journal of Chemical Neuroanatomy, (2001), pp. 115-126, vol. 22.

Muccioli, et al., "Latest Advances in Cannadinoid Receptor Antagonists and Inverse Agonists", Expert Opinion on Therapeutic Patents, vol. 16, No. 10, pp. 1405-1423, (2006).

Nagamatsu, Tomohisa et al., "General syntheses of—alkyltoxoflavin and 8-alkylfervenulin derivatives of biological significance by the regioselective alkylation of reumycin derivatives and the rates of transalkylation from 1-alkyltoxoflavins into nucleophiles", J. Chem. Soc., Perkin Trans., 2001, pp. 130-137.

Nagamatsu, Tomohisa et al., "Syntheses of 3-Substituted 1-Methyl-6-phenylpyrimido[5,4-e]-1,2,4-triazine-5,7(1H,6H)-diones (6-Phenyl Analogs of Toxoflavin) and Their 4-Oxides, and Evaluation of Antimicrobial Activity of Toxoflavins and Their Analogs", Chem. Pharm. Bull., (1993) pp. 362-368, vol. 41(2).

Ray, M.A. et al., "Neuronal nicotinic acetylcholine receptor subunits in autism: An immunohistochemical investigation in the thalamus", Neurobiology of Disease, (2005), pp. 366-377, vol. 19.

Ridley, Diana L. et al., "Differential effects of chronic drug treatment on α3* and α7 nicotinic receptor binding sites, in hippocampal neurons and SH-SY5Y cells", British Journal of Pharmacology, (2001), pp. 1286-1295, vol. 133.

Silverman, R. "The Organic Chemistry of Drug Design and Drug Action," 2004, Elsevier, pp. 29-32.

Stetter, Hermann et al., The Catalyzed Nucleophilic Addition of Aldehydes to Electrophilic Double Bonds*, Organic Reactions, (1991), pp. 407-496, vol. 40, Chapter 4.

Virginio, Caterina et al., "Pharmacological properties of rat α7 nicotinic receptors expressed in native and recombinant cell systems", European Journal of Pharmacology, (2002), pp. 153-161, vol. 445.

West, Anthony R., Solid State Chemistry and its Applications, Wiley, New York, 1988, pp. 358 & 365.

Office Action mailed Aug. 12, 2011 in U.S. Appl. No. 12/063,689.
Office Action mailed Dec. 21, 2011 in U.S. Appl. No. 12/063,689.
Final Office Action mailed Apr. 5, 2012 in U.S. Appl. No. 12/063,689.
Notice of Allowance mailed Jul. 23, 2012 in U.S. Appl. No. 12/063,689.
Office Action mailed Oct. 13, 2011 in U.S. Appl. No. 12/738,763.
Office Action mailed Dec. 14, 2011 in U.S. Appl. No. 12/738,763.
Final Office Action mailed Apr. 19, 2012 in U.S. Appl. No. 12/738,763.
Notice of Allowance mailed Aug. 9, 2012 in U.S. Appl. No. 12/738,763.
Notice of Allowance mailed Jan. 17, 2013 in U.S. Appl. No. 12/738,763.
Office Action mailed Dec. 2, 2011 in U.S. Appl. No. 12/738,725.
Notice of Allowance mailed Apr. 4, 2012 in U.S. Appl. No. 12/738,725.
Notice of Allowance mailed Jul. 19, 2012 in U.S. Appl. No. 12/738,725.
Office Action mailed Mar. 15, 2012 in U.S. Appl. No. 12/991,119.
Office Action mailed Jun. 22, 2012 in U.S. Appl. No. 12/991,119.
Notice of Allowance mailed Jan. 23, 2013 in U.S. Appl. No. 12/991,119.

* cited by examiner

TRISUBSTITUTED 1,2,4 TRIAZOLES

CROSS REFERENCE TO RELATED APPLICATIONS

This application is a national stage application of Patent Application No. PCT/EP2009/053186, filed Mar. 18, 2009, which in turn claims the benefit of EPO Patent Application No. 08152987.7 filed Mar. 19, 2008. The complete disclosures of the aforementioned related patent applications are hereby incorporated herein by reference for all purposes.

The present invention relates to 1-aryl-3-aniline-5-alkyl-1, 2,4-triazole derivatives and pharmaceutically acceptable salts thereof, processes for preparing them, pharmaceutical compositions containing them and their use in therapy. The invention particularly relates to potent positive allosteric modulators of nicotinic acetylcholine receptors, such positive allosteric modulators having the capability to increase the efficacy of nicotinic receptor agonists.

BACKGROUND PRIOR ART

EP 1044970 describes 3-alkylamino-1,2,4-triazoles as neuropeptide Y receptor ligands.

The paper by Makara G. M., et al. (Organic Letters (2002) Vol. 4 (10); 1751-1754) describes the solid-phase synthesis of 3-alkylamino-1,2,4-triazoles and exemplifies the unsuccessful synthesis of N-(4-methoxyphenyl)-1-methyl-5-(4-methylphenyl)-1H-1,2,4-triazol-3-amine [CAS No: 433710-55-5] and is silent about potential therapeutic applications of this compound, in particular about its use as a positive allosteric modulator of the α7 nicotinic acetylcholine receptor.

Chen Chen et al., in Bioorganic & Medicinal Chemistry Letters 11 (2001) 3165-3168 describes the synthesis of 1-alkyl-3-amino-5-aryl-1H-[1,2,4]triazoles, in particular N-(2-methoxyphenyl)-1-methyl-5-(2,4-dichlorophenyl)-1H-1,2,4-triazol-3-amine, and their use as corticotropin-releasing factor-1 (CRF1) antagonist.

WO-2001/44207 discloses similar compounds having affinity for CRF receptors.

WO-2007/118903 discloses 3-aniline-5-aryl 1,2,4 triazoles as positive modulators of nicotinic acetylcholine receptors useful for treating neurological, degenerative and psychiatric disorders.

BACKGROUND OF THE INVENTION

Cholinergic receptors normally bind the endogenous neurotransmitter acetylcholine (ACh), thereby triggering the opening of ion channels. ACh receptors in the mammalian central nervous system can be divided into muscarinic (mAChR) and nicotinic (nAChR) subtypes based on the agonist activities of muscarine and nicotine, respectively. The nicotinic acetylcholine receptors are ligand-gated ion-channels containing five subunits. Members of the nAChR subunit gene family have been divided into two groups based on their amino acid sequences; one group containing so-called β subunits, and a second group containing α subunits. Three kinds of α subunits, α7, α8 and α9, have been shown to form functional receptors when expressed alone and thus are presumed to form homoligomeric pentameric receptors.

An allosteric transition state model of the nAChR has been developed that involves at least a resting state, an activated state and a "desensitized" closed channel state, a process by which receptors become insensitive to the agonist. Different nAChR ligands can stabilize the conformational state of a receptor to which they preferentially bind. For example, the agonists ACh and (−)-nicotine respectively stabilize the active and desensitized states.

Changes of the activity of nicotinic receptors have been implicated in a number of diseases. Some of these, for example myasthenia gravis and autosomal dominant nocturnal front lobe epilepsy (ADNFLE) are associated with reductions in the activity of nicotinic transmission either because of a decrease in receptor number or increased desensitization.

Reductions in nicotinic receptors have also been hypothesized to mediate cognitive deficits seen in diseases such as Alzheimer's disease and schizophrenia.

The effects of nicotine from tobacco are also mediated by nicotinic receptors and since the effect of nicotine is to stabilize receptors in a desensitized state, an increased activity of nicotinic receptors may reduce the desire to smoke.

Compounds which bind nAChRs have been suggested for the treatment of a range of disorders involving reduced cholinergic function such as learning deficit, cognition deficit, attention deficit or memory loss. Modulation of α7 nicotinic receptor activity is expected to be beneficial in a number of diseases including Alzheimer's disease, Lewy Body Dementia, Attention Deficit Hyperactivity Disorder, anxiety, schizophrenia, mania, manic depression, Parkinson's disease, Huntington's disease, Tourette's syndrome, brain trauma or other neurological, degenerative or psychiatric disorders in which there is loss of cholinergic synapses, including jetlag, nicotine addiction, pain.

However, treatment with nicotinic receptor agonists which act at the same site as ACh is problematic because ACh not only activates, but also blocks receptor activity through processes which include desensitization and uncompetitive blockade. Furthermore, prolonged activation appears to induce a long-lasting inactivation. Therefore, agonists of ACh can be expected to reduce activity as well as enhance it.

At nicotinic receptors in general, and of particular note at the α7-nicotinic receptor, desensitization limits the duration of action of an applied agonist.

DESCRIPTION OF THE INVENTION

We have surprisingly found that certain novel triazole derivatives can increase the efficacy of agonists at nicotinic acetylcholine receptors (nAChR). Compounds having this type of action (hereinafter referred to as "positive allosteric modulators") are likely to be useful for treatment of conditions associated with reductions in nicotinic transmission. In a therapeutic setting such compounds could restore normal interneuronal communication without affecting the temporal profile of activation. In addition, positive allosteric modulators are not expected to produce long-term inactivation of receptors as may occur at prolonged application of agonists.

Positive nAChR modulators of the present invention are useful for treatment or prophylaxis of psychotic disorders, intellectual impairment disorders or diseases, inflammatory diseases or conditions in which modulation of the α7 nicotinic receptor is beneficial.

The present invention concerns 1-(aryl)-3-aniline-5-alkyl 1,2,4-triazole derivatives having positive allosteric modulator properties, in particular increasing the efficacy of agonists at the α7 nicotinic receptor. The invention further relates to methods for their preparation and pharmaceutical compositions comprising them. The invention also relates to the use of these derivatives for the manufacture of a medicament for the treatment or prophylaxis of psychotic disorders, intellectual impairment disorders or diseases, or inflammatory diseases or conditions in which modulation of the α7 nicotinic receptor is beneficial.

The compounds of the present invention differ structurally from the prior art compounds and pharmacologically by their enhanced activity as positive allosteric modulators of the α7 nicotinic acetylcholine receptor.

The present invention relates to a compound according to formula (I)

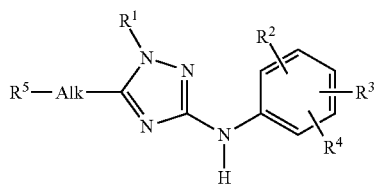

or a stereoisomeric form thereof, wherein
$R^1$ is unsubstituted phenyl; unsubstituted benzodioxan-6-yl; unsubstituted pyridinyl; or phenyl or pyridinyl substituted with 1, 2 or 3 substituents selected from the group consisting of halo, trifluoromethyl, trifluoromethoxy, $C_{1-3}$alkyl, $C_{1-3}$alkyloxy, $C_{1-3}$alkyloxy$C_{1-3}$alkyl, $C_{1-3}$alkylamino, $C_{3-6}$cycloalkyl, $C_{3-6}$cycloalkyloxy, $C_{3-6}$cycloalkylamino, ($C_{3-6}$cycloalkyl)$C_{1-3}$alkyl, ($C_{3-6}$cycloalkyl)$C_{1-3}$alkyloxy, and ($C_{3-6}$cycloalkyl)$C_{1-3}$alkylamino;
$R^2$ is hydrogen, halo, $C_{1-3}$alkyl, $C_{1-3}$alkyloxy or trifluoromethoxy;
$R^3$ is hydrogen, halo, or trifluoromethyl;
$R^4$ is hydrogen, or halo;
$R^2$ and $R^3$ may form a radical —OCF$_2$—O—;
Alk is straight or branched $C_{1-6}$alkanediyl or $C_{2-6}$alkenediyl;
$R^5$ is hydrogen, hydroxy, $C_{1-3}$alkyloxy, halo, $R^6R^7$N—C(=O)— or $R^8$—O—C(=O)—;
$R^6$ is $C_{1-3}$alkyl, $C_{3-6}$cycloalkyl or ($C_{3-6}$cycloalkyl)$C_{1-3}$alkyl;
$R^7$ is hydrogen or $C_{1-3}$alkyl; or
$R^6$ and $R^7$ form pyrrolidinyl or piperidinyl each optionally substituted with hydroxyl;
$R^8$ is hydrogen or $C_{1-4}$alkyl;
or a pharmaceutically acceptable addition salt or a hydrate or a solvate thereof.

The present invention relates in particular to a compound according to formula (I) or a stereoisomeric form thereof, wherein
$R^1$ is unsubstituted phenyl; unsubstituted benzodioxan-6-yl; unsubstituted pyridinyl; or phenyl or pyridinyl substituted with 1, 2 or 3 substituents selected from the group consisting of halo, trifluoromethoxy, $C_{1-3}$alkyl, $C_{1-3}$alkyloxy, $C_{1-3}$alkyloxy$C_{1-3}$alkyl,
$C_{1-3}$alkylamino, $C_{3-6}$cycloalkyl, $C_{3-6}$cycloalkyloxy, $C_{3-6}$cycloalkylamino, ($C_{3-6}$cycloalkyl)$C_{1-3}$alkyl, ($C_{3-6}$cycloalkyl)$C_{1-3}$alkyloxy, and ($C_{3-6}$cycloalkyl)$C_{1-3}$alkylamino;
$R^2$ is halo, $C_{1-3}$alkyl, $C_{1-3}$alkyloxy or trifluoromethoxy;
$R^3$ is hydrogen, halo, or trifluoromethyl;
$R^4$ is hydrogen, or halo;
$R^2$ and $R^3$ may form a radical —OCF$_2$—O—;
Alk is straight or branched $C_{1-6}$alkanediyl or $C_{2-6}$alkenediyl;
$R^5$ is hydrogen, hydroxy, $C_{1-3}$alkyloxy, halo, $R^6R^7$N—C(=O)— or $R^8$—O—C(=O)—;
$R^6$ is $C_{1-3}$alkyl, $C_{3-6}$cycloalkyl or ($C_{3-6}$cycloalkyl)$C_{1-3}$alkyl;
$R^7$ is hydrogen or $C_{1-3}$alkyl; or
$R^6$ and $R^7$ form pyrrolidinyl or piperidinyl each optionally substituted with hydroxyl;
$R^8$ is hydrogen or $C_{1-4}$alkyl;
or a pharmaceutically acceptable addition salt or a hydrate or a solvate thereof.

The present invention relates in particular to a compound according to formula (I) or a stereoisomeric form thereof, wherein
$R^1$ is unsubstituted phenyl; unsubstituted benzodioxan-6-yl; unsubstituted pyridinyl; or phenyl or pyridinyl substituted with 1 or 2 substituents selected from the group consisting of halo, trifluoromethoxy, $C_{1-3}$alkyl, $C_{1-3}$alkyloxy, $C_{1-3}$alkyloxy$C_{1-3}$alkyl and
$C_{1-3}$alkylamino;
$R^2$ is hydrogen, halo, methyl, methoxy or trifluoromethoxy;
$R^3$ is hydrogen, halo, or trifluoromethyl;
$R^4$ is hydrogen, or halo;
$R^2$ and $R^3$ may form a radical —OCF$_2$—O— in the 3,4-position;
Alk is straight or branched $C_{1-6}$alkanediyl or $C_{2-6}$alkenediyl;
$R^5$ is hydrogen, hydroxy, $C_{1-3}$alkyloxy, halo, $R^6R^7$N—C(=O)— or $R^8$—O—C(=O)—;
$R^6$ is $C_{1-3}$alkyl, $C_{3-6}$cycloalkyl or ($C_{3-6}$cycloalkyl)$C_{1-3}$alkyl;
$R^7$ is hydrogen or $C_{1-3}$alkyl; or
$R^6$ and $R^7$ form pyrrolidinyl optionally substituted with hydroxyl;
$R^8$ is hydrogen or $C_{1-4}$alkyl;
or a pharmaceutically acceptable addition salt or a hydrate or a solvate thereof.

The present invention more particularly relates to a compound of Formula (I) or a stereoisomeric form thereof, wherein
$R^1$ is unsubstituted benzodioxan-6-yl; unsubstituted pyridinyl; or pyridinyl substituted with 1 or 2 substituents selected from the group consisting of chloro, methyl, ethyl, methoxymethyl and ethylamino;
$R^2$ is hydrogen, halo, methyl, methoxy or trifluoromethoxy;
$R^3$ is hydrogen, halo, or trifluoromethyl;
$R^4$ is hydrogen, or halo;
$R^2$ and $R^3$ may form a radical —OCF$_2$O— in the 3,4 position;
Alk is straight or branched $C_{1-6}$alkanediyl;
$R^5$ is hydroxyl or $R^6R^7$N—C(=O)—;
$R^6$ is methyl, ethyl, cyclopropyl, cyclobutyl or (cyclopropyl)methyl;
$R^7$ is hydrogen or methyl;
or a pharmaceutically acceptable addition salt or a hydrate or a solvate thereof.

The present invention most particularly relates to a compound of Formula (I) or a stereoisomeric form thereof, wherein
$R^1$ is unsubstituted benzodioxan-6-yl; pyridinyl substituted with 1 methyl or ethylamino group; or pyridinyl substituted with 2 methyl groups;
$R^2$ is hydrogen, fluoro, chloro, bromo, methoxy or trifluoromethoxy;
$R^3$ is hydrogen, fluoro, trifluoromethyl, chloro;
$R^4$ is hydrogen, or fluoro;
$R^2$ and $R^3$ may form a radical —OCF$_2$O— in the 3,4 position;
Alk is straight or branched $C_{1-6}$alkanediyl;
$R^5$ is hydroxyl or $R^6R^7$N—C(=O)—;
$R^6$ is methyl, ethyl, cyclopropyl, cyclobutyl or (cyclopropyl)methyl;
$R^7$ is hydrogen or methyl;
or a pharmaceutically acceptable addition salt or a hydrate or a solvate thereof.

The present invention relates in particular to a compound according to formula (I) or a stereoisomeric form thereof, wherein $R^1$ is unsubstituted phenyl; unsubstituted benzodioxan-6-yl; unsubstituted pyridinyl; or phenyl or pyridinyl substituted with 1 or 2 substituents selected from the group consisting of halo, trifluoromethoxy, $C_{1-3}$alkyl, $C_{1-3}$alkyloxy, $C_{1-3}$alkyloxy$C_{1-3}$alkyl and $C_{1-3}$alkylamino;

$R^2$ is halo, methyl, methoxy or trifluoromethoxy;

$R^3$ is hydrogen, halo, or trifluoromethyl;

$R^4$ is hydrogen, or halo;

$R^2$ and $R^3$ may form a radical —OCF$_2$—O— in the 3,4-position;

Alk is straight or branched $C_{1-5}$alkanediyl or $C_{2-5}$alkenediyl;

$R^5$ is hydrogen, hydroxy, $C_{1-3}$alkyloxy, halo, $R^6R^7$N—C(=O)— or $R^8$—O—C(=O)—;

$R^6$ is $C_{1-3}$alkyl, $C_{3-6}$cycloalkyl or $(C_{3-6}$cycloalkyl$)C_{1-3}$alkyl;

$R^7$ is hydrogen or $C_{1-3}$alkyl; or $R^6$ and $R^7$ form pyrrolidinyl optionally substituted with hydroxyl;

$R^8$ is hydrogen or $C_{1-3}$alkyl;

or a pharmaceutically acceptable addition salt or a hydrate or a solvate thereof.

The present invention more particularly relates to a compound of Formula (I) or a stereoisomeric form thereof, wherein $R^1$ is unsubstituted benzodioxan-6-yl; unsubstituted pyridinyl; or pyridinyl substituted with 1 or 2 substituents selected from the group consisting of chloro, methyl, ethyl, methoxymethyl and ethylamino;

$R^2$ is halo, methyl, methoxy or trifluoromethoxy;

$R^3$ is hydrogen, halo, or trifluoromethyl;

$R^4$ is hydrogen, or halo;

Alk is straight or branched $C_{1-5}$alkanediyl;

$R^5$ is hydroxyl or $R^6R^7$N—C(=O)—;

$R^6$ is methyl or ethyl;

$R^7$ is hydrogen or methyl;

or a pharmaceutically acceptable addition salt or a hydrate or a solvate thereof.

The present invention most particularly relates to a compound of Formula (I) or a stereoisomeric form thereof, wherein $R^1$ is unsubstituted benzodioxan-6-yl; pyridinyl substituted with 1 methyl or ethylamino group; or pyridinyl substituted with 2 methyl groups;

$R^2$ is fluoro, chloro, methoxy or trifluoromethoxy;

$R^3$ is hydrogen, fluoro or trifluoromethyl;

$R^4$ is hydrogen, or fluoro;

Alk is straight or branched $C_{1-5}$alkanediyl;

$R^5$ is hydroxyl or $R^6R^7$N—C(=O)—;

$R^6$ is methyl or ethyl;

$R^7$ is hydrogen or methyl;

or a pharmaceutically acceptable addition salt or a hydrate or a solvate thereof.

Preferred compounds are compounds (alphaS)-alpha-ethyl-3-[[3-methoxy-5-(trifluoromethyl)phenyl]amino]-1-(2-methyl-4-pyridinyl)-1H-1,2,4-triazole-5-ethanol—E137;

3-[(2,2-difluoro-1,3-benzodioxol-5-yl)amino]-1-(2,6-dimethyl-4-pyridinyl)-N-ethyl-1H-1,2,4-triazole-5-acetamide—E200;

N-cyclopropyl-3-[(2,2-difluoro-1,3-benzodioxol-5-yl)amino]-1-(2,6-dimethyl-4-pyridinyl)-1H-1,2,4-triazole-5-acetamide—E180;

(alphaS)-alpha-ethyl-1-(2-methyl-4-pyridinyl)-3-[(2,3,4-trifluorophenyl)amino]-1H-1,2,4-triazole-5-ethanol—E130;

(alphaS)-1-(2,6-dimethyl-4-pyridinyl)-alpha-ethyl-3-[(2,3,4-trifluorophenyl)amino]-1H-1,2,4-triazole-5-ethanol—E127;

(alphaS)-1-(2,6-dimethyl-4-pyridinyl)-alpha-methyl-3-[(2,3,4-trifluorophenyl)amino]-1H-1,2,4-triazole-5-ethanol—E189;

3-[(3,4-difluorophenyl)amino]-1-(2,6-dimethyl-4-pyridinyl)-N-ethyl-1H-1,2,4-triazole-5-acetamide—E167;

N-cyclopropyl-1-(2,6-dimethyl-4-pyridinyl)-3-[[3-(trifluoromethoxy)phenyl]amino]-1H-1,2,4-triazole-5-acetamide—E182;

3-[(3-chloro-2-fluorophenyl)amino]-1-(2,6-dimethyl-4-pyridinyl)-N-ethyl-1H-1,2,4-triazole-5-acetamide—E153;

(alphaS)-1-(2,6-dimethyl-4-pyridinyl)-alpha-ethyl-3-[(3,4,5-trifluorophenyl)amino]-1H-1,2,4-triazole-5-ethanol—E188;

(alphaS)-alpha-ethyl-1-(2-methyl-4-pyridinyl)-3-[(3,4,5-trifluorophenyl)amino]-1H-1,2,4-triazole-5-ethanol—E187;

(alphaS)-alpha-ethyl-3-[(3-fluoro-5-methoxyphenyl)amino]-1-(2-methyl-4-pyridinyl)-1H-1,2,4-triazole-5-ethanol—E186;

(alphaS)-1-(2,6-dimethyl-4-pyridinyl)-alpha-ethyl-3-[(3-fluoro-5-methoxyphenyl)amino]-1H-1,2,4-triazole-5-ethanol—E190;

(alphaS)-3-[(3-chloro-5-methoxyphenyl)amino]-1-(2,6-dimethyl-4-pyridinyl)-alpha-ethyl-1H-1,2,4-triazole-5-ethanol—E205;

3-[(3,4-difluorophenyl)amino]-1-(2,6-dimethyl-4-pyridinyl)-N,N-dimethyl-1H-1,2,4-triazole-5-propanamide—E234; and 3-[(2,2-difluoro-1,3-benzodioxol-5-yl)amino]-1-(2,6-dimethyl-4-pyridinyl)-N,N-dimethyl-1H-1,2,4-triazole-5-propanamide—E235;

and the acid addition salts and solvates thereof.

As used hereinbefore and hereinafter $C_{1-3}$cycloalkyl as a group or part of a group defines straight or branched chain saturated hydrocarbon radicals having from 1 to 3 carbon atoms such as methyl, ethyl, propyl and 1-methylethyl;

$C_{3-6}$cycloalkyl as a group or part of a group defines cyclopropyl, cyclobutyl, cyclopentyl and cyclohexyl;

$C_{1-6}$alkanediyl defines bivalent straight and branched chain saturated hydrocarbon radicals having from 1 to 6 carbon atoms such as, for example, methylene, 1,2-ethanediyl, 1,3-propanediyl, 1,4-butanediyl, 1,5-pentanediyl and the branched isomers thereof;

$C_{2-6}$alkenediyl defines bivalent straight and branched chain unsaturated hydrocarbon radicals having from 2 to 6 carbon atoms such as for example 1,2-ethenediyl, 1,3-prop-1-enediyl and the like;

halo is fluoro, chloro, bromo or iodo.

It will be appreciated that some of the compounds according to formula (I) and the addition salts, hydrates and solvates thereof may contain one or more centers of chirality and exist as stereoisomeric forms.

The term "stereoisomeric forms" as used hereinbefore or hereinafter defines all the possible stereoisomeric forms which the compounds according to formula (I) and their addition salts may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms according to formula (I) and their salts, solvates, substantially free, i.e. associated with less than 10%, preferably less than 5%, in particular less than 2% and most preferably less than 1% of the other isomers.

For therapeutic use, salts of the compounds according to formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds according to formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The term solvates refers to alcoholates which the compounds according to formula (I) as well as the salts thereof, may form.

Some of the compounds according to formula (I) may also exist in their tautomeric form. Such forms although not explicitly indicated in the above formula are intended to be included within the scope of the present invention.

Preparation of the Compounds

A compound according to the invention can generally be prepared by a succession of steps, each of which is known to the skilled person. In particular, the compounds in this patent application can be prepared according to one or more of the following preparation methods. In the following Schemes, and unless otherwise indicated, all variables are used as defined in Formula (I). Q represents

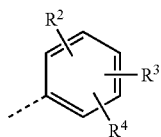

wherein $R^2$, $R^3$ and $R^4$ are as defined in Formula (I).

In some of the following intermediate structures, the definition of the radical $R^5$ is expanded to include HO—$CH_2$ (Ie), substituted-silyloxy (If and IV-a) and (alkyl or aryl)sulfonyloxy (Ig).

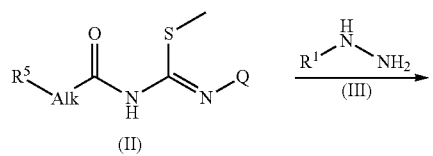

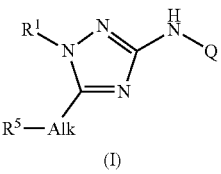

The compounds of this invention can be prepared according to Scheme 1 by transforming an N-acyl carbomimidothioic acid, methyl ester derivative of general formula (II) into the 1,2,4-triazoles of formula (I) using an appropriate hydrazine derivative (III) under art known conditions. This transformation is typically performed in an aprotic solvent, such as DMF or the like, and is most advantageously performed in the presence of a soft Lewis acid, in particular mercury (II) chloride ($HgCl_2$), and requires a temperature between room temperature and 150° C. In a particular embodiment, the reaction temperature is between 70° and 120° C., most preferably 80° C. The intermediates of formula (II) may occur in an E or Z configuration or a mixture thereof, as well as in the tautomeric form (II-a) again in an E or Z configuration or a mixture thereof (Scheme 2).

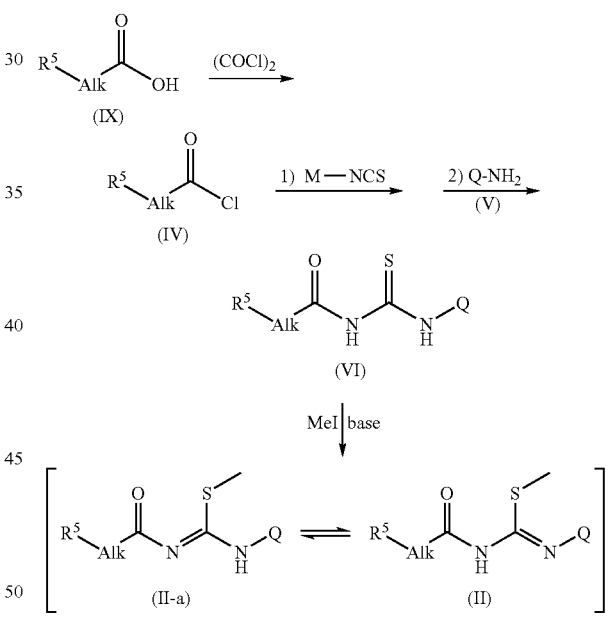

The common intermediate (II) in the synthesis of the trisubstituted triazoles of the present invention is typically prepared by a protocol that consists of 3 synthetic transformations (Scheme 2), starting from a carboxylic acid cloride of the general formula (IV).

In a first step the acyl chloride (IV) is reacted with a monovalent cation thiocyanate (M-NCS in Scheme 2), such as for example potassium thiocyanate or ammonium thiocyanate to yield the corresponding acyl isothiocyanate in situ. This reaction is usually performed using acetone as a solvent and at a temperature between 0° C. and 70° C., preferably at room temperature.

The intermediate acyl isothiocyanate is not isolated but treated in the same reaction medium with an appropriate aromatic amine (V) to yield the N-acyl thiourea of the general formula (VI). This transformation is usually performed at a temperature between 0° C. and 70° C., preferably at room temperature.

In a final step, S-methylation of the N-acyl thiourea (VI) provides the N-acyl carbomimidothioic acid, methyl ester derivative of general formula (II). This transformation is effected by methyl iodide and requires the presence of a strong base, preferably a strong inorganic base, such as NaH and is performed in an aprotic solvent such as for example DMF, THF and the like, at a temperature ranging from −70° C. to room temperature, preferably 0° C. More preferably, said transformation is effected in the presence of potassium carbonate as the inorganic base, in acetone as the solvent at a temperature between 0° C. and 60° C., preferably room temperature.

Optionally, in those cases where the acyl chloride (IV) is not commercially available, said acyl chloride (IV) can be prepared from the corresponding carboxylic acid (IX) by art known conditions. For example, acyl chloride (IV) can be obtained by treatment of the carboxylic acid (IX) with an excess of oxalyl chloride, optionally in the presence of DMF as a catalyst, at a temperature preferably in the range between 0° C. and 50° C. Said transformation may also be effected in the presence of an organic solvent, such as dichloromethane or the like.

In specific examples of compounds described in the present invention, the acyl chloride (IV) requires prior functionalization and protection of certain functional groups in order to be compatible with reaction conditions further down the overall synthetic sequence. For instance, when $R^5$ is hydroxyl, a synthetic sequence as shown in Scheme 3 can be followed to prepare the hydroxyl protected acyl chloride of the general formula (IVa) (Scheme 3).

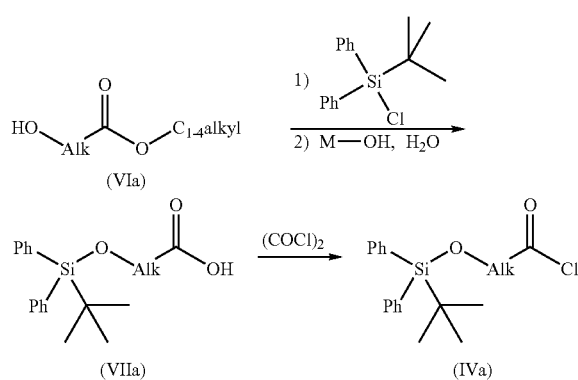

In a first step, the hydroxyl moiety in an alkane carboxylic ester of the general formula (VIIa) is protected by an appropriate silyl protecting group. In particular, a diphenyltertbutyl group can be used, as this group is inert to the reaction conditions as described hereinbefore and hereinafter. In a preferred embodiment, the hydroxyl ester (VIIa) is treated with tert-butyl(chloro)diphenylsilane in the presence of imidazole as a base, optionally in the presence of dimethylamino pyridine (DMAP) as a catalyst. A preferred solvent is a polar aprotic solvent, such as DMF, or the like. The reaction temperature is preferably in the range between 0° C. to room temperature. In a subsequent transformation, the alkyl carboxylic acid ester is hydrolyzed to yield the corresponding carboxylic acid of the general formula (VIIIa). This transformation can be effected by using a metal hydroxide (M-OH), such as potassium hydroxide, or more preferably lithium hydroxide. The reaction is performed in an aqueous environment, and is most advantageously carried out in the presence of at least one, or more preferably, two water miscible organic co-solvents, such as THF and methanol, or the like.

The acid chloride of the general formula (IVa) can be obtained by treatment of the carboxylic acid (VIIIa) with an excess of oxalyl chloride, optionally in the presence of DMF as a catalyst, at a temperature preferably in the range between 0° C. and 50° C. Said transformation may also be effected in the presence of an organic solvent, such as dichloromethane or the like.

Several compounds of the general formula (I) can be obtained by functional group transformations involving the substituent $R^5$. The Schemes 4-8 represent examples of said functional group transformations. Scheme 4 represents the preparation of carboxylic acid amides of the general formula (Ib) from the corresponding carboxylic acid esters (Ic) involving the treatment with a primary or secondary aliphatic amine $HNR^6R^7$. In one embodiment, said transformation can be effected directly from the ester (Ic). A preferred solvent is a protic solvent, such as a lower alkyl alcohol, for instance methanol or the like. The preferred reaction temperature is between room temperature and 120° C.

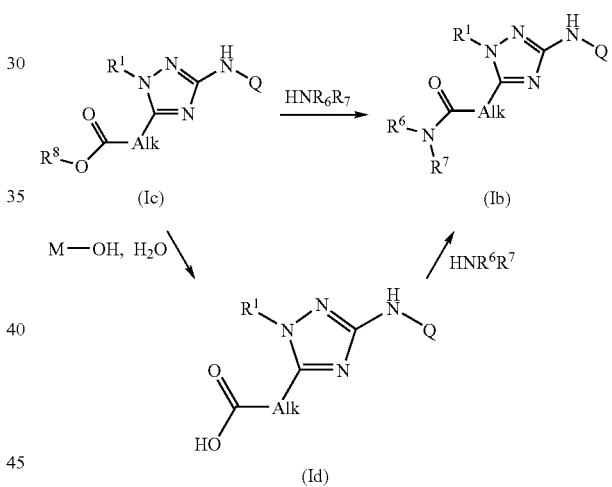

Alternatively, the alkyl carboxylic acid ester (Ic) is first hydrolyzed to yield the corresponding carboxylic acid of the general formula (Id). This transformation can be effected by using a metal hydroxide (M-OH), such as potassium hydroxyide, or more preferably lithium hydroxide. The reaction is performed in an aqueous environment, and is most advantageously carried out in the presence of at least one, or more preferably two water miscible organic co-solvents, such as THF and methanol, or the like. Further conversion of the carboxylic acid (Id) into the amides of formula (Ib) is done using art known procedures, such as for example the treatment with a primary or secondary amine $HNR_6R_7$ as defined herein-before in the presence of a conventional amide coupling reagent such as HBTU (O-benzotriazole-N,N,N',N'-tetramethyl uronium hexafluorophosphate), EDCI (N'-(ethylcarbonimidoyl)-N,N-dimethyl-1,3-propanediamine monohydrochloride), or EDAC (N'-(ethylcarbonimidoyl)-N, N-dimethyl-1,3-propanediamine), in an aprotic solvent like DCM, or more preferably in a polar aprotic solvent like THF or DMF in the presence of an amine base additive, such as diisopropyl ethyl amine. Under certain circumstances the use of HOBT (1-hydroxy-1H-benzotriazole) as an additive is an advantage.

When $R^5$ in a compound of the general formula (I) is a primary hydroxyl function, such as in the compounds of the general formula (Ie), these compounds can be obtained as is outlined in Scheme 5 starting from the carboxylic acid ester (Ic). This transformation can be successfully carried out using sodium borohydride in the presence of calcium chloride in a solvent system consisting of a lower alkyl alcohol, such as methanol, and an aprotic solvent, such as THF. The preferred reaction temperature is between 0° C. and room temperature. Alternatively, when the reactivity of the ester moiety is lower, a stronger reducing agent can be advantageously used. Specifically, lithium aluminum hydride in an aprotic solvent such as diethyl ether or THF, or the like, can afford the primary alcohol (Ie). The preferred reaction temperature is between 0° C. and room temperature.

Scheme 5

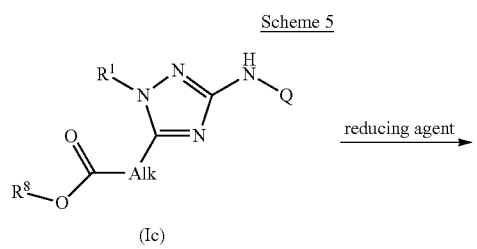

In those cases where $R^5$ is a hydroxyl function in a compound of the general formula (I), and where said hydroxyl group is attached to a secondary carbon atom, a compound of the general formula (Ie') can be obtained by removal of a silyl protecting group, as is shown in Scheme 6. In a particular embodiment, a diphenyltertbutyl group in a compound of the general formula (If) is removed by a nucleophilic fluorine source, such as tetrabutylammonium fluoride (TBAF). This transformation is preferably carried out in an aprotic solvent such as THF, or the like. The preferred reaction temperature is between 0° C. and 50° C., in particular at room temperature.

Scheme 6

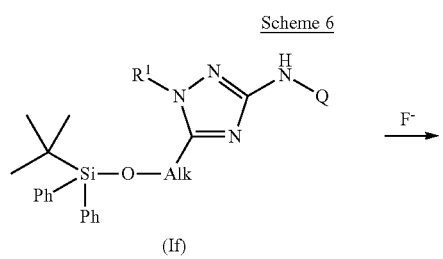

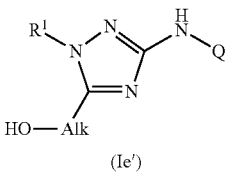

The compounds of the general formula (I), with $R^5$ is halo, can be obtained as is outlined in Scheme 7. In a first step the hydroxyl moiety in (Ie') is functionalized as a methyl sulfonate group to yield (Ig). This conversion is effected by treatment of (Ie') with methane sulfonyl chloride in the presence of an amine base, such as triethyl amine, or the like, in a halogenated solvent such as dichloromethane, or the like, optionally in the presence of dimethylamino pyridine (DMAP) as a catalyst. The preferred reaction temperature is between 0° C. and room temperature. Under these conditions a significant amount of the chlorinated compound (Ih) is formed. When a mixture of (Ig) and (Ih) is treated with a nucleophilic fluorine source, such as tetrabutylammonium fluoride, said methane sulfonate (Ig) is converted into the fluoro alkane (Ii). A preferred solvent is an aprotic solvent, such as THF, or the like. The preferred reaction temperature is between 0° C. and 70° C., more preferably between room temperature and 50° C.

Scheme 7

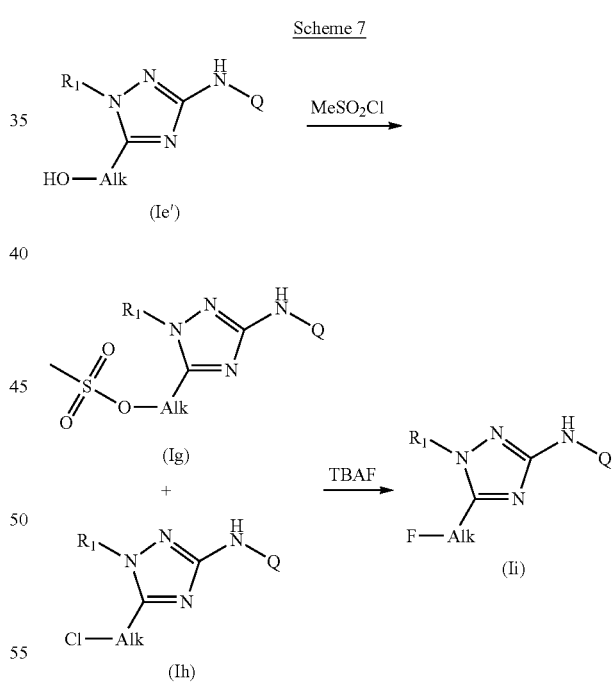

In a particular setting of the present invention, 5-alkylidene 1,2,4-triazoles of the general formula (Ij) can be obtained under Mitsunobu conditions, by starting from a secondary alcohol of the general formula (Ie"). A secondary alcohol (Ie") is treated with an aromatic carboxylic acid, such as benzoic acid or 4-nitrobenzoic acid, or the like, in the presence of a phosphine, such as triphenylphosphine, or the like, and a azodicarboxylate, such as diisopropyl azodicarboxylate (DIAD), or the like, to give the alkylidene (Ij).

Scheme 8

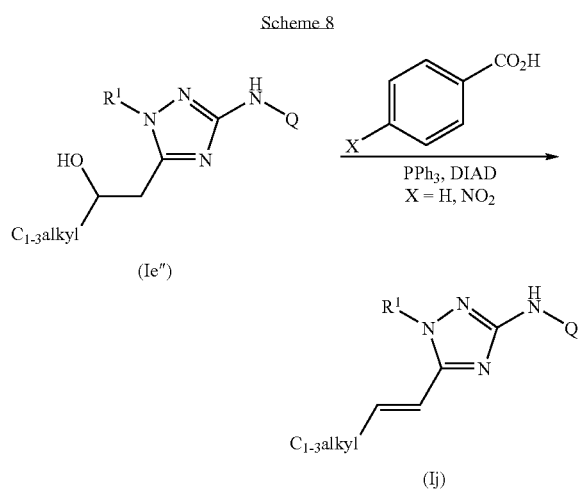

(Ie″)

(Ij)

In a particular setting of the present invention, where Alk in a compound of the general formula (I) represents a branched $C_{3-5}$alkanediyl fragment, said branching can be introduced in an intermediate of the general formula (VIa), to afford an intermediate of the general formula (IIb) (Scheme 9). The compound (VIa), which contains an activated methylene function, is treated with an $haloC_{1-4}$alkane, such as iodomethane, in an aprotic solvent such as acetone, in the presence of an inorganic base, such as potassium carbonate, or the like, to afford a compound of the general formula (IIb). The preferred reaction temperature is between 0° C. and 50° C., in particular room temperature. Similarly to what has been described hereinbefore, a compound (IIb) can be transformed into a compound of the general formula (I), as described in Scheme 1.

Scheme 9

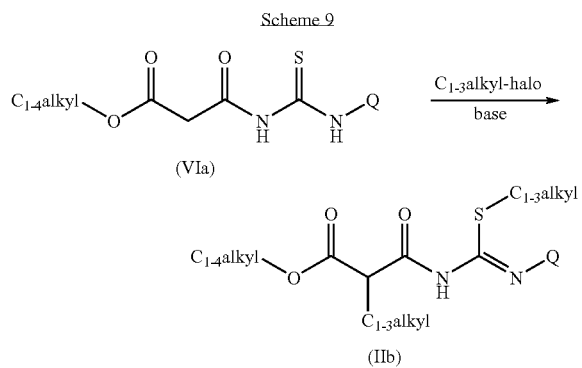

(VIa)

(IIb)

In another embodiment of the present invention, compounds of the general formula (I) can be obtained by functional group transformations involving the substituent $R^1$. The Schemes 10-12 represent examples of said functional group transformations.

An alkoxy substituted pyridinyl 1,2,4-triazole of the general formula (II) wherein $R^9$ represents hydrogen, halo, $C_{1-3}$alkyl, $C_{1-3}$alkyloxy, $C_{1-3}$alkylamino, $C_{3-6}$cycloalkyl, $C_{3-6}$cycloalkyloxy, $C_{3-6}$cycloalkylamino, $(C_{3-6}$cycloalkyl$)C_{1-3}$alkyl, $(C_{3-6}$cycloalkyl$)C_{1-3}$alkyloxy or $(C_{3-6}$cycloalkyl$)C_{1-3}$alkylamino, can be obtained by treatment of a chloro substituted pyridinyl 1,2,4-triazole of the general formula (Ik) with a sodium alkoxide, $NaOC_{1-3}$alkyl, in the corresponding alcoholic solvent $HOC_{1-3}$alkyl, for example methanol when sodium methoxide is used as the reagent, and heating at high temperatures, preferably at 100-130° C. in a pressure tube or microwave oven (Scheme 10). $C_{3-6}$cycloalkyloxy and $(C_{3-6}$cycloalkyl$)C_{1-3}$alkyloxy substituted pyridinyl derivatives can be prepared analogously.

Scheme 10

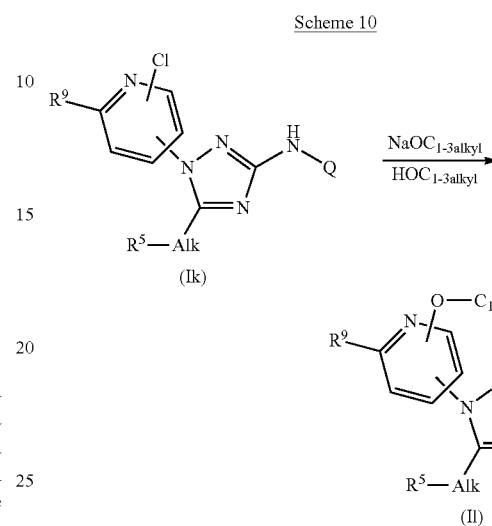

(Ik)

(Il)

An amino or alkylamino substituted pyridinyl 1,2,4-triazole of the general formula (Im) wherein $R^9$ represents hydrogen, halo, $C_{1-3}$alkyl, $C_{1-3}$alkyloxy, $C_{1-3}$alkylamino, $C_{3-6}$cycloalkyl, $C_{3-6}$cycloalkyloxy, $C_{3-6}$cycloalkylamino, $(C_{3-6}$cycloalkyl$)C_{1-3}$alkyl, $(C_{3-6}$cycloalkyl$)C_{1-3}$alkyloxy or $(C_{3-6}$cycloalkyl$)C_{1-3}$alkylamino can be obtained by treatment of a chloro substituted pyridinyl 1,2,4-triazole of the general formula (Ik) with a $C_{1-3}$alkylamine in an alcoholic solvent, such as ethanol or the like, and heating at high temperatures, preferably at 100-200° C. in a pressure tube or microwave oven (Scheme 11). $C_{3-6}$cycloalkylamino and $(C_{3-6}$cycloalkyl$)C_{1-3}$alkylamino substituted pyridinyl derivatives can be prepared analogously.

Scheme 11

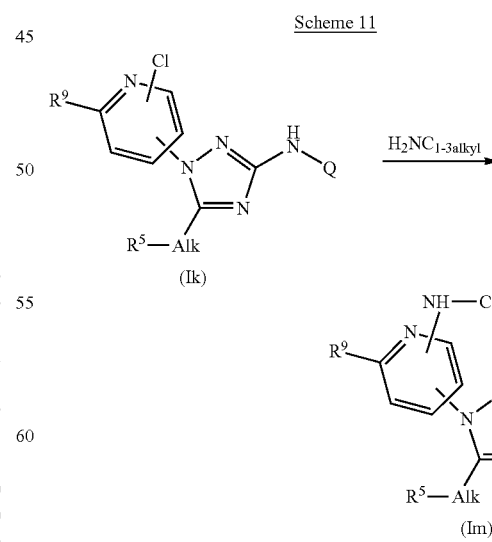

(Ik)

(Im)

A mono- or di-$C_{1-3}$alkyl substituted pyridinyl 1,2,4-triazole of the general formula (In) wherein $R^{10}$ represents hydrogen, halo, $C_{1-3}$alkyl, $C_{1-3}$alkyloxy or $C_{1-3}$alkylamino, can be obtained by treatment of a chloro or dichloro substituted pyridinyl 1,2,4-triazole of the general formula (Io) with an excess (3-15 equiv.) Grignard reagent $C_{1-3}$alkyl —MgBr in the presence of a catalytic amount of Fe(acac)$_3$ in a solvent system consisting of 85% THF and 15% NMP. Said transformation can be performed in a temperature range −10° C. and 50° C., most preferably between 0° C. and 25° C. (Scheme 12). One will recognize that through this methodology both 2-$C_{1-3}$alkyl and 2,6-di $C_{1-3}$alkyl pyridinyl compounds of the general formula (In) can be obtained, by starting from the corresponding 2-chloro or 2,6-dichloro precursors (Io), respectively. Pyridinyl derivatives substituted with $C_{3-6}$cycloalkyl or ($C_{3-6}$cycloalkyl)$C_{1-3}$alkyl can be prepared analogously.

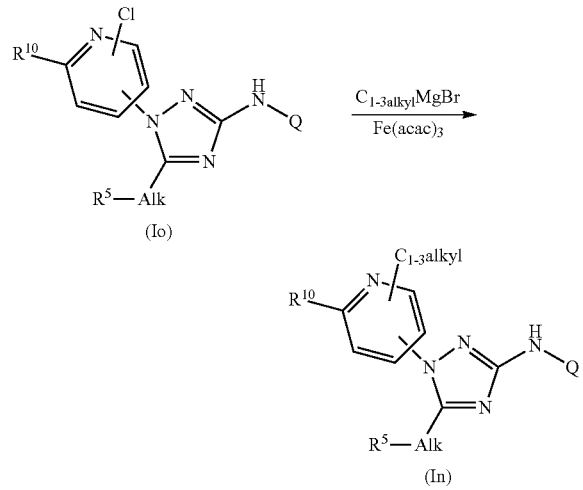

Scheme 12

Pharmacology

The compounds of the present invention were found to be positive allosteric modulators of the α7 nicotinic receptor. The α7 nicotinic receptor (α7 nAChR) belongs to the superfamily of cys-loop, ionotropic ligand-gated ion channels which includes the 5-HT$_3$, GABA$_A$ and glycine receptor families. It is activated by acetylcholine and its breakdown product choline and a major feature of the α7 nAChR is its rapid desensitisation in the persistent presence of an agonist. It is the second most abundant nicotinic receptor subtype in the brain and is an important regulator of release of many neurotransmitters. It has a discrete distribution in several brain structures with relevance to attentional and cognitive processes, such as the hippocampus and pre-frontal cortex and has been implicated in a variety of psychiatric and neurological disorders in humans. It is also implicated in the cholinergic inflammatory pathway.

Genetic evidence for its association with schizophrenia is seen in the form of strong linkage between a schizophrenia marker (sensory gating deficit) and the α7 locus on 15q13-14 and polymorphisms in core promoter region of the α7 gene.

Pathological evidence points to a loss of α7 immunoreactivity and α-Btx-binding in the hippocampus, frontal and cingulate cortex of schizophrenic brains, in Parkinson's and Alzheimer's disease and paraventricular nucleus and nucleus reuniens in autism.

Pharmacological evidence such as the marked smoking habits of schizophrenics compared to normals have been interpreted as an attempt by the patients to self-medicate to make up for a deficit in α7 nicotinergic transmission. Transient normalization of defects in sensory gating (pre-pulse inhibition PPI) in both animal models and man upon nicotine administration and temporary restoration of normal sensory gating in schizophrenics when forebrain cholinergic activity low (e.g. stage 2 sleep) have both been interpreted to be the result of transient activation of the α7 nicotinic receptor followed by desensitisation.

Thus there is good reason to suppose that activating the α7 nAChR will have therapeutically beneficial effects for a number of CNS (psychiatric and neurological) disorders.

As already mentioned the α7 nAChR rapidly desensitizes in the persistent presence of the natural transmitter acetylcholine as well as exogenous ligands such as nicotine. In the desensitized state the receptor remains ligand-bound but functionally inactive. This is not so much a problem for natural transmitters such as acetylcholine and choline since these are substrates for very powerful breakdown (acetylcholinesterase) and clearance (choline transporter) mechanisms. These transmitter breakdown/clearance mechanisms are likely to maintain the balance between activatible and desensitized α7 nAChRs in a physiologically useful range. However, synthetic agonists, which are not substrates for the natural breakdown and clearance mechanisms are perceived to have a potential liability both for over-stimulation and also to push the α7 nAChR population equilibrium towards a persistently desensitized state, which is undesirable in disorders in which deficiencies in α7 nAChR expression or function play a role. Agonists by their nature must target the ACh binding pocket which is highly conserved across the different nicotinic receptor subtypes leading to the potential for adverse reactions by non-specific activation of other nicotinic receptor subtypes. Therefore, to avoid these potential liabilities an alternative therapeutic strategy to α7 agonism is to enhance receptor responsiveness to the natural agonists with a positive allosteric modulator (PAM). A PAM is defined as an agent which binds to a site distinct from the agonist binding site, and therefore is not expected to have agonist or desensitization properties, but enhances the responsiveness of the α7 nAChR to the natural transmitter. The value of this strategy is that for a given amount of transmitter the magnitude of α7 nAChR response is increased in the presence of the PAM relative to the level of transmission possible in its absence. So for disorders in which there is a deficit in α7 nAChR protein the PAM-induced increase in α7 nicotinergic transmission can be beneficial. As a PAM relies on the presence of the natural transmitter the potential for over-stimulation is limited by the breakdown/clearance mechanisms for the natural transmitter.

The compounds of the present invention are classified as type 1-4, based on qualitative kinetic properties, as determined by whole-cell voltage-clamp recordings. This classification is based on the effect of an α7 PAM compound, as described hereinbefore, on the signal elicited by an agonist application. In particular, said agonist is choline at a concentration of 1 mM. In a preferred experimental setting, said α7 PAM compound and choline are simultaneously applied to the cell, as described hereinafter. Desensitization is defined as the closure of the receptor upon activation during the application of the agonist in whole-cell voltage-clamp electrophysiology measurements seen as the reduction of the outward current after initial activation by the agonist.

The definition of the PAM types 1-4 is described hereinafter:

Type 0 compounds minimally enhance the effect size of the current elicited by 1 mM choline.

Type 1 compounds enhance the effect size of the current elicited by 1 mM choline but minimally alter the kinetics of the receptor. In particular, the rate and the extent of desensitization, elicited by the agonist, is not affected. The compound-modulated response to 1 mM choline, therefore, is a close to linear scaling of the 1 mM choline response in absence of the α7 PAM compound.

Type 2 compounds enhance the effect size of the current elicited by 1 mM choline while reducing the rate and/or the extent of desensitization.

Type 3 compounds enhance the effect size of the current elicited by 1 mM choline. When tested at higher concentrations up to 10 μM they completely inhibit desensitization, in particular a 1 mM choline application of 250 milliseconds.

Type 4 compounds allow for an initial desensitization of the receptor followed by a re-opening of the receptor during agonist application. At low-potency concentrations of the α7 PAM compound, the agonist-induced activation, which is followed by desensitization, can still be separated from the compound-induced re-opening as an initial inward current-maximum. At higher potency concentrations of the α7 PAM compound, the re-opening occurs faster than the closure due to desensitization so that the initial current-maximum disappears.

It is accordingly an object of the present invention to provide methods of treatment that include administering either a positive allosteric modulator as the only active substance, thus modulating the activity of endogenous nicotinic receptor agonists such as acetylcholine or choline, or administering a positive allosteric modulator together with a nicotinic receptor agonist. In a particular form of this aspect of the invention, the method of treatment comprises treatment with a positive allosteric modulator of the α7 nicotinic receptor as described herein and an α7 nicotinic receptor agonist or partial agonist. Examples of suitable compounds with α7 nicotinic receptor agonistic activity include 1,4-Diazabicyclo[3.2.2]nonane-4-carboxylic acid, 4-bromophenyl ester, monohydrochloride (SSR180711A);
    (−)-spiro[1-azabicyclo[2.2.2.]octane-3,5'-oxazolidine]-2'-one;
    3-[(2,4-Dimethoxy)Benzylidene]-Anabaseine Dihydrochloride (GTS-21);
    [N-[(3R)-1-Azabicyclo[2.2.2]oct-3-yl]-4-chlorobenzamide Hydrochloride] PNU-282987;
    nicotine;
    varenicline;
    MEM3454;
    AZD-0328; and
    MEM63908.

Positive nAChR modulators of the present invention are useful for treatment or prophylaxis of psychotic disorders, intellectual impairment disorders or diseases or conditions in which modulation of α7 nicotinic receptor activity is beneficial. A particular aspect of the method of the invention is a method of treatment for learning deficit, cognition deficit, attention deficit or memory loss, modulation of α7 nicotinic receptor activity is expected to be beneficial in a number of diseases including Alzheimer's disease, Lewy Body Dementia, Attention Deficit Hyperactivity Disorder, anxiety, schizophrenia, mania, manic depression, Parkinson's disease, Huntington's disease, Tourette's syndrome, brain trauma or other neurological, degenerative or psychiatric disorders in which there is loss of cholinergic synapses, including jetlag, nicotine addiction, pain.

The compounds may also find therapeutical use as anti-inflammatory medicines because the nicotinic acetylcholine receptor α7 subunit is essential for inhibiting cytokine synthesis by the cholinergic inflammatory pathway. Examples of indications which may be treated by the compounds are endotoxaemia, endotoxic shock, sepsis, rheumatoid arthritis, asthma, multiple sclerosis, psoriasis, urticaria, inflammatory bowel disease, inflammatory bile disease, Crohn's disease, ulcerative colitis, post-operative ileus, pancreatitis, heart failure, acute lung injury and allograft rejection.

The compounds of the invention may find therapeutical use in the following indications as cognition in schizophrenia, cognition in Alzheimer' disease, mild cognitive impairment, Parkinson's disease, attention deficit hyperactivity disorder, ulcerative colitis, pancreatitis, arthritis, sepsis, postoperative ileus and acute lung injury.

In view of the above described pharmacological properties, the compounds according to formula (I) or any subgroup thereof, their, pharmaceutically acceptable addition salts, quaternary amines and stereochemically isomeric forms, may be used as a medicine. In particular, the present compounds can be used for the manufacture of a medicament for treatment or prophylaxis of psychotic disorders, intellectual impairment disorders or diseases or conditions in which modulation of the α7 nicotinic receptor is beneficial.

In view of the utility of the compounds according to formula (I), there is provided a method of treating warm-blooded animals, including humans, suffering from or a method of preventing warm-blooded animals, including humans, to suffer from diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain. Said methods comprise the administration, i.e. the systemic or topical administration, preferably oral administration, of an effective amount of a compound according to formula (I), including all stereochemically isomeric forms thereof, a pharmaceutically acceptable addition salt, a solvate, or a quaternary amine thereof, to warm-blooded animals, including humans.

One skilled in the art will recognize that a therapeutically effective amount of the PAM's of the present invention is the amount sufficient to modulate the activity of the α7 nicotinic receptor and that this amount varies inter alia, depending on the type of disease, the concentration of the compound in the therapeutic formulation, and the condition of the patient. Generally, an amount of PAM to be administered as a therapeutic agent for treating diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain will be determined on a case by case by an attending physician.

Generally, a suitable dose is one that results in a concentration of the PAM at the treatment site in the range of 0.5 nM to 200 μM, and more usually 5 nM to 50 μM. To obtain these treatment concentrations, a patient in need of treatment likely will be administered between 0.01 mg/kg to 2.50 mg/kg body weight, in particular from 0.1 mg/kg to 0.50 mg/kg body weight. The amount of a compound according to the present invention, also referred to here as the active ingredient, which is required to achieve a therapeutically effect will be, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The present invention also provides compositions for preventing or treating diseases in which modulation of the α7 nicotinic receptor is beneficial, such as schizophrenia, mania, and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, brain trauma, jetlag, nicotine addiction and pain. Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Description of compositions with excipients (%). Depending on the mode of administration, the pharmaceutical composition will comprise from 0.05 to 99% by weight, preferable from 0.1 to 70% by weight, more preferably from 0.1 to 50% by weight of the active ingredient, and, from 1 tot 99.95% by weight, preferably from 30 to 99.9% by weight, more preferably from 50 to 99.9% by weight of a pharmaceutically acceptable carrier, all percentages being based on the total weight of the composition.

The compounds according to formula (I) may also be used in combination with other conventional α7 nicotinic receptor agonists, such as for example 1,4-Diazabicyclo[3.2.2] nonane-4-carboxylic acid, 4-bromophenyl ester, monohydrochloride (SSR180711A); (−)-spiro[1-azabicyclo[2.2.2.]octane-3,5'-oxazolidine]-2'-one; 3-[(2,4-Dimethoxy) Benzylidene]-Anabaseine Dihydrochloride (GTS-21); [N-[(3R)-1-Azabicyclo[2.2.2]oct-3-yl]-4-chlorobenzamide Hydrochloride]PNU-282987; nicotine; varenicline; MEM3454; AZD-0328 and MEM63908. Thus, the present invention also relates to the combination of a compound according to formula (I) and a α7 nicotinic receptor agonist. Said combination may be used as a medicine. The present invention also relates to a product comprising (a) a compound according to formula (I), and (b) a α7 nicotinic receptor agonist, as a combined preparation for simultaneous, separate or sequential use in the treatment of diseases wherein modulation of the α7 nicotinic receptor is beneficial. The different drugs may be combined in a single preparation together with pharmaceutically acceptable carriers.

EXPERIMENTAL PART

Several methods for preparing the compounds of this invention are illustrated in the following Examples. Unless otherwise noted, all starting materials were obtained from commercial suppliers and used without further purification.

Hereinafter, "THF" means tetrahydrofuran; "DMF" means N,N-dimethylformamide; "EtOAc" means ethyl acetate; "DCM" means dichloromethane; "DIPE" means diisopropylether; "DMSO" means dimethylsulfoxide; "DMAP" means 4-(dimethylamino)pyridine; "min" means minutes; "sat." means saturated; "MeOH" means methanol; "EtOH" means ethanol; "Et₂O" means diethyl ether; "acac" means acetyl acetonate; "TBAF" means tetrabutylammonium fluoride; "DIAD" means diisopropyl diazodicarboxylate; "NH₄OAc" means ammonium acetate and "r.t." means room temperature.

Microwave assisted reactions were performed in a single-mode reactor: Initiator™ Sixty EXP microwave reactor (Biotage AB), or in a multimode reactor: MicroSYNTH Labstation (Milestone, Inc.).

The following examples are intended to illustrate but not to limit the scope of the present invention.

Description 1

(3S)-3-[[(1,1-Dimethylethyl)diphenylsilyl]oxy]-butanoic acid methyl ester (D1)

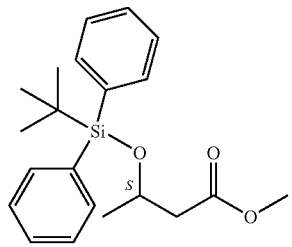

tert-Butyl(chloro)diphenylsilane (15.282 g, 55.6 mmol) was added dropwise to an ice-cooled and stirred solution of (S)-3-hydroxybutanoic acid methyl ester (5.473 g, 46.3 mmol) and 1H-imidazole (6.939 g, 102 mmol) and DMAP (0.566 g, 4.63 mmol) in DMF (250 mL). After 10 min., the cloudy reaction mixture was allowed to warm to r.t. and stirred overnight. The reaction mixture was taken up in EtOAc, then washed successively with H₂O (×3), 1N HCl and a sat. NaHCO₃ solution. The organic phase was dried (Na₂SO₄), filtered and concentrated to give a viscous colourless oil.

Yield: 10.614 g of intermediate D1 (64%).

Description 2

(3S)-3-[[(1,1-Dimethylethyl)diphenylsilyl]oxy]-butanoic acid (D2)

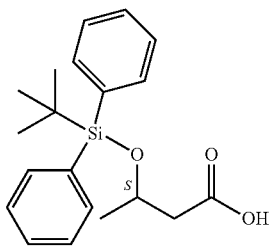

A solution of lithium hydroxide (2.1 g, 89.3 mmol) in MeOH/H₂O (80 mL/80 mL) was added to a stirred solution of intermediate D1 (10.6 g, 29.8 mmol) in THF (80 mL) at r.t. The reaction mixture was stirred overnight. The solvent was then removed under reduced pressure and the residue was partitioned between H₂O/EtOAc. The layers were separated and the aqueous phase was extracted with EtOAc (×3), then acidified to pH 1 with concentrated HCl and extracted again with EtOAc (×3). The combined organic extracts were dried (Na₂SO₄), filtered and concentrated under reduced pressure to give a clear yellow viscous oil. Yield: 11 g of intermediate D2 (99.9%).

Description 3

(3S)-3-[[(1,1-Dimethylethyl)diphenylsilyl]oxy]-butanoyl chloride (D3)

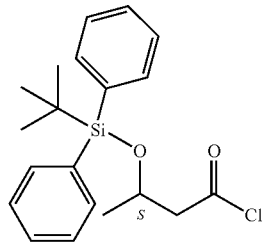

Oxalyl chloride (4.1 mL, 48 mmol; conc. 1.5 g/mL) was added dropwise to a stirred solution of intermediate D2 (11 g, 32 mmol) and DMF (1 mL) in DCM (300 mL) at r.t. for 90 min. The reaction mixture was evaporated under reduced pressure and co-evaporated with toluene (×3) to give the crude intermediate D3 as a yellow oil. This material was used in the next step of the reaction sequence without any further purification.

Description 4

(3S)-3-[[(1,1-Dimethylethyl)diphenylsilyl]oxy]-N-[[[4-fluoro-3-(trifluoromethyl)phenyl]amino]thioxomethyl]butanamide (D4)

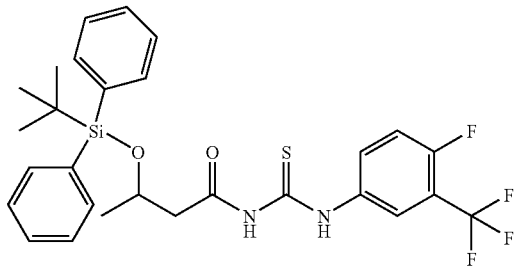 [SMILES: CC(CC(=O)NC(=S)Nc1ccc(F)c(C(F)(F)F)c1)O[Si](c1ccccc1)(c1ccccc1)C(C)(C)C]

Intermediate D3 (5.4 g, 14.9 mmol) was added dropwise to a stirred solution of ammonium thiocyanate (1.1 g, 14.9 mmol) in acetone (150 mL) at r.t. After 2 hours, 4-fluoro-(3-trifluoromethyl)aniline (2.7 g, 14.9 mmol) was added and the reaction mixture was stirred overnight at r.t. The solvent was removed under reduced pressure and the residue was partitioned between H₂O/DCM. The layers were separated and the aqueous phase was extracted with DCM (×2). The combined organic extracts were washed with brine, dried (Na₂SO₄) and filtered. The solvent was then evaporated to yield the crude material as a viscous dark orange oil yielding 8.8 g (104.9%). This material was purified by flash chromatography (Biotage; 40M column; eluent: EtOAc/heptane gradient elution from 0/100 to 40/60). Yield: 3.7 g of intermediate D4 (44.4%) as a viscous, yellow oil.

Description 5

4-[[[(3,4-Difluorophenyl)amino]thioxomethyl]amino]-4-oxo-butanoic acid ethyl ester (D5)

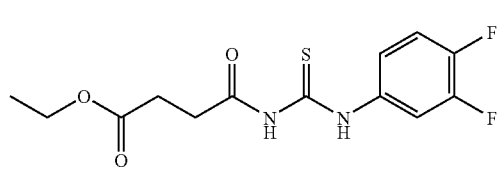 [SMILES: CCOC(=O)CCC(=O)NC(=S)Nc1ccc(F)c(F)c1]

A mixture of thiocyanic acid, ammonium salt (5 g, 0.065 mol) in CH$_3$CN (42 ml) was stirred for 15 min. at r.t. 4-Chloro-4-oxo-butanoic acid ethyl ester (0.061 mol) was added dropwise and the mixture was stirred for 30 min. at 60° C. The mixture was cooled to 0° C. and then 3,4-difluoroaniline (6 mL, 0.061 mol) was added dropwise. The reaction mixture was stirred for 30 min. at r.t. The mixture was then quenched with ice-water and stirred for 15 min. at 0° C. The mixture was filtered through a sinter funnel, dried and azeotroped with toluene to remove remaining water. Yield: 16.40 g of intermediate D5 (85%, yellow solid).

In a similar manner the following intermediates were prepared:

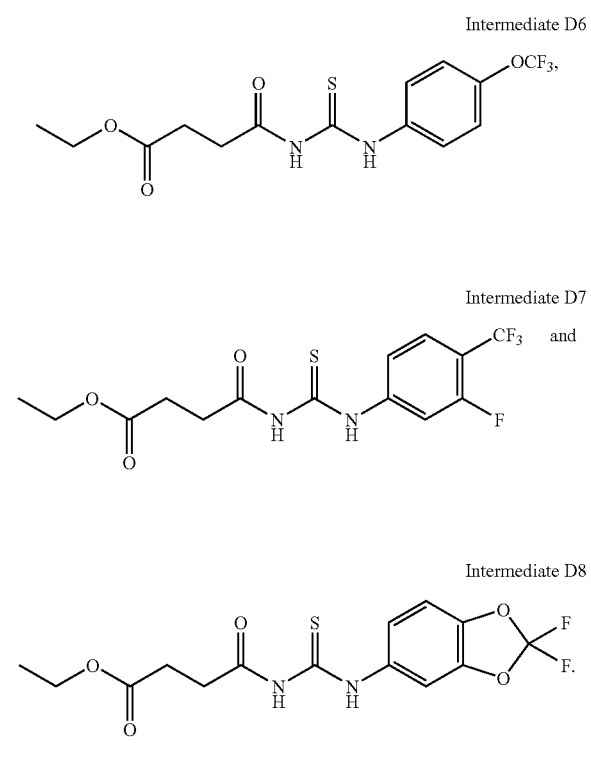

Description 9

N-[(3S)-3-[[(1,1-Dimethylethyl)diphenylsilyl]oxy]-1-oxobutyl]-N'-[4-fluoro-3-(trifluoromethyl)phenyl]-carbamimidothioic acid methyl ester (D9)

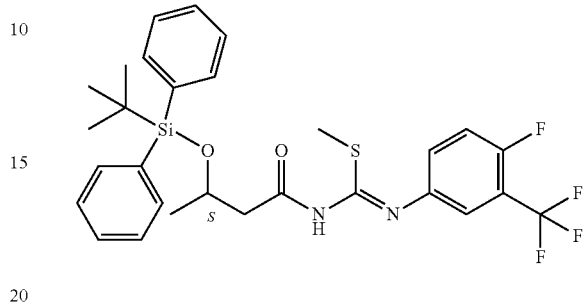

K$_2$CO$_3$ (1 g, 7.3 mmol) was added to a stirred solution of intermediate D4 (prepared according to Description 4) (3.7 g, 6.6 mmol) in acetone (70 mL) at r.t. After 50 min., CH$_3$I (0.5 mL, 7.9 mmol) was added dropwise and the reaction mixture was stirred at r.t. for 145 min. The solvent was removed under reduced pressure and the resulting residue was partitioned between H$_2$O/DCM. The layers were separated and the aqueous phase was extracted with DCM (×2). The combined organic extracts were washed with brine, dried (Na$_2$SO$_4$), filtered and the solvent was evaporated yielding the crude product as a viscous yellow oil. Yield: 3.8 g of intermediate D9 (99.4%).

In a similar manner the following intermediates were prepared:

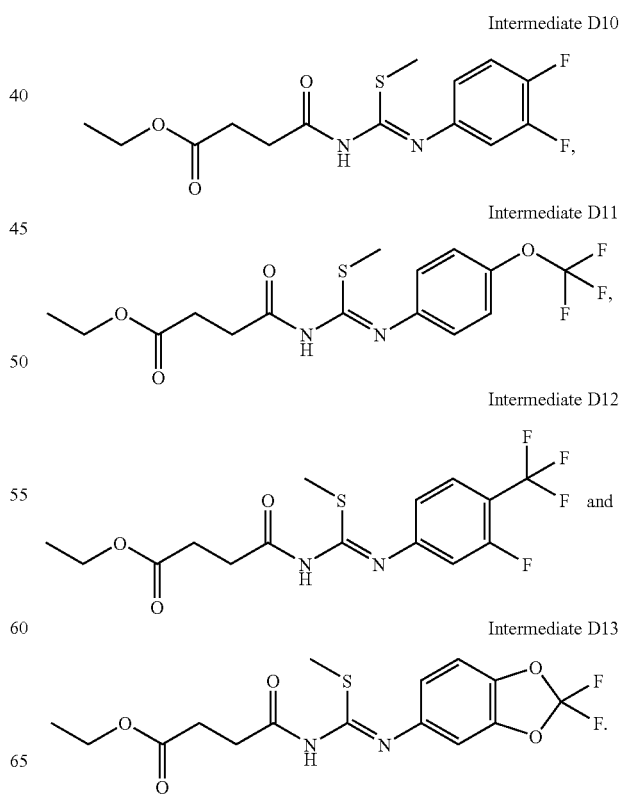

Intermediate D17

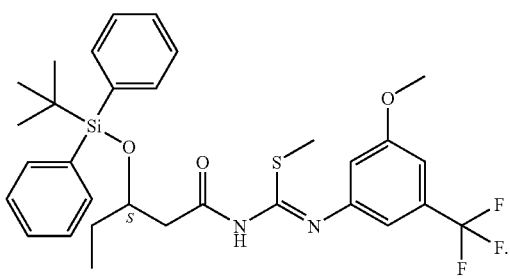

Description 14

5-[(2S)-2-[[(1,1-Dimethylethyl)diphenylsilyl]oxy]propyl]-N-[4-fluoro-3-(trifluoromethyl)phenyl]-1-(2-methyl-4-pyridinyl)-1H-1,2,4-triazol-3-amine (D14)

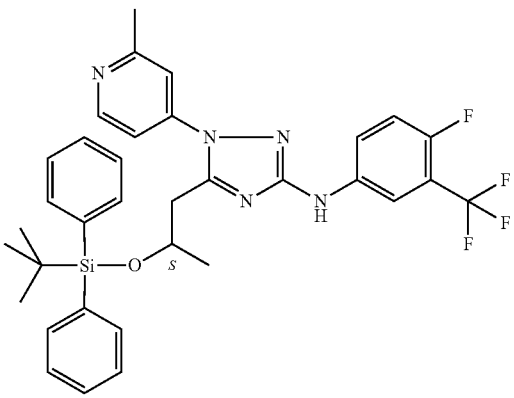

Mercury(II) chloride (1.8 g, 6.5 mmol) was added to a stirred solution of intermediate D9 (prepared according to Description 9) (3.8 g, 6.5 mmol) and 4-hydrazino-2-methylpyridine (0.8 g, 6.5 mmol) in DMF (65 mL) at room temperature. The reaction mixture was heated at 80° C. for 140 min. The cooled reaction mixture was poured onto ice and the precipitated product was collected by filtration to give a yellow semi-solid. Yield: 4.2 g of intermediate D14 (101.2%).

Description 15

3-[[[[4-Fluoro-3-(trifluoromethyl)phenyl]amino]thioxomethyl]amino]-3-oxo-propanoic acid ethyl ester (D15)

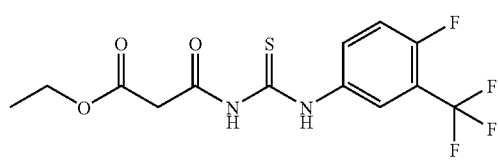 [SMILES: CCOC(=O)CC(=O)NC(=S)Nc1ccc(F)c(C(F)(F)F)c1]

3-Chloro-3-oxo-propanoic acid ethyl ester (5 g; 33.2 mmol) was slowly added to a stirred solution of thiocyanic acid, ammonium salt (1:1) (2.781 g; 36.5 mmol) in CH$_3$CN (110 ml) at room temperature. After 2 hours, 4-fluoro-3-(trifluoromethyl)benzenamine (4.27 ml; 33.2 mmol) was added. The solvent was removed under reduced pressure. The resulting residue partitioned between H$_2$O/DCM and the phases separated. The aqueous phase was extracted with DCM (×2) and the combined organic extracts were washed with brine, dried and filtered. Yield: 3.656 g of intermediate D15.

Description 16

3-[[(1Z)-[[4-Fluoro-3-(trifluoromethyl)phenyl]amino](methylthio)methylene]amino]-2-methyl-3-oxo-propanoic acid ethyl ester (D16)

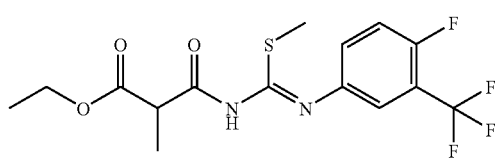 [SMILES: CCOC(=O)C(C)C(=O)N/C(=N/c1ccc(F)c(C(F)(F)F)c1)SC]

K$_2$CO$_3$ (0.831 g; 6.01 mmol) was added to a stirred solution of intermediate D15 (1.765 g; 5.01 mmol) in acetone (50 ml) at room temperature. After 40 minutes, CH$_3$I (0.624 ml; 10.0 mmol) was added dropwise. The reaction mixture was stirred at room temperature. The solvent was removed under reduced pressure and the residue partitioned between H$_2$O/DCM. The aqueous phase was extracted with DCM and the combined organic extracts were washed with brine, dried (Na$_2$SO$_4$) and filtered yielding an orange oil. LCMS showed 4 different products which were separated by flash chromatography using the Biotage system (40M column), eluent: DCM to 10% MeOH/DCM gradient elution. The third fraction contained the desired compound. Yield: 401 mg of intermediate D16.

Description D18

5-[(2S)-2-[[(1,1-Dimethylethyl)diphenylsilyl]oxy]butyl]-N-[3-methoxy-5-(trifluoromethyl)phenyl]-1-(2-methyl-4-pyridinyl)-1H-1,2,4-triazol-3-amine (D18)

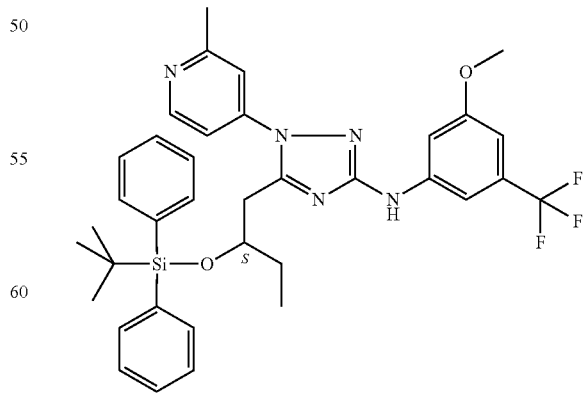

Mercury(II) chloride (5.2 g; 19.1 mmol) was added to a stirred solution of intermediate D17 (prepared according to Description 9) (11.5 g, 19.1 mmol) and 4-hydrazino-2-methylpyridine (3.1 g, 19.1 mmol) in DMF (180 mL) at room temperature. After 5 minutes, the reaction mixture was heated at 80° C. for 120 min. The reaction mixture was cooled to room temperature and the solvent was removed under reduced pressure. The residue was partitioned between H$_2$O/EtOAc. The aqueous phase was extracted with EtOAc (×2) and the combined organic extracts were washed with brine, dried (Na$_2$SO$_4$) and filtered yielding an yellow oil. Yield: intermediate D18 (41%).

Intermediate D18 (29 g; several batches combined) was dissolved in 1.5 liter EtOAc. A solution of Na$_2$S in water (20 ml) was added and the mixture was stirred vigorously for 2 hours. A black insoluble precipitate was formed (HgS). The reaction mixture was filtered over dicalite and treated again with Na$_2$S solution. The organic layer was separated and washed with brine. The organic layer was dried on MgSO$_4$, filtered and treated with silicagel S-thiol (2×2 hours at 50° C.). The mixture was filtered over dicalite and evaporated. The product crystallized while evaporation was nearly complete. Et$_2$O was added and the precipitate was filtered off. The product was dried in the vacuum oven at 50° C. Yield: 25.70 g intermediate D18.

Description D19

3-[[[[2-Fluoro-3-(trifluoromethyl)phenyl]amino] thioxomethyl]amino]-3-oxo-propanoic acid methyl ester (D19)

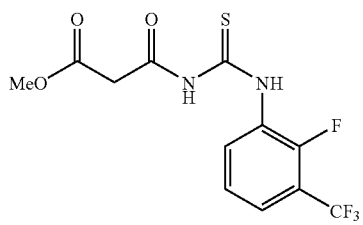 [SMILES: COC(=O)CC(=O)NC(=S)Nc1cccc(C(F)(F)F)c1F]

3-Chloro-3-oxo-propanoic acid methyl ester (7.5 g) in MeCN (50 ml) was slowly added to a stirred solution of ammonium thiocyanate (4.6 g) in MeCN (400 ml) at r.t. After 1.5 h, the reaction mixture was cooled to 0° C. and a solution of 2-fluoro-3-(trifluoromethyl)aniline (9.8 g) in MeCN (50 ml) was slowly added. After 5-10 min, the ensuing reaction mixture was allowed to warm to r.t. and after 1 h. the solvent was removed under reduced pressure and the resulting residue partitioned between H$_2$O/DCM and the phases separated. The aqueous phase was extracted with DCM (×2) and the combined organic extracts washed with brine, then dried (Na$_2$SO$_4$). Filtration and concentration gave the crude material as an amber oil. Yield: 17.1 g of intermediate D19 (60%).

Description D20

3-[[(1Z)-[[2-fluoro-3-(trifluoromethyl)phenyl] amino](methylthio) methylene]amino]-3-oxo-propanoic acid methyl ester

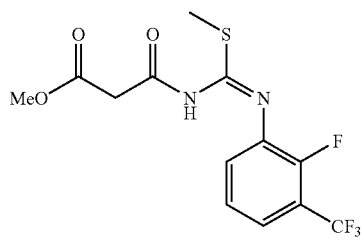 [SMILES: COC(=O)CC(=O)N/C(=N\c1cccc(C(F)(F)F)c1F)SC]

An ice-cooled solution of intermediate D19 (17.1 g) in THF (450 ml) was stirred under an atmosphere of N$_2$. NaOtBu (1 eq) was added and after 30 minutes a solution of iodomethane (3.15 ml) in THF was added dropwise. After another 30 minutes an additional NaOtBu (1 eq) was added and the contents stirred at ~0° C. When the reaction was completed after 45 minutes, a saturated solution of NH$_4$Cl was added and the reaction was diluted with EtOAc. The phases were separated and the aqueous phase extracted with EtOAc (×2). The combined organic extracts were washed with brine, then dried (Na$_2$SO$_4$). Filtration and concentration under reduced pressure gave the crude material as an amber oil. Yield: 17.2 g of intermediate D20 (59%).

Description D21

1-(2,6-Dimethyl-4-pyridinyl)-3-[[2-fluoro-3-(trifluoromethyl)phenyl]amino]-1H-1,2,4-triazole-5-acetic acid methyl ester (D21)

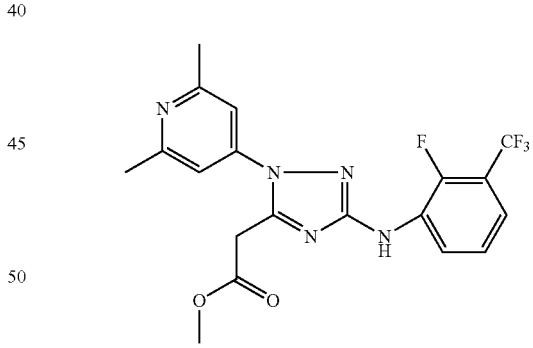

Mercury (II) chloride (7 g) was added to a stirred solution of intermediate D20 (9.1 g) and 2,6-dimethyl-4-hydrazinopyridine. HCl (4.48 g) in DMF (200 ml) at r.t. After 5 minutes at r.t., the ensuing reaction mixture was stirred at 70° C. overnight (reaction 40% complete). The contents were cooled to r.t. and the solvent removed under reduced pressure. The resulting residue was partitioned between H$_2$O and EtOAc and the phases separated. The aqueous phase was extracted with EtOAc (×2) and the combined organic extracts washed with brine, then dried (Na$_2$SO$_4$). Filtration and concentration gave a yellow oil which was taken up in EtOAc and a solution of sodium sulfide (4 g) in H$_2$O added (black precipitate formed). The ensuing reaction mixture was stirred vigorously at r.t. for several hours, then filtered through dicalite. The phases were separated and the aqueous phase extracted with EtOAc (×2) and the combined organic extracts washed with H₂O, then with brine and dried (Na₂SO₄). The contents were filtered and concentrated and the resulting oil taken up in DCM and Si-thiol (functionalised silica gel) added. The resulting suspension was stirred vigorously at r.t. for several hours, then filtered and evaporated to give an amber oil which was purified by flash chromatography using the Biotage system: eluent 20% EtOAc: 80% heptane to 100% EtOAc, gradient elution (elution of most impurities), then 10% MeOH/DCM to elute desired product as a sticky yellow oil. The yellow oil was stirred in DIPE overnight, then the contents filtered to give a pale yellow powder. Yield: 814 mg of intermediate D21 (6%).

Example 1

3-[(3,4-Difluorophenyl)amino]-1-(2,3-dihydro-1,4-benzodioxin-6-yl)-1H-1,2,4-triazole-5-propanoic acid (E1)

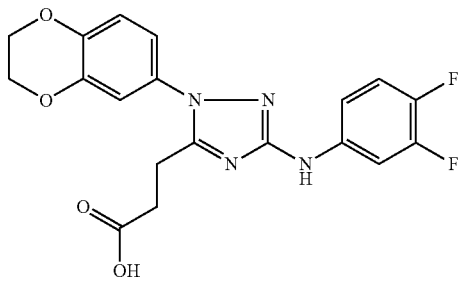 [SMILES: O=C(O)CCc1nc(Nc2ccc(F)c(F)c2)nn1-c1ccc2c(c1)OCCO2]

LiOH.H₂O (0.00277 mol) was added to a stirred solution of compound E114 (prepared according to Description 14) (0.00158 mol) in THF (9 ml) at r.t., MeOH (3 ml) and H₂O (3 ml). The reaction mixture was stirred for 1 hour at r.t.

The solvents were evaporated under reduced pressure. HCl (2 M, 20 ml) was added and the resulting precipitate was filtered off and dried. Yield: 0.570 g of compound E1 (90%, grey solid).

Example 2

3-[(3,4-Difluorophenyl)amino]-1-(2,3-dihydro-1,4-benzodioxin-6-yl)-N-methyl-1H-1,2,4-triazole-5-propanamide (E2)

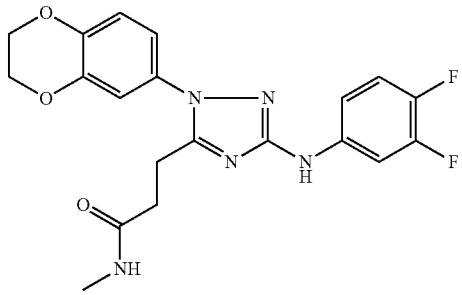 [SMILES: CNC(=O)CCc1nc(Nc2ccc(F)c(F)c2)nn1-c1ccc2c(c1)OCCO2]

Compound E114 (prepared according to Description 14) (0.00019 mol) was dissolved in CH₃NH₂, 2.0 M in THF (1.9 ml; 0.0038 mol) and the solution was refluxed for 12 hours. Approximately every 3 hours an additional portion of CH₃NH₂, 2.0 M in MeOH (1.9 ml; 0.0038 mol) and THF (1 ml) was added. The mixture was cooled and the solvent was evaporated under reduced pressure. The brown solid residue was purified by column chromatography over silica gel (eluent: DCM/(MeOH/NH₃) from 100/0 to 90/10). The product fractions were collected and the solvent was evaporated. Yield: 0.013 g of compound E2 (16%).

Example 3

3-[(3,4-Difluorophenyl)amino]-1-(2,3-dihydro-1,4-benzodioxin-6-yl)-N,N-dimethyl-1H-1,2,4-triazole-5-propanamide (E3)

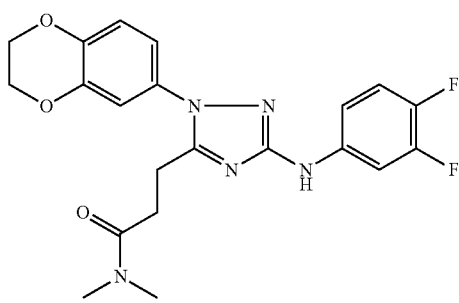 [SMILES: CN(C)C(=O)CCc1nc(Nc2ccc(F)c(F)c2)nn1-c1ccc2c(c1)OCCO2]

Compound E1 (prepared according to Ex.1) (0.00062 mol) was dissolved in DMF (5 ml). 1-Hydroxy-1H-benzotriazole (0.00186 mol), (3-Dimethylamino-propyl)-ethyl-carbodiimide.hydrochloride (1:1) (0.00186 mol) and N-ethyl-N-(1-methylethyl)-2-propanamine (0.00248 mol) were added, followed by addition of dimethylamine hydrochloride (1:1) (0.00124 mol). The reaction mixture was stirred for 3 hours at r.t. The reaction mixture was poured into water. The mixture was extracted with CHCl₃. The organic layer was separated, washed with a 1M HCl solution, then washed with brine and filtered through a hydrophobic frit. The solvents were evaporated under reduced pressure to give a yellow solid residue that was dried further for one hour (in the GeneVac®). The residue was triturated with diethyl ether, filtered off and dried. Yield: 0.245 g of compound E3 (92%).

Example 4

1-(2-Methoxy-3-pyridinyl)-N,N-dimethyl-3-[[3-(trifluoromethoxy)phenyl]amino]-1H-1,2,4-triazole-5-propanamide (E4)

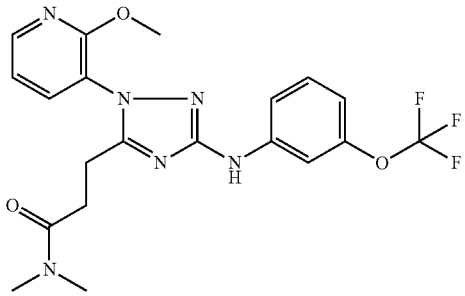 [SMILES: COc1ncccc1-n1nc(Nc2cccc(OC(F)(F)F)c2)nc1CCC(=O)N(C)C]

A mixture of compound E76 (prepared according to Ex.3) (0.20 g; 0.0004 mol), NaOCH₃ in MeOH (1 ml) and MeOH (4 ml) were stirred for 30 min. at 100° C. in the microwave. The reaction mixture was evaporated and the residue was purified by reversed-phase high-performance liquid chromatography (Shandon Hyperprep® C18 BDS (Base Deactivated Silica) 8 μm, 250 g, I.D. 5 cm). A gradient with 2 mobile phases was applied. Phase A: a 0.25% NH$_4$HCO$_3$ solution in water; phase B: CH$_3$CN). The desired fractions were collected, evaporated and dried. Yield: 38 mg of compound E4 (21%).

Example 5

N,N-Dimethyl-1-(2-methyl-3-pyridinyl)-3-[[3-(trifluoromethoxy)phenyl]amino]-1H-1,2,4-triazole-5-propanamide (E5)

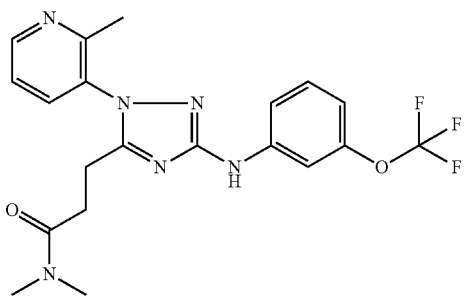 [SMILES: Cc1ncccc1-n1nc(Nc2cccc(OC(F)(F)F)c2)nc1CCC(=O)N(C)C]

A mixture of compound E76 (prepared according to Ex.3) (0.20 g; 0.0004 mol), Fe(acac)$_3$ (0.031 g; 0.0001 mol), THF (5 ml) and 1-methyl-2-pyrrolidinone (1.5 ml) was stirred at room temperature before CH$_3$MgBr in Et$_2$O, 2M (2 ml) and MeOH (5 ml) were added. The reaction mixture was evaporated and dissolved in DCM and H$_2$O and filtered on dicalite. The filtrate was dried on MgSO$_4$ and filtered off. The filtrate was evaporated. The product was dissolved in DIPE/H$_2$O. The organic layer was separated, dried (MgSO$_4$) and filtered. The filtrate was evaporated and the residue was purified by reversed-phase high-performance liquid chromatography (Shandon Hyperprep® C18 BDS (Base Deactivated Silica) 8 μm, 250 g, I.D. 5 cm). A gradient with 2 mobile phases was applied. Phase A: a 0.25% NH$_4$HCO$_3$ solution in water; phase B: CH$_3$CN). The desired fractions were collected, evaporated and dried. Yield: 81 mg of compound E5 (47%).

Example 6

N,N-Dimethyl-1-[2-(methylamino)-3-pyridinyl]-3-[[3-(trifluoromethoxy)phenyl]amino]-1H-1,2,4-triazole-5-propanamide (E6)

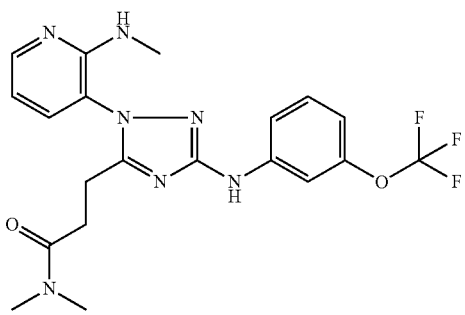 [SMILES: CNc1ncccc1-n1nc(Nc2cccc(OC(F)(F)F)c2)nc1CCC(=O)N(C)C]

A mixture of compound E76 (prepared according to Ex.3) (0.20 g, 0.00044 mol), CH$_3$NH$_2$ (2 g) and EtOH (20 ml) was stirred for 16 hours at 160° C. Subsequently, the solvent was evaporated and the residue was purified by reversed-phase high-performance liquid chromatography (Shandon Hyperprep® C$_{18}$ BDS (Base Deactivated Silica) 8 μm, 250 g, I.D. 5 cm). A gradient with 3 mobile phases was applied. Phase A: a 0.25% NH$_4$HCO$_3$ solution in water; phase B: MeOH; phase C: CH$_3$CN). The pure fractions were collected and the solvent was evaporated. The desired compound was dried. Yield: 0.091 g of compound E6 (yield: 46%).

Example 7

3-[[4-Fluoro-3-(trifluoromethyl)phenyl]amino]-1-(2-methyl-4-pyridinyl)-1H-1,2,4-triazole-5-propanol (E7)

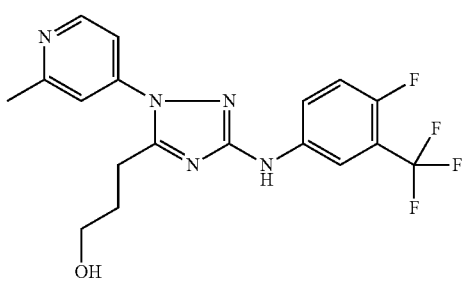 [SMILES: Cc1cc(-n2nc(Nc3ccc(F)c(C(F)(F)F)c3)nc2CCCO)ccn1]

LiAlH$_4$ (10.5 mmol) was added, portionwise, to an ice-cooled and stirred solution of compound E113 (prepared according to Description 14) (6.98 mmol) in Et$_2$O (80 ml) under an atmosphere of N$_2$. After 5 min., the mixture was allowed to warm to r.t. and was then stirred overnight. Subsequently, the reaction mixture was cooled to 0° C. and additional Et$_2$O (20.9 mmol) was added. After 5 min., the reaction mixture was warmed to r.t. Extra LiAlH$_4$ (3 equivalents; 21.0 mmol) was added to the cooled reaction mixture and the mixture was stirred for 1 hour. The reaction mixture was cooled and carefully quenched with 10% NaOH. Then the mixture was allowed to warm to r.t. and was filtered through a pad of diatomaceous earth. The filtrate was extracted with EtOAc. The combined organic extracts were washed with brine, dried (Na$_2$SO$_4$), filtered and concentrated to give 0.634 g of a yellow solid (yield=23%). The product was purified by reversed phase high-performance liquid chromatography (Shandon Hyperprep® C18 BDS (Base Deactivated Silica) 8 μm, 250 g, I.D. 5 cm). A gradient with 3 mobile phases was applied. Phase A: 90% of a 0.5% NH$_4$OAc solution in water+ 10% CH$_3$CN; phase B: MeOH; phase C: CH$_3$CN). The desired fractions were collected and the solvent was evaporated to yield a white solid. H$_2$O was added and the mixture was neutralized with saturated NaHCO$_3$. The contents were then extracted with DCM. The combined organic extracts were washed with brine, dried (Na$_2$SO$_4$), filtered and concentrated to give a white solid. Yield: 0.084 g of compound E7 (3%).

Examples 8 and 9

5-(3-Fluoropropyl)-N-[4-fluoro-3-(trifluoromethyl)phenyl]-1-(2-methyl-4-pyridinyl)-1H-1,2,4-triazol-3-amine (E8) and 5-(3-chloropropyl)-N-[4-fluoro-3-(trifluoromethyl)phenyl]-1-(2-methyl-4-pyridinyl)-1H-1,2,4-triazol-3-amine (E9)

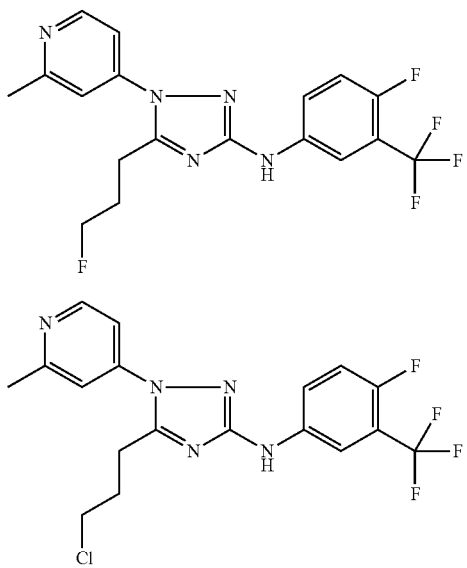

Methane sulfonylchloride (0.986 mol) was added dropwise to an ice-cooled and stirred suspension of compound E7 (prepared according to Ex.7) (0.493 mmol), N-ethyl-N-(1-methylethyl)-2-propanamine (0.986 mmol) and DMAP (0.049 mmol) in DCM (5 ml). After 5 min. the reaction mixture was allowed to warm to r.t. A saturated solution of NH$_4$Cl was added to the reaction mixture, followed by H$_2$O. The phases were separated. The aqueous phase was extracted with DCM. The combined organic extracts were washed with brine, then dried (Na$_2$SO$_4$), filtered and the solvent was evaporated to yield an orange oil. This oil was taken up in THF (5 ml) and cooled to 0° C. TBAF (1.0 M in THF) (2.50 mmol) was added and after 5-10 min., the reaction mixture was allowed to warm to r.t. The mixture was then stirred overnight. Additional TBAF (1.0 M in THF) (2.50 mmol) was added and the reaction mixture was heated at 50° C. for 2 hours. The solvent was removed under reduced pressure and the residue was partitioned between H$_2$O and DCM. The layers were separated. The aqueous phase was extracted with DCM and the combined organic extracts were washed, dried (Na$_2$SO$_4$), filtered and concentrated to give an orange oil. This oil was first purified by flash chromatography (Biotage; 40M column; eluent: DCM/MeOH gradient elution from 100/0 to 90/10. The material obtained was further purified by reversed-phase high-performance liquid chromatography (Shandon Hyperprep®C18 BDS (Base Deactivated Silica) 8 μm, 250 g, I.D. 5 cm). A gradient with 2 mobile phases was applied. Phase A: a 0.25% NH$_4$HCO$_3$ solution in water; phase B: CH$_3$CN). The desired fractions were collected and worked-up. Yield: 13 mg of compound E8 and 36 mg of compound E9 (6.6% and 17.7% respectively).

Example 10

3-[[4-Fluoro-3-(trifluoromethyl)phenyl]amino]-alpha-methyl-1-(2-methyl-4-pyridinyl)-, (alphaS)-1H-1,2,4-triazole-5-ethanol (E10)

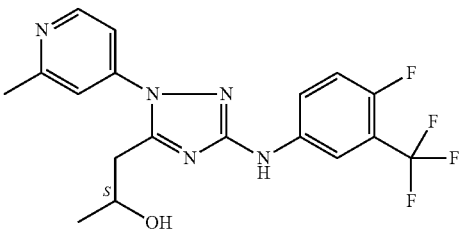

TBAF (16.3 ml; 16.3 mmol; 1.0 M in THF) was added to an ice-cooled and stirred suspension of intermediate D14 (prepared according to Description D.14) (4.1 g; 6.5 mmol) in THF (60 ml). After 5 min., the ensuing reaction mixture was allowed to warm to r.t. After 170 min. a saturated solution of NH$_4$Cl was added and the mixture was extracted with EtOAc. The combined organic extracts were washed with brine, dried (Na$_2$SO$_4$), filtered and concentrated to give an orange oil. This material was first purified by flash chromatography (Biotage; 40M column; eluent: DCM/MeOH gradient elution from 100/0 to 90/10. The desired fractions were collected and the solvent was evaporated to yield a yellow oily solid. This material was taken up in MeOH/DCM. This mixture was filtered and the filtrate was concentrated under reduced pressure to yield 1.251 g of a yellow oily solid. The product was further purified by reversed-phase high-performance liquid chromatography (Shandon Hyperprep® C$_{18}$ BDS (Base Deactivated Silica) 8 μm, 250 g, I.D. 5 cm). A gradient with 2 mobile phases was applied. Phase A: a 0.25% NH$_4$HCO$_3$ solution in water; phase B: CH$_3$CN). The desired fractions were collected to give (after evaporation of solvent) a cream powder. Yield: 357 mg of compound EN (13.9%).

Example 11

N-[4-Fluoro-3-(trifluoromethyl)phenyl]-1-(2-methyl-4-pyridinyl)-5-[(1E)-1-propenyl]-1H-1,2,4-triazol-3-amine (E11)

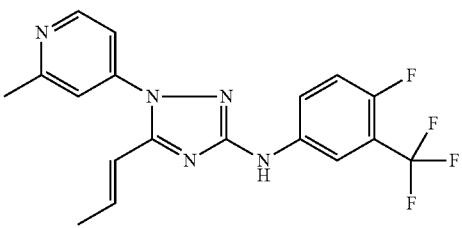 [SMILES: C/C=C/c1nc(Nc2ccc(F)c(C(F)(F)F)c2)nn1-c1ccnc(C)c1]

DIAD (0.3 ml; 1.5 mmol) was added dropwise to an ice-cooled and stirred solution of compound E10 (prepared according to Ex.10) (121 mg; 0.3 mmol), p-nitrobenzoic acid (230.2 mg; 1.4 mmol) and triphenylphosphine (401.4 mg; 1.5 mmol) in THF (6 ml) (under N$_2$ atmosphere). The reaction mixture was allowed to warm to r.t. over 1 hour and was then stirred overnight at r.t. The solvent was removed under reduced pressure to give a yellow oil. This material was purified by flash chromatography (Biotage; 40M column; eluent: DCM/MeOH gradient elution from 100/0 to 90/10. The desired fractions were combined to yield a pale yellow oily solid. This material was stirred in DIPE for several hours. Then the mixture was filtered and the precipitated solid was washed with DIPE and DCM to give a fine cream powder. Yield: 92 mg of compound E11 (79.7%).

Example 12

1-(3-Chloro-4-pyridinyl)-N-[4-fluoro-3-(trifluoromethyl)phenyl]-5-(3-methoxypropyl)-1H-1,2,4-triazol-3-amine (E12)

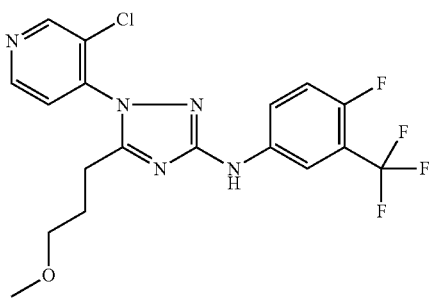 [SMILES: COCCCc1nc(Nc2ccc(F)c(C(F)(F)F)c2)nn1-c1ccncc1Cl]

Methane sulfonyl chloride (0.050 ml; 0.646 mmol) was added dropwise, to an ice-cooled and stirred suspension of E14 (prepared according to Ex. 7) (0.111 g; 0.258 mmol), N,N-diethylethanamine (0.090 ml; 0.646 mmol) and DMAP (0.003 g; 0.026 mmol) in DCM (2.5 ml). After 5 to 10 minutes the reaction mixture was allowed to warm to room temperature. After 2.5 hours LCMS showed mesylate and no remaining starting material. A saturated solution of NH$_4$Cl was added to the reaction mixture, followed by water. The aqueous phase was extracted with DCM and the combined organic extracts were washed with brine, dried (Na$_2$SO$_4$), filtered and concentrated to give an orange oil. The oil was taken up in NaOMe (5 ml) and the resulting solution stirred overnight at room temperature. Additional NaOMe (5 ml) was added and the reaction mixture was heated at 50° C. for 2 hours. The reaction mixture was cooled and a saturated solution of NH$_4$Cl was added, followed by water and the phases separated. The aqueous phase was extracted with DCM and the combined organic extracts were washed with brine, then dried (Na$_2$SO$_4$), filtered and concentrated to give a pale yellow oil. The residue was purified by chromatography on the Biotage System, eluent DCM to 10% MeOH/DCM. The combined relevant fractions gave a yellow oil and were purified by RP chromatography to give a cream solid. Yield: 22 mg of compound E12 (100%).

Example 137

(alphaS)-alpha-Ethyl-3-[[3-methoxy-5-(trifluoromethyl)phenyl]amino]-1-(2-methyl-4-pyridinyl)-1H-1,2,4-triazole-5-ethanol (E137)

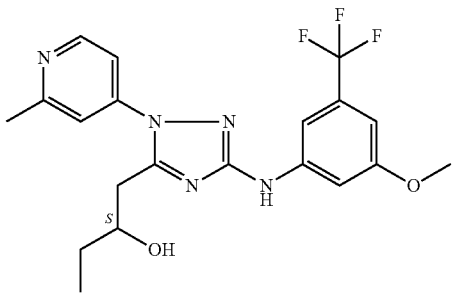

TBAF (57.4 ml; 57.4 mmol; 1.0 M in THF) was added to a stirred solution of intermediate D18 (prepared according to Description D.18) (12.6 g; 19.1 mmol) in THF (200 ml). The mixture was stirred for 24 hours. A saturated solution of NH$_4$Cl was added and the mixture was stirred for another 5 to 10 minutes. The mixture was extracted with EtOAc (×3). The combined organic extracts were washed with water (×5) until most of the TBAF was gone, then washed with brine, dried (Na$_2$SO$_4$), filtered and concentrated under reduced pressure to give an amber oil. This material was purified by flash chromatography using the Flash-master and Biotage systems, eluent: DCM to 5% CH$_3$OH/DCM, gradient elution from 100/0 to 90/10, and the relevant fractions were combined to give a cream powder. Yield: 1.3 g of compound E137 (16.1%).

Example 257

N-Cyclopropyl-1-(2,6-dimethyl-4-pyridinyl)-3-[[2-fluoro-3-(trifluoromethyl)phenyl]amino]-1H-1,2,4-triazole-5-acetamide (E257)

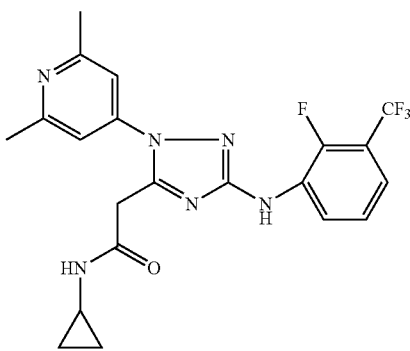 [SMILES: Cc1cc(-n2nc(Nc3cccc(C(F)(F)F)c3F)nc2CC(=O)NC2CC2)cc(C)n1]

Cyclopropylamine (5 ml) was added to a stirred suspension of intermediate D21 (prepared according to D21) (1.41 mmol) in MeOH (5 ml) and the ensuing reaction mixture stirred at 40° C. overnight. The reaction mixture was concentrated under reduced pressure to give a pale yellow/cream powder. This material was crystallised from MeCN (product dissolves at 80° C.), then the contents filtered and dried to give a fluffy white powder. Yield: 527 mg of compound E257 (83%).

Tables 1 and 2 lists compounds of Formula (I) that were prepared according to one of the above Examples.

TABLE 1

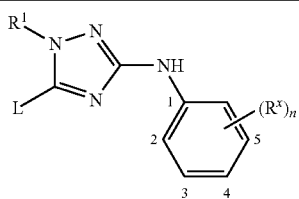

| Co. No. | Exp No. | R¹ | L | Rˣ |
|---|---|---|---|---|
| E11 | Ex. 11 | 2-methylpyridin-4-yl (CH₃ on pyridine N-adjacent carbon) | (E)-CH₃-CH=CH- | 3-CF$_3$, 4-F |
| E16 | Ex. 7 | 2-methylpyridin-4-yl | HO-CH₂-CH₂- | 3-CF$_3$, 4-F |
| E13 | D. 14 | 2-methylpyridin-4-yl | H₃C-O-CH₂-CH₂- | 3-CF$_3$, 4-F |
| E9 | Ex. 9 | 2-methylpyridin-4-yl | Cl-CH₂-CH₂-CH₂- | 3-CF$_3$, 4-F |
| E8 | Ex. 8 | 2-methylpyridin-4-yl | F-CH₂-CH₂-CH₂- | 3-CF$_3$, 4-F |
| E7 | Ex. 7 | 2-methylpyridin-4-yl | HO-CH₂-CH₂-CH₂- | 3-CF$_3$, 4-F |
| E14 | Ex. 7 | 3-chloropyridin-4-yl | HO-CH₂-CH₂-CH₂- | 3-CF$_3$, 4-F |
| E15 | D. 14 | 2-methylpyridin-4-yl | H₃C-O-CH₂-CH₂-CH₂- | 3-CF$_3$, 4-F |
| E12 | Ex. 12 | 3-chloropyridin-4-yl | H₃C-O-CH₂-CH₂-CH₂- | 3-CF$_3$, 4-F |

TABLE 1-continued
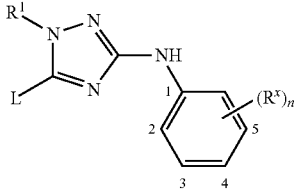
| Co. No. | Exp No. | R¹ | L | Rˣ |
|---|---|---|---|---|
| E17 | Ex. 10 | 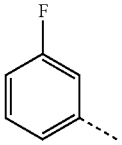 | 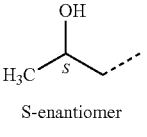 S-enantiomer | 3-F, 4-F |
| E18 | Ex. 10 | 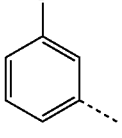 | 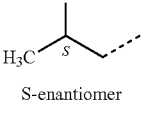 S-enantiomer | 3-CF₃, 4-F |
| E19 | Ex. 10 | 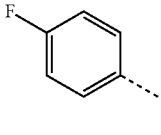 | 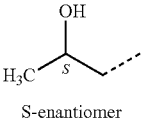 S-enantiomer | 3-F, 4-F |
| E20 | Ex. 10 | 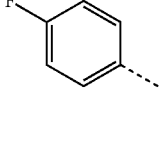 | 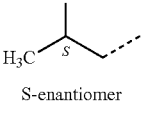 S-enantiomer | 3-CF₃, 4-F |
| E21 | Ex. 10 | 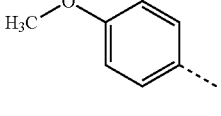 | 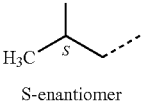 S-enantiomer | 3-F, 4-F |
| E22 | Ex. 10 | 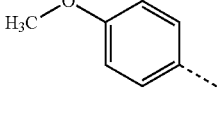 | 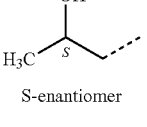 S-enantiomer | 3-CF₃, 4-F |
| E146 | Ex. 10 | 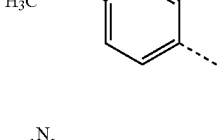 | 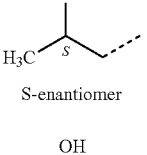 S-enantiomer | 3-OCH₃, 5-CF₃ |
| E144 | Ex. 10 | 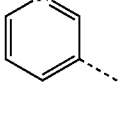 | 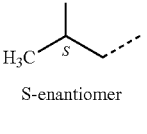 S-enantiomer | 3-OCH₃, 5-CF₃ |
| E143 | Ex. 10 | 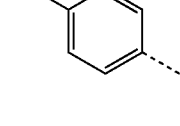 | 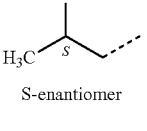 S-enantiomer | 3-OCH₃, 5-CF₃ |

TABLE 1-continued

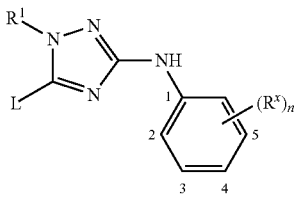

| Co. No. | Exp No. | R¹ | L | Rˣ |
|---|---|---|---|---|
| E23 | Ex. 10 | 2-methylpyridin-4-yl (CH₃ at 2-position) | (S)-1-hydroxy-1-methylethyl group, S-enantiomer | 3-Cl |
| E24 | Ex. 10 | 2-methylpyridin-4-yl | S-enantiomer | 3-F, 4-F |
| E198 | Ex. 10 | 2-methylpyridin-4-yl | R-enantiomer | 3-F, 4-F |
| E10 | Ex. 10 | 2-methylpyridin-4-yl | S-enantiomer | 3-CF₃, 4-F |
| E126 | Ex. 10 | 2-methylpyridin-4-yl | R-enantiomer | 3-CF₃, 4-F |
| E135 | Ex. 10 | 2-methylpyridin-4-yl | S-enantiomer | 3-CF₃, 5-OCH₃ |
| E277 | Ex. 10 | 2-methylpyridin-4-yl | S-enantiomer | 2-F, 3-F, 4-F |
| E207 | Ex. 10 | 2-methylpyridin-4-yl | S-enantiomer | 3-F, 4-F, 5-F |

TABLE 1-continued

| Co. No. | Exp No. | R¹ | L | Rˣ |
|---|---|---|---|---|
| E141 | Ex. 10 | 2,6-dimethylpyridin-4-yl | CH(OH)CH₃ (S-enantiomer, with CH₃ on α-carbon) | 3-F, 4-F |
| E197 | Ex. 10 | 2,6-dimethylpyridin-4-yl | CH(OH)CH₃ (R-enantiomer) | 3-F, 4-F |
| E148 | Ex. 137 | 2,6-dimethylpyridin-4-yl | CH(OH)CH₂CH₃ (S-enantiomer) | 3-CF₃, 4-F |
| E199 | Ex. 10 | 2,6-dimethylpyridin-4-yl | CH(OH)CH₃ (R-enantiomer) | 3-CF₃, 4-F |
| E189 | Ex. 10 | 2,6-dimethylpyridin-4-yl | CH(OH)CH₃ (S-enantiomer) | 2-F, 3-F, 4-F |
| E194 | Ex. 10 | 2,6-dimethylpyridin-4-yl | CH(OH)CH₃ (S-enantiomer) | 2-F, 4-F, 5-F |
| E208 | Ex. 10 | 2,6-dimethylpyridin-4-yl | CH(OH)CH₃ (S-enantiomer) | 3-F, 4-F, 5-F |
| E131 | Ex. 10 | 2-ethylpyridin-4-yl | CH(OH)CH₃ (S-enantiomer) | 3-F, 4-F |

TABLE 1-continued
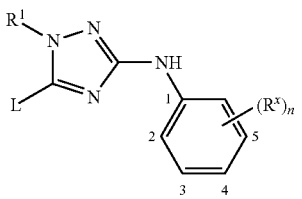
| Co. No. | Exp No. | R¹ | L | Rˣ |
|---|---|---|---|---|
| E133 | Ex. 10 |  H₃C-CH₂-pyridin-4-yl | 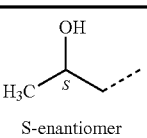 H₃C-CH(OH)-CH₂- S-enantiomer | 3-CF₃, 5-OCH₃ |
| E25 | Ex. 10 | 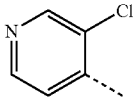 3-Cl-pyridin-4-yl | 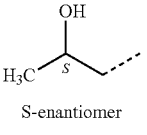 S-enantiomer | 3-CF₃, 4-F |
| E26 | Ex. 10 | 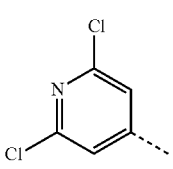 2,6-diCl-pyridin-4-yl | 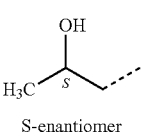 S-enantiomer | 3-CF₃, 4-F |
| E27 | Ex. 10 | 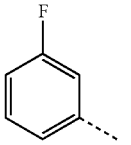 3-F-phenyl | 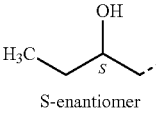 S-enantiomer | 3-F, 4-F |
| E28 | Ex. 10 | 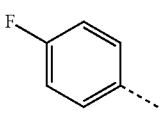 4-F-phenyl | 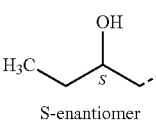 S-enantiomer | 3-F, 4-F |
| E29 | Ex. 10 | 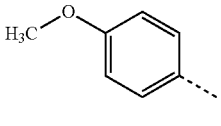 4-OCH₃-phenyl | 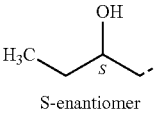 S-enantiomer | 3-F, 4-F |
| E149 | Ex. 10 | 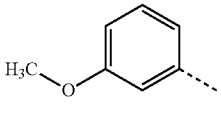 3-OCH₃-phenyl | 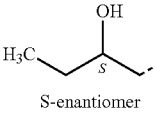 S-enantiomer | 3-F, 4-F |
| E139 | Ex. 10 | 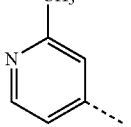 2-CH₃-pyridin-4-yl | 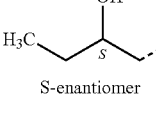 S-enantiomer | 3-Cl |
| E204 | Ex. 137 | 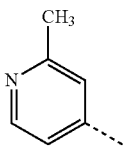 2-CH₃-pyridin-4-yl | 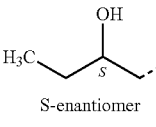 S-enantiomer | 3-CF₃ |

TABLE 1-continued

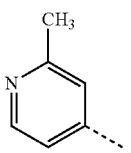

| Co. No. | Exp No. | R¹ | L | Rˣ |
|---|---|---|---|---|
| E202 | Ex. 137 | 2-methylpyridin-4-yl | (S)-1-hydroxybutyl, S-enantiomer | 4-OCH₃ |
| E173 | Ex. 137 | 2-methylpyridin-4-yl | (S)-1-hydroxybutyl, S-enantiomer | 2-F, 3-Cl |
| E30 | Ex. 10 | 2-methylpyridin-4-yl | (S)-1-hydroxybutyl, S-enantiomer | 3-F, 4-F |
| E134 | Ex. 10 | 2-methylpyridin-4-yl | (R)-1-hydroxybutyl, R-enantiomer | 3-F, 4-F |
| E147 | Ex. 137 | 2-methylpyridin-4-yl | (S)-1-hydroxybutyl, S-enantiomer | 3-CF₃, 4-F |
| E206 | Ex. 137 | 2-methylpyridin-4-yl | (S)-1-hydroxybutyl, S-enantiomer | 3-Cl, 5-OCH₃ |
| E186 | Ex. 137 | 2-methylpyridin-4-yl | (S)-1-hydroxybutyl, S-enantiomer | 3-F, 5-OCH₃ |
| E137 | Ex. 137 | 2-methylpyridin-4-yl | (S)-1-hydroxybutyl, S-enantiomer | 3-CF₃, 5-OCH₃ |

TABLE 1-continued

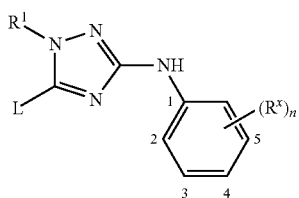

| Co. No. | Exp No. | R¹ | L | Rˣ |
|---|---|---|---|---|
| E130 | Ex. 10 | 2-methylpyridin-4-yl | (S)-1-hydroxybutan-2-yl (S-enantiomer) | 2-F, 3-F, 4-F |
| E187 | Ex. 137 | 2-methylpyridin-4-yl | (S)-1-hydroxybutan-2-yl (S-enantiomer) | 3-F, 4-F, 5-F |
| E138 | Ex. 10 | 2-ethylpyridin-4-yl | (S)-1-hydroxybutan-2-yl (S-enantiomer) | 3-F, 4-F |
| E220 | Ex. 137 | 2,3-dimethylpyridin-4-yl | (S)-1-hydroxybutan-2-yl (S-enantiomer) | 3-OCH₃, 5-CF₃ |
| E129 | Ex. 10 | 2,6-dimethylpyridin-4-yl | (S)-1-hydroxybutan-2-yl (S-enantiomer) | 3-Cl |
| E203 | Ex. 137 | 2,6-dimethylpyridin-4-yl | (S)-1-hydroxybutan-2-yl (S-enantiomer) | 4-OCH₃ |
| E172 | Ex. 137 | 2,6-dimethylpyridin-4-yl | (S)-1-hydroxybutan-2-yl (S-enantiomer) | 2-F, 3-Cl |
| E132 | Ex. 10 | 2,6-dimethylpyridin-4-yl | (S)-1-hydroxybutan-2-yl (S-enantiomer) | 3-F, 4-F |

TABLE 1-continued

| Co. No. | Exp No. | R¹ | L | Rˣ |
|---|---|---|---|---|
| E205 | Ex. 137 | 2,6-dimethylpyridin-4-yl | (S)-1-hydroxypropyl (S-enantiomer) | 3-Cl, 5-OCH₃ |
| E190 | Ex. 137 | 2,6-dimethylpyridin-4-yl | (S)-1-hydroxypropyl (S-enantiomer) | 3-F, 5-OCH₃ |
| E128 | Ex. 10 | 2,6-dimethylpyridin-4-yl | (R)-1-hydroxypropyl (R-enantiomer) | 3-OCH₃, 5-CF₃ |
| E276 | Ex. 10 | 2,6-dimethylpyridin-4-yl | (S)-1-hydroxypropyl (S-enantiomer) | 3-OCH₃, 5-CF₃ |
| E127 | Ex. 10 | 2,6-dimethylpyridin-4-yl | (S)-1-hydroxypropyl (S-enantiomer) | 2-F, 3-F, 4-F |
| E188 | Ex. 137 | 2,6-dimethylpyridin-4-yl | (S)-1-hydroxypropyl (S-enantiomer) | 3-F, 4-F, 5-F |
| E136 | Ex. 6 | N-methyl-(pyridin-2-yl)aminomethyl | (S)-1-hydroxypropyl (S-enantiomer) | 3-F, 4-F |
| E145 | Ex. 137 | pyridin-3-yl | (S)-1-hydroxypropyl (S-enantiomer) | 3-F, 4-F |

TABLE 1-continued
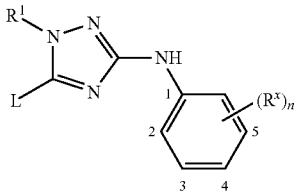
| Co. No. | Exp No. | R¹ | L | Rˣ |
|---|---|---|---|---|
| E196 | Ex. 137 | 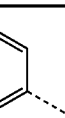 | 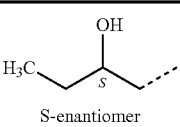<br>S-enantiomer | 3-Cl |
| E140 | Ex. 137 | 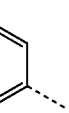 | 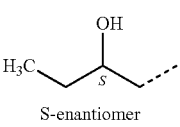<br>S-enantiomer | 3-F, 4-F |
| E142 | Ex. 137 | 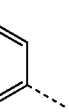 | 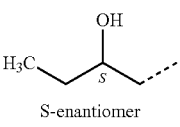<br>S-enantiomer | 3-OCH₃, 5-CF₃ |
| E195 | Ex. 137 | 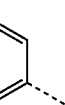 | 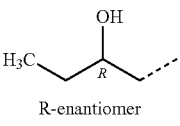<br>R-enantiomer | 3-OCH₃, 5-CF₃ |
| E31 | Ex. 7 |  | 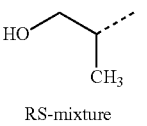<br>RS-mixture | 3-CF₃, 4-F |
| E32 | D. 14 |  | 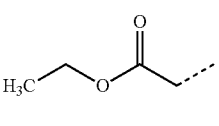 | 3-CF₃, 4-F |
| E33 | D. 14 | 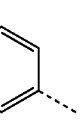 | 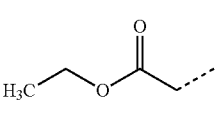 | 3-F, 4-F |
| E34 | D. 14 |  | 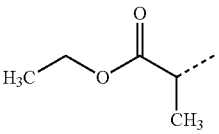 | 3-CF₃, 4-F |
| E35 | Ex. 2 |  | 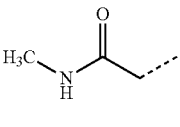 | 3-CF₃, 4-F |

TABLE 1-continued

| Co. No. | Exp No. | R¹ | L | Rˣ |
|---|---|---|---|---|
| E255 | Ex. 2 | 2,6-dimethylpyridin-4-yl | -NH-C(O)-CH₂- (N-methyl) | 2-F, 3-CF₃ |
| E259 | Ex. 2 | 2,6-dimethylpyridin-4-yl | -NH-C(O)-CH₂- (N-methyl) | 2-F, 5-CF₃ |
| E249 | Ex. 2 | 2,6-dimethylpyridin-4-yl | -NH-C(O)-CH₂- (N-methyl) | 3-Cl, 4-F |
| E223 | Ex. 2 | 2,6-dimethylpyridin-4-yl | -NH-C(O)-CH₂- (N-methyl) | 3-CF₃, 4-F |
| E245 | Ex. 2 | 2,6-dimethylpyridin-4-yl | -NH-C(O)-CH₂- (N-methyl) | 3-Cl, 5-F |
| E232 | Ex. 2 | 2,6-dimethylpyridin-4-yl | -NH-C(O)-CH₂- (N-methyl) | 3-F, 5-F |
| E251 | Ex. 2 | 2,6-dimethylpyridin-4-yl | -NH-C(O)-CH₂- (N-methyl) | 3-F, 5-CF₃ |
| E216 | Ex. 2 | 2,6-dimethylpyridin-4-yl | -NH-C(O)-CH₂- (N-methyl) | 3-Cl, 5-OCH₃ |

TABLE 1-continued

| Co. No. | Exp No. | R¹ | L | Rˣ |
|---|---|---|---|---|
| E243 | Ex. 2 | 2,6-dimethylpyridin-4-yl | -N(CH₃)C(O)CH₂- | 3-OCH₃, 5-CF₃ |
| E227 | Ex. 2 | 2,6-dimethylpyridin-4-yl | -N(CH₃)C(O)CH₂- | 3-CF₃, 4-OCH₃ |
| E209 | Ex. 2 | 2,6-dimethylpyridin-4-yl | -N(CH₃)C(O)CH₂- | 2-F, 3-F, 4-F |
| E240 | Ex. 2 | 2,6-dimethylpyridin-4-yl | -N(CH₃)C(O)CH₂- | 3-F, 4-F, 5-F |
| E36 | Ex. 2 | 2,3-dihydro-1,4-benzodioxin-6-yl | -N(CH₃)C(O)CH₂- | 3-F, 4-F |
| E37 | Ex. 2 | 2-methylpyridin-4-yl | -N(CH₃)C(O)CH(CH₃)- RS-mixture | 3-CF₃, 4-F |
| E171 | Ex. 2 | 2,6-dimethylpyridin-4-yl | -NH(cyclopropyl)C(O)CH₂- | 3-CF₃ |
| E182 | Ex. 2 | 2,6-dimethylpyridin-4-yl | -NH(cyclopropyl)C(O)CH₂- | 3-OCF₃ |

TABLE 1-continued

| Co. No. | Exp No. | R¹ | L | Rˣ |
|---|---|---|---|---|
| E150 | Ex. 2 | 2,6-dimethylpyridin-4-yl | N-cyclopropyl propanamide | 2-F, 3-Cl |
| E257 | Ex. 2 | 2,6-dimethylpyridin-4-yl | N-cyclopropyl propanamide | 2-F, 3-CF₃ |
| E261 | Ex. 2 | 2,6-dimethylpyridin-4-yl | N-cyclopropyl propanamide | 2-F, 5-CF₃ |
| E230 | Ex. 2 | 2,6-dimethylpyridin-4-yl | N-cyclopropyl propanamide | 3-Cl, 4-F |
| E168 | Ex. 2 | 2,6-dimethylpyridin-4-yl | N-cyclopropyl propanamide | 3-F, 4-F |
| E226 | Ex. 2 | 2,6-dimethylpyridin-4-yl | N-cyclopropyl propanamide | 3-CF₃, 4-F |
| E229 | Ex. 2 | 2,6-dimethylpyridin-4-yl | N-cyclopropyl propanamide | 3-CF₃, 4-OCH₃ |
| E247 | Ex. 2 | 2,6-dimethylpyridin-4-yl | N-cyclopropyl propanamide | 3-Cl, 5-F |

TABLE 1-continued
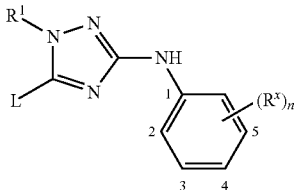
| Co. No. | Exp No. | R¹ | L | Rˣ |
|---|---|---|---|---|
| E238 | Ex. 2 | 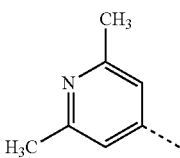 | 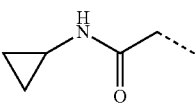 | 3-F, 5-F |
| E253 | Ex. 2 | 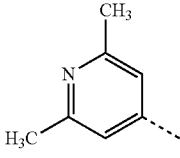 | 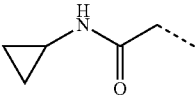 | 3-F, 5-CF₃ |
| E221 | Ex. 2 | 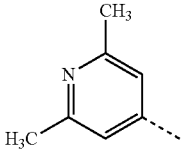 | 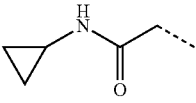 | 3-Cl, 5-OCH₃ |
| E217 | Ex. 2 | 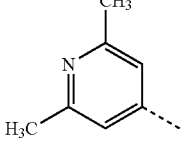 | 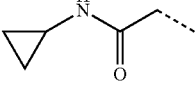 | 3-OCH₃, 5-CF₃ |
| E211 | Ex. 2 | 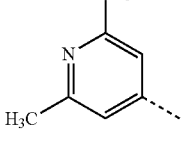 | 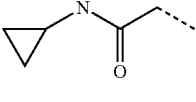 | 2-F, 3-F, 4-F |
| E241 | Ex. 2 | 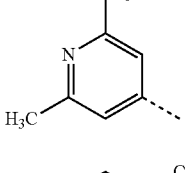 | 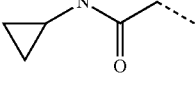 | 3-F, 4-F, 5-F |
| E157 | Ex. 2 | 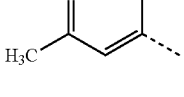 | 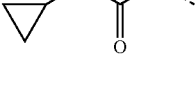 | 2-F, 3-Cl |
| E192 | Ex. 2 | 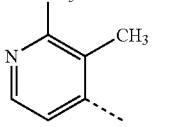 | 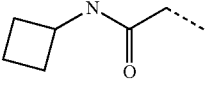 | 2-F, 3-Cl |

TABLE 1-continued

| Co. No. | Exp No. | R¹ | L | Rˣ |
|---|---|---|---|---|
| E174 | Ex. 2 | 2,6-dimethylpyridin-4-yl | N-cyclobutyl propanamide linker | 3-CF₃ |
| E184 | Ex. 2 | 2,6-dimethylpyridin-4-yl | N-cyclobutyl propanamide linker | 3-OCF₃ |
| E152 | Ex. 2 | 2,6-dimethylpyridin-4-yl | N-cyclobutyl propanamide linker | 2-F, 3-Cl |
| E258 | Ex. 2 | 2,6-dimethylpyridin-4-yl | N-cyclobutyl propanamide linker | 2-F, 3-CF₃ |
| E262 | Ex. 2 | 2,6-dimethylpyridin-4-yl | N-cyclobutyl propanamide linker | 2-F, 5-CF₃ |
| E231 | Ex. 2 | 2,6-dimethylpyridin-4-yl | N-cyclobutyl propanamide linker | 3-Cl, 4-F |
| E169 | Ex. 2 | 2,6-dimethylpyridin-4-yl | N-cyclobutyl propanamide linker | 3-F, 4-F |
| E225 | Ex. 2 | 2,6-dimethylpyridin-4-yl | N-cyclobutyl propanamide linker | 3-CF₃, 4-F |

TABLE 1-continued
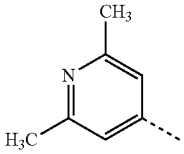
| Co. No. | Exp No. | R¹ | L | Rˣ |
|---|---|---|---|---|
| E236 | Ex. 2 | 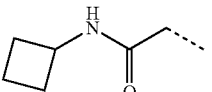 | 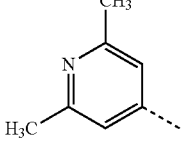 | 3-CF₃, 4-OCH₃ |
| E248 | Ex. 2 | 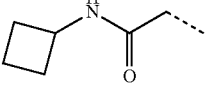 | 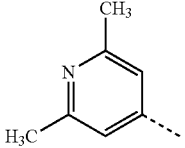 | 3-Cl, 5-F |
| E239 | Ex. 2 | 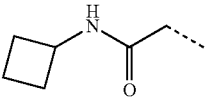 | 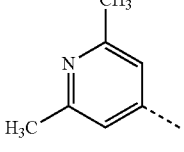 | 3-F, 5-F |
| E254 | Ex. 2 | 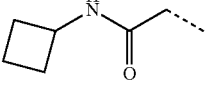 | 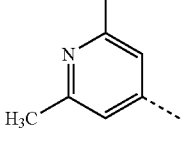 | 3-F, 5-CF₃ |
| E222 | Ex. 2 | 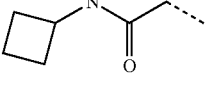 | 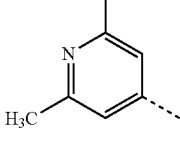 | 3-Cl, 5-OCH₃ |
| E244 | Ex. 2 | 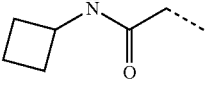 | 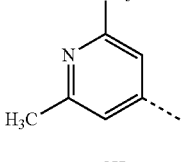 | 3-OCH₃, 5-CF₃ |
| E212 | Ex. 2 | 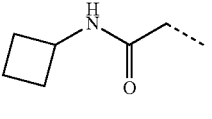 | 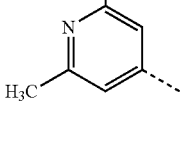 | 2-F, 3-F, 4-F |
| E242 | Ex. 2 | 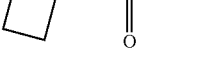 | | 3-F, 4-F, 5-F |

TABLE 1-continued

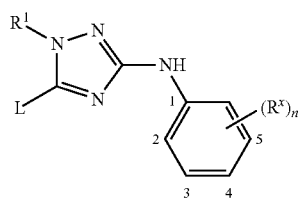

| Co. No. | Exp No. | R¹ | L | Rˣ |
|---|---|---|---|---|
| E159 | Ex. 2 | 2,5-dimethylpyridin-4-yl | N-cyclobutyl propanamide | 2-F, 3-Cl |
| E162 | Ex. 2 | 2,5-dimethylpyridin-4-yl | N-cyclobutyl propanamide | 3-F, 4-F |
| E191 | Ex. 2 | 2,3-dimethylpyridin-4-yl | N-ethyl propanamide | 2-F, 3-Cl |
| E175 | Ex. 2 | 2,6-dimethylpyridin-4-yl | N-ethyl propanamide | 3-CF₃ |
| E181 | Ex. 2 | 2,6-dimethylpyridin-4-yl | N-ethyl propanamide | 3-OCF₃ |
| E153 | Ex. 2 | 2,6-dimethylpyridin-4-yl | N-ethyl propanamide | 2-F, 3-Cl |
| E256 | Ex. 2 | 2,6-dimethylpyridin-4-yl | N-ethyl propanamide | 2-F, 3-CF₃ |
| E260 | Ex. 2 | 2,6-dimethylpyridin-4-yl | N-ethyl propanamide | 2-F, 5-CF₃ |

TABLE 1-continued
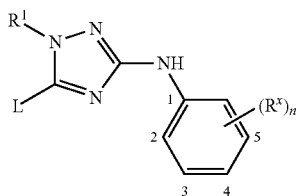
| Co. No. | Exp No. | R¹ | L | Rˣ |
|---|---|---|---|---|
| E250 | Ex. 2 | 2,6-dimethylpyridin-4-yl | -CH(NHEt)C(O)- | 3-Cl, 4-F |
| E167 | Ex. 2 | 2,6-dimethylpyridin-4-yl | -CH(NHEt)C(O)- | 3-F, 4-F |
| E224 | Ex. 2 | 2,6-dimethylpyridin-4-yl | -CH(NHEt)C(O)- | 3-CF₃, 4-F |
| E228 | Ex. 2 | 2,6-dimethylpyridin-4-yl | -CH(NHEt)C(O)- | 3-CF₃, 4-OCH₃ |
| E246 | Ex. 2 | 2,6-dimethylpyridin-4-yl | -CH(NHEt)C(O)- | 3-Cl, 5-F |
| E237 | Ex. 2 | 2,6-dimethylpyridin-4-yl | -CH(NHEt)C(O)- | 3-F, 5-F |
| E252 | Ex. 2 | 2,6-dimethylpyridin-4-yl | -CH(NHEt)C(O)- | 3-F, 5-CF₃ |
| E219 | Ex. 2 | 2,6-dimethylpyridin-4-yl | -CH(NHEt)C(O)- | 3-Cl, 5-OCH₃ |

TABLE 1-continued

| Co. No. | Exp No. | R¹ | L | Rˣ |
|---|---|---|---|---|
| E218 | Ex. 2 | 2,6-dimethylpyridin-4-yl | -C(=O)NH-CH₂CH₃ (ethyl) | 3-OCH₃, 5-CF₃ |
| E210 | Ex. 2 | 2,6-dimethylpyridin-4-yl | -C(=O)NH-CH₂CH₃ | 2-F, 3-F, 4-F |
| E215 | Ex. 2 | 2,6-dimethylpyridin-4-yl | -C(=O)NH-CH₂CH₃ | 3-F, 4-F, 5-F |
| E156 | Ex. 2 | 5-methyl-2-methylpyridin-4-yl | -C(=O)NH-CH₂CH₃ | 2-F, 3-Cl |
| E164 | Ex. 2 | 5-methyl-2-methylpyridin-4-yl | -C(=O)NH-CH₂CH₃ | 3-F, 4-F |
| E213 | Ex. 2 | 2,6-dimethylpyridin-4-yl | -C(=O)NH-CH(CH₃)₂ | 2-F, 3-F, 4-F |
| E193 | Ex. 2 | 2,3-dimethylpyridin-4-yl | -C(=O)NH-CH₂-cyclopropyl | 2-F, 3-Cl |
| E177 | Ex. 2 | 2,6-dimethylpyridin-4-yl | -C(=O)NH-CH₂-cyclopropyl | 3-CF₃ |

TABLE 1-continued

| Co. No. | Exp No. | R¹ | L | Rˣ |
|---|---|---|---|---|
| E165 | Ex. 2 | 2,6-dimethylpyridin-4-yl | cyclopropylmethyl-NH-C(O)- | 3-OCF₃ |
| E154 | Ex. 2 | 2,6-dimethylpyridin-4-yl | cyclopropylmethyl-NH-C(O)- | 2-F, 3-Cl |
| E185 | Ex. 2 | 2,6-dimethylpyridin-4-yl | cyclopropylmethyl-NH-C(O)- | 3-F, 4-F |
| E214 | Ex. 2 | 2,6-dimethylpyridin-4-yl | cyclopropylmethyl-NH-C(O)- | 2-F, 3-F, 4-F |
| E158 | Ex. 2 | 2,5-dimethylpyridin-4-yl | cyclopropylmethyl-NH-C(O)- | 2-F, 3-Cl |
| E166 | Ex. 2 | 2,5-dimethylpyridin-4-yl | cyclopropylmethyl-NH-C(O)- | 3-F, 4-F |
| E38 | Ex. 2 | 2-chlorophenyl | CH₃-NH-C(O)-CH₂- | 3-F, 4-F |
| E39 | Ex. 2 | 3-chlorophenyl | CH₃-NH-C(O)-CH₂- | 3-F, 4-F |
| E40 | Ex. 2 | 4-chlorophenyl | CH₃-NH-C(O)-CH₂- | 3-F, 4-F |

TABLE 1-continued

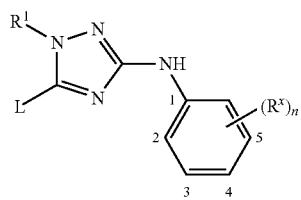

| Co. No. | Exp No. | R¹ | L | Rˣ |
|---|---|---|---|---|
| E41 | Ex. 2 | 3-methoxyphenyl | -CH₂CH₂C(O)N(CH₃)- | 3-OCF₃ |
| E42 | Ex. 2 | 3-methoxyphenyl | -CH₂CH₂C(O)N(CH₃)- | 3-CF₃, 4-F |
| E43 | Ex. 3 | 4-methoxyphenyl | -CH₂CH₂C(O)N(CH₃)- | 3-F, 4-F |
| E44 | Ex. 3 | 4-methoxyphenyl | -CH₂CH₂C(O)N(CH₃)- | 3-CF₃, 4-F |
| E45 | Ex. 3 | 3,4-dimethoxyphenyl | -CH₂CH₂C(O)N(CH₃)- | 3-F, 4-F |
| E46 | Ex. 3 | 3,4-dimethoxyphenyl | -CH₂CH₂C(O)N(CH₃)- | 3-CF₃, 4-F |
| E47 | Ex. 3 | 4-trifluoromethoxyphenyl | -CH₂CH₂C(O)N(CH₃)- | 3-F, 4-F |
| E48 | Ex. 3 | pyridin-3-yl | -CH₂CH₂C(O)N(CH₃)- | 3-F, 4-F |
| E49 | Ex. 3 | pyridin-3-yl | -CH₂CH₂C(O)N(CH₃)- | 3-CF₃, 4-F |

TABLE 1-continued

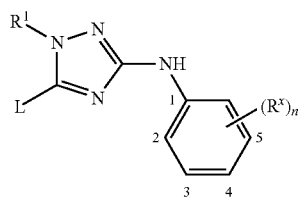

| Co. No. | Exp No. | R¹ | L | Rˣ |
|---|---|---|---|---|
| E50 | Ex. 3 | 3-pyridyl | -CH₂CH₂C(O)NHCH₃ | 3-OCF₃ |
| E51 | Ex. 2 | 6-methyl-3-pyridyl | -CH₂CH₂C(O)NHCH₃ | 3-OCF₃ |
| E52 | Ex. 3 | 4-pyridyl | -CH₂CH₂C(O)NHCH₃ | 3-F, 4-F |
| E53 | Ex. 3 | 4-pyridyl | -CH₂CH₂C(O)NHCH₃ | 3-OCF₃ |
| E54 | Ex. 2 | 2-methyl-4-pyridyl | -CH₂CH₂C(O)NHCH₃ | 3-OCF₃ |
| E2 | Ex. 2 | 2,3-dihydro-1,4-benzodioxin-6-yl | -CH₂CH₂C(O)NHCH₃ | 3-F, 4-F |
| E55 | Ex. 2 | 2,3-dihydro-1,4-benzodioxin-6-yl | -CH₂CH₂C(O)NHCH₃ | 3-CF₃, 4-F |
| E56 | Ex. 3 | 3-pyridyl | -CH₂CH₂C(O)NHCH(CH₃)₂ | 3-OCF₃ |
| E57 | Ex. 3 | 2-chlorophenyl | -CH₂CH₂C(O)N(CH₃)₂ | 3-F, 4-F |
| E58 | Ex. 3 | 3-chlorophenyl | -CH₂CH₂C(O)N(CH₃)₂ | 3-F, 4-F |

TABLE 1-continued
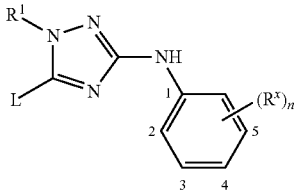
| Co. No. | Exp No. | R¹ | L | Rˣ |
|---|---|---|---|---|
| E59 | Ex. 3 | 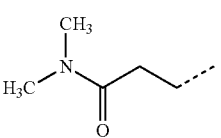 | 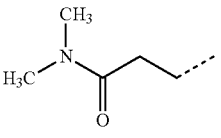 | 3-F, 4-F |
| E60 | Ex. 3 | 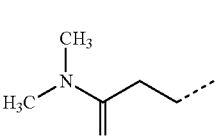 | 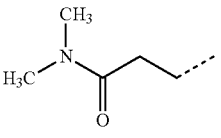 | 3-OCF₃ |
| E61 | Ex. 3 | 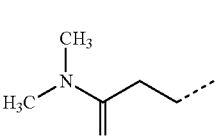 | 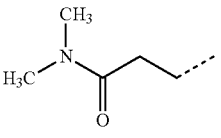 | 3-CF₃, 4-F |
| E183 | Ex. 3 | 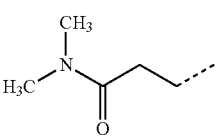 | 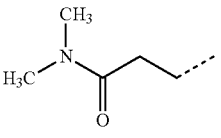 | 3-OCF₃ |
| E62 | Ex. 3 | 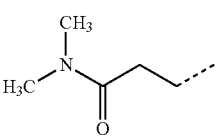 | 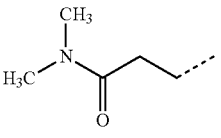 | 3-CF₃, 4-F |
| E63 | Ex. 3 | 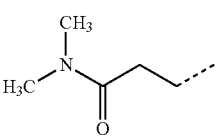 | 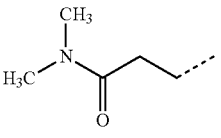 | 3-F, 4-F |
| E155 | Ex. 3 | 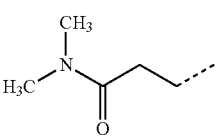 | 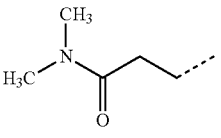 | 3-Br, 4-F, 5-F |
| E64 | Ex. 3 | 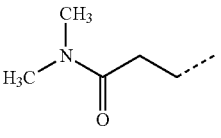 | 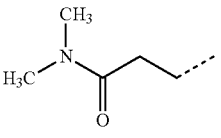 | 3-F, 4-F |

TABLE 1-continued
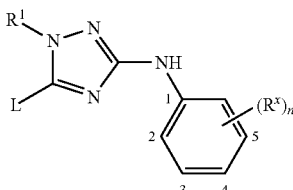
| Co. No. | Exp No. | R¹ | L | Rˣ |
|---|---|---|---|---|
| E65 | Ex. 3 | 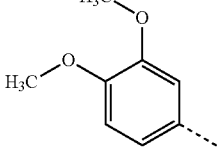 | 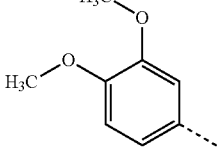 | 3-CF₃, 4-F |
| E66 | Ex. 3 |  | 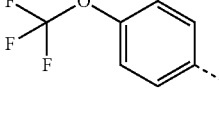 | 3-F, 4-F |
| E67 | Ex. 3 | 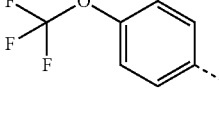 |  | 3-F, 4-F |
| E68 | Ex. 3 | 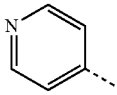 | 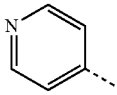 | 3-CF₃, 4-F |
| E69 | Ex. 3 |  | 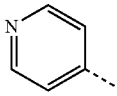 | 3-OCF₃ |
| E70 | Ex. 3 | 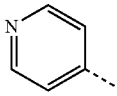 |  | 3-F, 4-F |
| E71 | Ex. 3 | 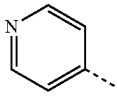 | 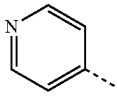 | 3-OCF₃ |
| E72 | Ex. 3 |  | 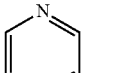 | 3-CF₃, 4-F |
| E73 | Ex. 3 | 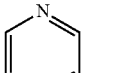 |  | 3-OCF₃ |

TABLE 1-continued

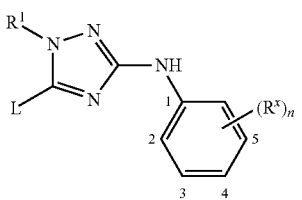

| Co. No. | Exp No. | R¹ | L | Rˣ |
|---|---|---|---|---|
| E266 | Ex. 3 | 2,6-dimethylpyridin-4-yl | N-methyl-N-methylpropanamide | 3-CF₃ |
| E267 | Ex. 3 | 2,6-dimethylpyridin-4-yl | N-methyl-N-methylpropanamide | 3-OCF₃ |
| E265 | Ex. 3 | 2,6-dimethylpyridin-4-yl | N-methyl-N-methylpropanamide | 2-F, 3-Cl |
| E279 | Ex. 3 | 2,6-dimethylpyridin-4-yl | N-methyl-N-methylpropanamide | 2-F, 5-CF₃ |
| E273 | Ex. 3 | 2,6-dimethylpyridin-4-yl | N-methyl-N-methylpropanamide | 3-Cl, 4-F |
| E234 | Ex. 3 | 2,6-dimethylpyridin-4-yl | N-methyl-N-methylpropanamide | 3-F, 4-F |
| E233 | Ex. 3 | 2,6-dimethylpyridin-4-yl | N-methyl-N-methylpropanamide | 3-CF₃, 4-F |
| E272 | Ex. 3 | 2,6-dimethylpyridin-4-yl | N-methyl-N-methylpropanamide | 3-CF₃, 4-OCH₃ |

TABLE 1-continued

| Co. No. | Exp No. | R¹ | L | Rˣ |
|---|---|---|---|---|
| E268 | Ex. 3 | 2,6-dimethylpyridin-4-yl | N-methyl-propanamide (N-CH₃, C(=O)) | 3-F, 5-Cl |
| E271 | Ex. 3 | 2,6-dimethylpyridin-4-yl | N-methyl-propanamide | 3-F, 5-F |
| E270 | Ex. 3 | 2,6-dimethylpyridin-4-yl | N-methyl-propanamide | 3-Cl, 5-OCH₃ |
| E274 | Ex. 3 | 2,6-dimethylpyridin-4-yl | N-methyl-propanamide | 3-F, 5-CF₃ |
| E269 | Ex. 3 | 2,6-dimethylpyridin-4-yl | N-methyl-propanamide | 3-OCH₃, 5-CF₃ |
| E263 | Ex. 3 | 2,6-dimethylpyridin-4-yl | N-methyl-propanamide | 2-F, 3-F, 4-F |
| E278 | Ex. 3 | 2,6-dimethylpyridin-4-yl | N-methyl-propanamide | 2-F, 3-CF₃, 5-OCH₃ |
| E264 | Ex. 3 | 2,6-dimethylpyridin-4-yl | N-methyl-propanamide | 3-F, 4-F, 5-F |

TABLE 1-continued

| Co. No. | Exp No. | R¹ | L | Rˣ |
|---|---|---|---|---|
| E74 | Ex. 3 | 3-chloropyridin-4-yl | N-methyl-N-methylpropanamide | 3-CF$_3$, 4-F |
| E75 | Ex. 3 | 6-methylpyridin-3-yl | N-methyl-N-methylpropanamide | 3-OCF$_3$ |
| E5 | Ex. 5 | 2-methylpyridin-3-yl | N-methyl-N-methylpropanamide | 3-OCF$_3$ |
| E76 | Ex. 3 | 2-chloropyridin-3-yl | N-methyl-N-methylpropanamide | 3-OCF$_3$ |
| E4 | Ex. 4 | 2-methoxypyridin-3-yl | N-methyl-N-methylpropanamide | 3-OCF$_3$ |
| E6 | Ex. 6 | 2-(methylamino)pyridin-3-yl | N-methyl-N-methylpropanamide | 3-OCF$_3$ |
| E3 | Ex. 3 | 2,3-dihydrobenzo[b][1,4]dioxin-6-yl | N-methyl-N-methylpropanamide | 3-F, 4-F |
| E77 | Ex. 3 | 2,3-dihydrobenzo[b][1,4]dioxin-6-yl | N-methyl-N-methylpropanamide | 3-CF$_3$, 4-F |
| E151 | Ex. 3 | 2,3-dihydrobenzo[b][1,4]dioxin-6-yl | N-methyl-N-methylpropanamide | 3-Br, 4-F, 5-F |

TABLE 1-continued
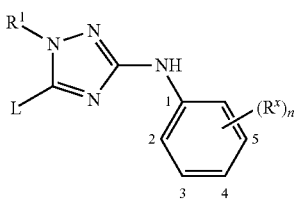
| Co. No. | Exp No. | R¹ | L | Rˣ |
|---|---|---|---|---|
| E170 | Ex. 3 | 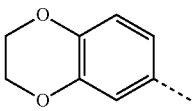 | 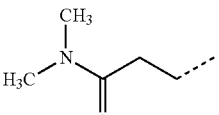 | 3-OCF₃ |
| E78 | Ex. 3 | 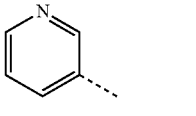 | 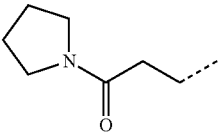 | 3-OCF₃ |
| E79 | Ex. 3 | 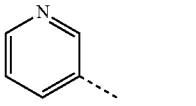 | 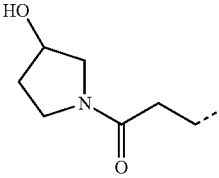 | 3-OCF₃ |
| E80 | Ex. 1 | 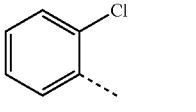 | 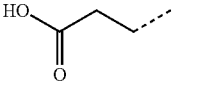 | 3-F, 4-F |
| E81 | Ex. 1 | 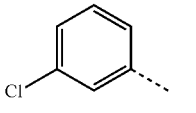 | 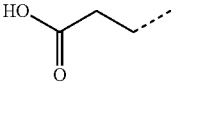 | 3-F, 4-F |
| E82 | Ex. 1 | 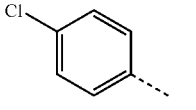 | 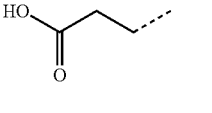 | 3-F, 4-F |
| E83 | Ex. 1 | 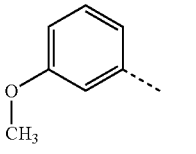 | 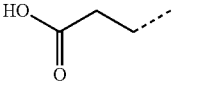 | 3-OCF₃ |
| E84 | Ex. 1 | 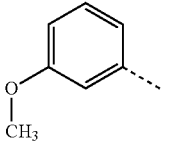 | 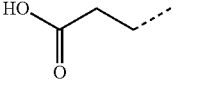 | 3-CF₃, 4-F |
| E85 | Ex. 1 | 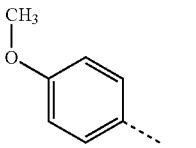 | 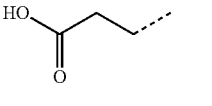 | 3-F, 4-F |

TABLE 1-continued
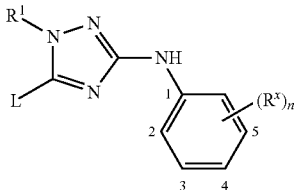
| Co. No. | Exp No. | R¹ | L | Rˣ |
|---|---|---|---|---|
| E86 | Ex. 1 | 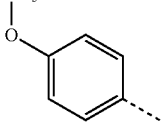 | 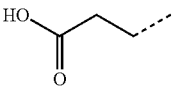 | 3-CF₃, 4-F |
| E87 | Ex. 1 | 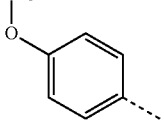 | 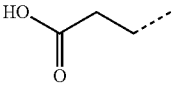 | 3-F, 4-F |
| E88 | Ex. 1 | 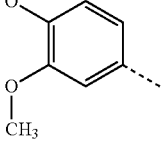 | 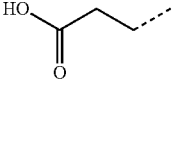 | 3-F, 4-F |
| E89 | Ex. 1 | 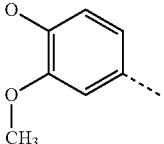 | 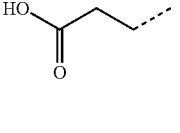 | 3-CF₃, 4-F |
| E90 | Ex. 1 | 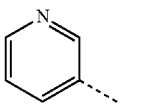 | 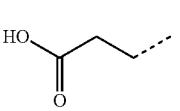 | 3-OCF₃ |
| E91 | Ex. 1 | 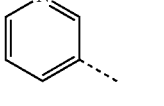 | 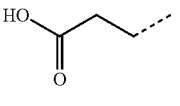 | 3-F, 4-F |
| E92 | Ex. 1 | 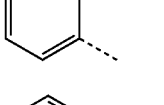 | 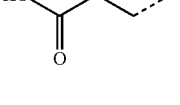 | 3-CF₃, 4-F |
| E93 | Ex. 1 | 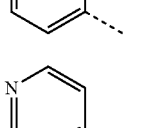 | 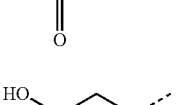 | 3-OCF₃ |
| E94 | Ex. 1 | 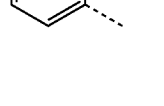 | 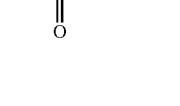 | 3-F, 4-F |

TABLE 1-continued

| Co. No. | Exp No. | R¹ | L | Rˣ |
|---|---|---|---|---|
| E95 | Ex. 1 | pyridin-4-yl | -CH₂CH₂C(O)OH | 3-CF₃, 4-F |
| E96 | Ex. 1 | 2-chloropyridin-3-yl | -CH₂CH₂C(O)OH | 3-OCF₃ |
| E97 | Ex. 1 | 3-chloropyridin-4-yl | -CH₂CH₂C(O)OH | 3-CF₃, 4-F |
| E98 | Ex. 1 | 6-methylpyridin-3-yl | -CH₂CH₂C(O)OH | 3-OCF₃ |
| E99 | Ex. 1 | 2-methylpyridin-4-yl | -CH₂CH₂C(O)OH | 3-OCF₃ |
| E1 | Ex. 1 | 2,3-dihydro-1,4-benzodioxin-6-yl | -CH₂CH₂C(O)OH | 3-F, 4-F |
| E100 | Ex. 1 | 2,3-dihydro-1,4-benzodioxin-6-yl | -CH₂CH₂C(O)OH | 3-CF₃, 4-F |
| E101 | D. 14 | 2-chlorophenyl | -CH₂CH₂C(O)OCH₂CH₃ | 3-F, 4-F |
| E102 | D. 14 | 3-chlorophenyl | -CH₂CH₂C(O)OCH₂CH₃ | 3-F, 4-F |
| E103 | D. 14 | 4-chlorophenyl | -CH₂CH₂C(O)OCH₂CH₃ | 3-F, 4-F |
| E104 | D. 14 | 3-methoxyphenyl | -CH₂CH₂C(O)OCH₂CH₃ | 3-CF₃, 4-F |

TABLE 1-continued

| Co. No. | Exp No. | R¹ | L | Rˣ |
|---|---|---|---|---|
| E105 | D. 14 | 3-methoxyphenyl | ethyl propanoate | 3-OCF₃ |
| E106 | D. 14 | 4-methoxyphenyl | ethyl propanoate | 3-F, 4-F |
| E107 | D. 14 | 4-methoxyphenyl | ethyl propanoate | 3-CF₃, 4-F |
| E108 | D. 14 | pyridin-3-yl | ethyl propanoate | 3-OCF₃ |
| E109 | D. 14 | 2-chloropyridin-3-yl | ethyl propanoate | 3-OCF₃ |
| E110 | D. 14 | 3-chloropyridin-4-yl | ethyl propanoate | 3-CF₃, 4-F |
| E111 | D. 14 | 6-methylpyridin-3-yl | ethyl propanoate | 3-OCF₃ |
| E112 | D. 14 | 2-methylpyridin-4-yl | ethyl propanoate | 3-OCF₃ |
| E113 | D. 14 | 2-methylpyridin-4-yl | ethyl propanoate | 3-CF₃, 4-F |

TABLE 1-continued
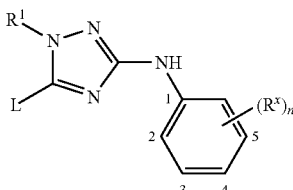
| Co. No. | Exp No. | R¹ | L | Rˣ |
|---|---|---|---|---|
| E114 | D. 14 | 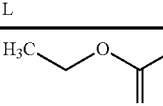 | 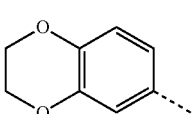 | 3-F, 4-F |
| E115 | D. 14 | 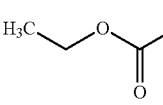 | 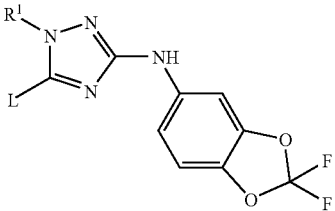 | 3-CF₃, 4-F |
TABLE 2
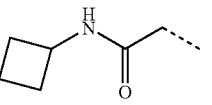
| Co. No. | Ex. No. | R¹ | L |
|---|---|---|---|
| E179 | Ex. 257 | 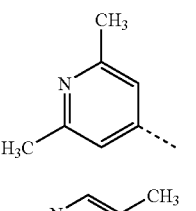 | 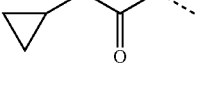 |
| E180 | Ex. 257 | 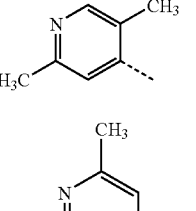 | 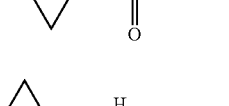 |
| E160 | Ex. 257 | 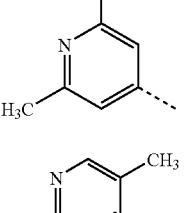 |  |
| E201 | Ex. 257 | 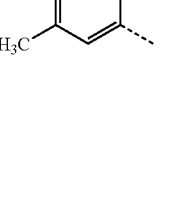 | 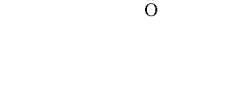 |
| E161 | Ex. 257 | 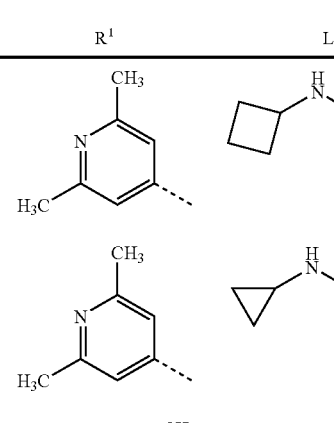 | 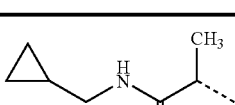 |
TABLE 2-continued
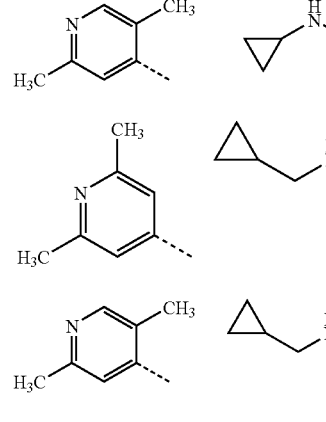
| Co. No. | Ex. No. | R¹ | L |
|---|---|---|---|
| E281 | Ex. 257 | 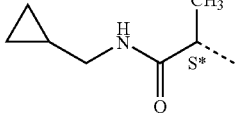 |  RS mixture |
| E282 | Ex. 257 | | R* enantiomer |
| E283 | Ex. 257 | | S* enantiomer |
| E200 | Ex. 257 | |  |

TABLE 2-continued

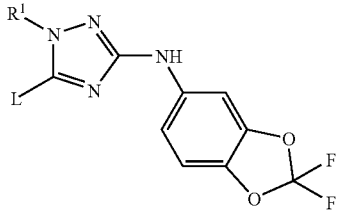

| Co. No. | Ex. No. | R¹ | L |
|---|---|---|---|
| E275 | Ex. 257 | 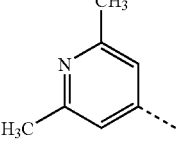 | 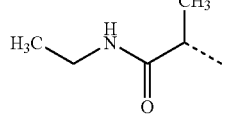 RS mixture |
| E163 | Ex. 257 | 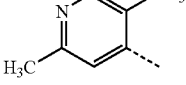 | 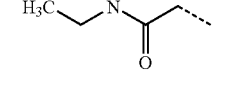 |
| E178 | Ex. 2 | 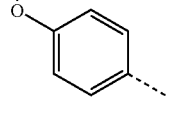 | 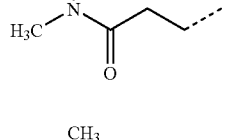 |
| E116 | Ex. 4 | 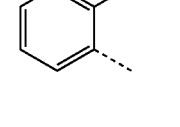 | 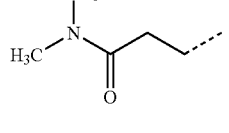 |
| E117 | Ex. 3 | 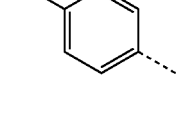 | 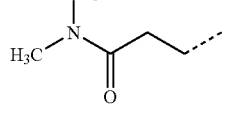 |
| E118 | Ex. 3 | 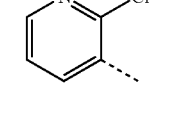 | 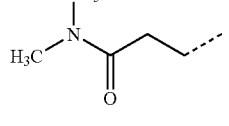 |
| E119 | Ex. 3 | 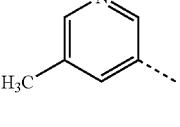 | 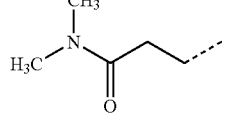 |
| E235 | Ex. 2 | 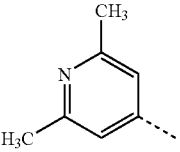 | 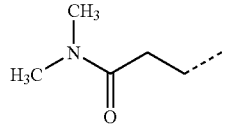 |
| E176 | Ex. 2 | 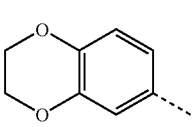 | 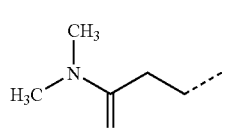 |

TABLE 2-continued

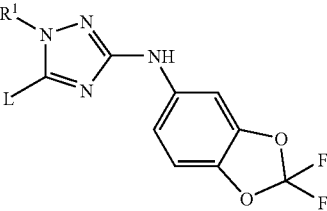

| Co. No. | Ex. No. | R¹ | L |
|---|---|---|---|
| E122 | Ex. 1 | 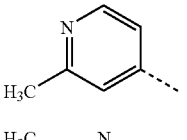 | 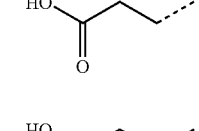 |
| E120 | Ex. 1 | 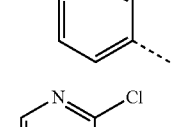 | 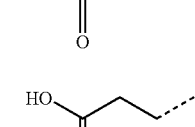 |
| E121 | Ex. 1 | 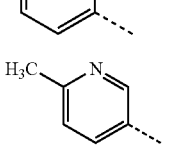 | 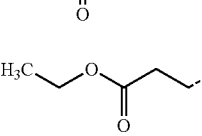 |
| E123 | D. 14 | 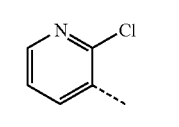 | 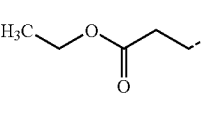 |
| E124 | D. 14 | 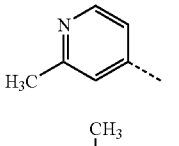 | 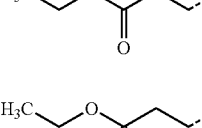 |
| E125 | D. 14 | 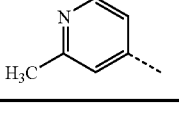 | 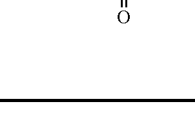 |
| E280 | D. 14 | 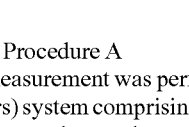 | 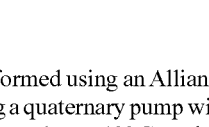 |

Analytical Part

LCMS

LCMS General Procedure A

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS General Procedure B

The HPLC measurement was performed using an Agilent 1100 module comprising a pump, a diode-array detector (DAD) with Gilson 215 autosampler and a column as specified in the respective methods below. Flow from the column was split to a MS spectrometer. Ionisation was either electrospray or APCI (atmospheric pressure chemical ionization) depending on type of compound. Typical electrospray conditions use a capillary needle voltage of 3.5 kV, a cone voltage of 25 V and the source temperature was maintained at a temperature between 120-150° C. (the exact temperature was determined on a compound-by-compound basis). Typical APCI conditions use a corona discharge current of 17 µA, a cone voltage of 25 V, a desolvation temperature of 350° C. and the source temperature was maintained at a temperature between 140-160° C. (the exact temperature was determined on a compound-by-compound basis). Mass spectra were acquired by scanning from 100 to 650 or 1000 when required, for example in 1 second using a dwell time of 0.1 sec. Nitrogen was used as the nebulizer gas.

LCMS General Procedure C

The HPLC measurement was performed using a Waters 1512 pump with a Waters diode-array detector (DAD) with Gilson 215 autosampler and a column as specified in the respective methods below. Flow from the column was split to a MS spectrometer. Ionisation was either electrospray or APCI (atmospheric pressure chemical ionization) depending on type of compound. Typical electrospray conditions use a capillary needle voltage of 3.5 kV and a cone voltage of 25 V. The source temperature was maintained at a temperature between 120-150° C. (the exact temperature was determined on a compound-by-compound basis). Typical APCI conditions use a corona discharge current of 17 µA, a cone voltage of 25 V, a desolvation temperature of 350° C. and the source temperature was maintained at a temperature between 140-160° C. (the exact temperature was determined on a compound-by-compound basis). Mass spectra were acquired by scanning from 100 to 650 or 1000 when required, for example in 1 second using a dwell time of 0.1 sec. Nitrogen was used as the nebulizer gas.

LCMS General Procedure D

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

LCMS General Procedure E

The HPLC measurement was performed using an HP 1100 (Agilent Technologies) system comprising a pump (quaternary or binary) with degasser, an auto-sampler, a column oven, a diode-array detector (DAD) and a column as specified in the respective methods below. Flow from the column was split to the MS spectrometer. The MS detector was configured with either an electrospray ionization source or an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

LCMS General Procedure F

The HPLC (Ultra Performance Liquid Chromatography) measurement was performed using an Acquity HPLC (Waters) system comprising a sampler organizer, a binary pump with degasser, a four column's oven, a diode-array detector (DAD) and a column as specified in the respective methods below. Column flow was used without split to the MS detector. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

LCMS General Procedure G

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

LCMS—Procedure 1

In addition to general procedure A: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 min., to 1% A and 99% B in 1 min. and hold these conditions for 1 min. and reequilibrate with 100% A for 1.5 min. An injection volume of 10 µl was used. Cone voltage was 10 V for positive ionization mode and 20 V for negative ionization mode.

LCMS—Procedure 2

In addition to general procedure A: Column heater was set at 60° C. Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% $CH_3CN$; mobile phase B: $CH_3CN$; mobile phase C: MeOH) were employed to run a gradient condition from 100% A to 50% B and 50% C in 6.5 min., to 100% B in 0.5 min. and hold these conditions for 1 min. and reequilibrate with 100% A for 1.5 min. An injection volume of 10 µl was used. Cone voltage was 10 V for positive ionization mode and 20 V for negative ionization mode.

LCMS—Procedure 3

In addition to general procedure A: Column heater was set at 45° C. Reversed phase HPLC was carried out on an Xterra MS C18 column (3.5 nm, 4.6×100 mm) with a flow rate of 1.6 ml/min. Three mobile phases (mobile phase A: 0.1% formic acid in $H_2O$/methanol 95/5; mobile phase B: acetonitrile; mobile phase C: methanol) were employed to run a gradient condition from 100% A to 1% A, 49% B and 50% C in 7 min. and hold these conditions for 1 min. An injection volume of 10 µl was used. Cone voltage was 10 V for positive ionization mode.

LCMS—Procedure 4

In addition to general procedure B: Reversed phase HPLC was carried out on a Phenomenex Luna 5µ C18 (2) column (4.6×100 mm; plus guard cartridge) with a flow rate of 2 ml/min. Two mobile phases (mobile phase A: water with 0.1% formic acid; mobile phase B: $CH_3CN$ with 0.1% (V/V) formic acid) were employed to run a gradient condition from 95% A to 95% B with a flow rate of 2 ml/min. in 3.5 min. and hold for 2 min. Typically, injection volumes of between 2 μl and 7 μl, inclusive were used.

LCMS—Procedure 5

In addition to general procedure C: Reversed phase HPLC was carried out on a Waters Xterra MS 5μ C18 column (4.6× 100 mm; plus guard cartridge) with a flow rate of 2 ml/min. Two mobile phases (mobile phase A: water with 10 mM ammonium bicarbonate; mobile phase B: $CH_3CN$) were employed to run a gradient condition from 95% A to 95% B with a flow rate of 2 ml/min in 3.5 min. and hold for 2 min. Typically, injection volumes of between 2 μl and 7 μl, inclusive were used.

LCMS—Procedure 6

In addition to general procedure A: Column heater was set at 45° C. Reversed phase HPLC was carried out on an Atlantis C18 column (3.5 nm, 4.6×100 mm) with a flow rate of 1.6 ml/min. Two mobile phases (mobile phase A: 70% MeOH+ 30% $H_2O$; mobile phase B: 0.1% formic acid in $H_2O$/methanol 95/5) were employed to run a gradient condition from 100% B to 5% B+95% A in 9 min. and hold these conditions for 3 min. An injection volume of 10 μl was used. Cone voltage was 10 V for positive ionization mode and 20 V for negative ionization mode.

LCMS—Procedure 7

In addition to general procedure D: Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 0.1% formic acid in $H_2O$/MeOH 95/5; mobile phase B: MeOH) were used to run a gradient condition from 95% A and 5% B to 5% A and 95% B in 1.3 min. and hold for 0.2 min. An injection volume of 0.5 μl was used. Cone voltage was 10 V for positive ionization mode and 20 V for negative ionization mode.

LCMS—Procedure 8

In addition to general procedure A: Reversed phase HPLC was carried out on an Atlantis C18 column (3.5 μm, 4.6×100 mm) with a flow rate of 1.6 ml/min. Two mobile phases (mobile phase A: 70% MeOH+30% $H_2O$; mobile phase B: 0.1% formic acid in $H_2O$/MeOH 95/5) were employed to run a gradient condition from 100% B to 5% B+95% A in 12 min. An injection volume of 10 μl was used.

Cone voltage was 10 V for positive ionization mode and 20 V for negative ionization mode.

LCMS—Procedure 9

In addition to general procedure A: Reversed phase HPLC was carried out on a Chromolith (4.6×25 mm) with a flow rate of 3 ml/min. Three mobile phases (mobile phase A: 95% 25 mM ammoniumacetate+5% $CH_3CN$; mobile phase B: $CH_3CN$; mobile phase C: MeOH) were employed to run a gradient condition from 96% A, 2% B and 2% C, to 49% B and 49% C in 0.9 min., to 100% B in 0.3 min. and hold for 0.2 min. An injection volume of 2 μl was used. Cone voltage was 10 V for positive ionization mode and 20 V for negative ionization mode.

LCMS—Procedure 10

In addition to the general procedure A: Column heater was set at 60° C. Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS—Procedure 11

In addition to the general procedure E: Reversed phase HPLC was carried out on a Sunfire-C18 column (2.5 μm, 2.1×30 mm) from Waters, with a flow rate of 1.0 ml/min, at 60° C. The gradient conditions used are: 95% A (0.5 g/l ammonium acetate solution+5% of acetonitrile), 2.5% B (acetonitrile), 2.5% C (methanol) to 50% B, 50% C in 6.5 minutes, kept till 7.0 minutes and equilibrated to initial conditions at 7.3 minutes until 9.0 minutes. Injection volume 2 μl. High-resolution mass spectra (Time of Flight, TOF detector) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

LCMS—Procedure 12

In addition to the general procedure F: Reversed phase HPLC was carried out on a BEH-C18 column (1.7 μm, 2.1× 50 mm) from Waters, with a flow rate of 0.8 ml/min, at 60° C. without split to the MS detector. The gradient conditions used are: 95% A (0.5 g/l ammonium acetate solution+5% acetonitrile), 5% B (mixture of acetonitrile/methanol, 1/1), to 20% A, 80% B in 4.9 minutes, to 100% B in 5.3 minutes, kept till 5.8 minutes and equilibrated to initial conditions at 6.0 minutes until 7.0 minutes. Injection volume 0.5 μl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 20 V for positive ionization mode and 30 V for negative ionization mode.

LCMS—Procedure 13

In addition to general procedure D: Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (25 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used.

Cone voltage was 10 V for positive ionization mode and 20 V for negative ionization mode.

Melting Points

For a number of compounds, melting points were determined with a DSC823e from Mettler-Toledo. Melting points were measured with a temperature gradient of 30 C/minute. Values are peak values.

TABLE 3

Analytical data - Retention time ($R_t$ in minutes), $(MH)^+$ peak, LCMS procedure and melting points (m.p. is defined as melting point).

| Co. Nr. | $R_t$ | $[M + H]^+$ | LCMS Procedure | m.p. (° C.) |
|---|---|---|---|---|
| E1 | 3.46 | 403 | 4 | |
| E2 | 3.34 | 416 | 4 | |
| E3 | 3.52 | 430 | 4 | |
| E4 | 5.43 | 451 | 2 | 166.7 |
| E5 | 5.14 | 435 | 2 | |
| E6 | 5.31 | 450 | 2 | 212.8 |
| E7 | 1.17 | 396 | 7 | 197.6 |
| E8 | 1.26 | 398 | 7 | 191.5 |
| E9 | 1.32 | 414 | 7 | 182.8 |

TABLE 3-continued

Analytical data - Retention time ($R_t$ in minutes), $(MH)^+$ peak, LCMS procedure and melting points (m.p. is defined as melting point).

| Co. Nr. | $R_t$ | $[M + H]^+$ | LCMS Procedure | m.p. (° C.) |
|---|---|---|---|---|
| E10 | 1.18 | 396 | 7 | 192.7 |
| E11 | 1.32 | 378 | 7 | 226.3 |
| E12 | 6.49 | 430 | 3 | 105.3 |
| E13 | 1.23 | 396 | 7 | 170.4 |
| E14 | 1.26 | 416 | 7 | 152.9 |
| E15 | 1.27 | 410 | 7 | 141.4 |
| E16 | 1.13 | 382 | 7 | |
| E17 | 8.37 | 349 | 6 | 177.1 |
| E18 | 8.75 | 399 | 6 | 161.0 |
| E19 | 8.19 | 349 | 6 | 178.0 |
| E20 | 8.61 | 399 | 6 | 170.4 |
| E21 | 8.19 | 361 | 6 | 181.4 |
| E22 | 8.64 | 411 | 6 | 188.7 |
| E23 | 7.18 | 344 | 6 | 185.0 |
| E24 | 1.02 | 346 | 7 | 212.0 |
| E25 | 8.27 | 416 | 6 | 150.3 |
| E26 | 9.23 | 450 | 6 | 162.9 |
| E27 | 8.64 | 363 | 6 | 158.1 |
| E28 | 8.49 | 363 | 6 | 157.3 |
| E29 | 8.47 | 375 | 6 | 117.6 |
| E30 | 1.10 | 360 | 7 | 171.1 |
| E31 | 1.20 | 396 | 7 | 181.9 |
| E32 | 1.27 | 424 | 7 | |
| E34 | 1.29 | 438 | 7 | |
| E35 | 1.12 | 409 | 7 | 272.9 |
| E36 | 1.20 | 402 | 7 | |
| E37 | 7.45 | 423 | 8 | 284.2 |
| E38 | 1.21 | 392 | 7 | |
| E39 | 5.95 | 392 | 1 | |
| E40 | 1.30 | 392 | 7 | 177.3 |
| E41 | 5.68 | 436 | 2 | 139.4 |
| E42 | 5.99 | 438 | 1 | 170.9 |
| E43 | 3.31 | 388 | 4 | |
| E44 | 3.36 | 438 | 5 | |
| E45 | 3.16 | 418 | 4 | |
| E46 | 3.24 | 468 | 5 | |
| E47 | 3.73 | 442 | 4 | |
| E48 | 2.78 | 359 | 4 | |
| E49 | 3.07 | 409 | 4 | |
| E50 | 3.13 | 407 | 4 | |
| E51 | 5.48 | 421 | 1 | |
| E52 | 2.41 | 359 | 4 | |
| E53 | 2.69 | 407 | 4 | |
| E54 | 1.13 | 421 | 7 | 153.7 |
| E55 | 3.56 | 466 | 4 | |
| E56 | 3.21 | 435 | 5 | |
| E57 | 1.26 | 406 | 7 | 179.6 |
| E58 | 5.82 | 406 | 2 | 165.4 |
| E59 | 5.80 | 406 | 2 | 145.1 |
| E60 | 6.21 | 450 | 1 | 133.5 |
| E61 | 5.71 | 452 | 2 | 173.6 |
| E62 | 3.55 | 452 | 5 | |
| E63 | 3.39 | 402 | 5 | |
| E64 | 3.16 | 432 | 4 | |
| E65 | 3.58 | 482 | 4 | |
| E66 | 3.70 | 456 | 5 | |
| E67 | 1.04 | 373 | 7 | |
| E68 | 2.81 | 423 | 4 | |
| E69 | 2.82 | 421 | 4 | |
| E70 | 2.86 | 373 | 5 | |
| E71 | 3.32 | 421 | 4 | |
| E72 | 3.23 | 423 | 4 | |
| E73 | 1.15 | 435 | 7 | 215.4 |
| E74 | 6.09 | 457 | 3 | 181.7 |
| E75 | 5.38 | 435 | 2 | 174.3 |
| E76 | 5.37 | 455 | 2 | 145.7 |
| E77 | 3.75 | 480 | 4 | |
| E78 | 3.25 | 447 | 5 | |
| E79 | 2.96 | 463 | 4 | |
| E84 | 0.86 | 425 | 9 | |
| E85 | 3.46 | 375 | 4 | |
| E86 | 3.68 | 425 | 4 | |
| E87 | 3.85 | 429 | 4 | |
| E88 | 3.30 | 405 | 4 | |
| E89 | 3.53 | 455 | 4 | |
| E90 | 3.28 | 394 | 4 | |
| E91 | 2.94 | 346 | 4 | |
| E92 | 3.21 | 396 | 4 | |
| E93 | 2.86 | 394 | 4 | |
| E94 | 2.54 | 346 | 4 | |
| E95 | 2.84 | 396 | 4 | |
| E100 | 3.67 | 453 | 4 | |
| E104 | 1.07 | 453 | 9 | |
| E105 | 1.09 | 451 | 9 | |
| E106 | 3.97 | 403 | 4 | |
| E107 | 4.17 | 453 | 4 | |
| E108 | 3.81 | 422 | 4 | |
| E110 | 1.39 | 458 | 7 | |
| E113 | 5.87 | 438 | 3 | |
| E114 | 1.33 | 431 | 7 | |
| E116 | 5.35 | 431 | 1 | 151.7 |
| E117 | 1.24 | 431 | 7 | |
| E118 | 1.25 | 451 | 7 | 195.8 |
| E119 | 5.51 | 431 | 1 | 141.1 |
| E122 | 0.80 | 404 | 9 | |
| E123 | 0.99 | 432 | 9 | |
| E124 | 1.01 | 452 | 9 | |
| E125 | 1.00 | 432 | 9 | |
| E126 | 7.64 | 396 | 6 | 192.9 |
| E127 | 5.99 | 392 | 1 | |
| E128 | 7.60 | 436 | 6 | 138.8 |
| E129 | 6.93 | 372 | 6 | 154.6 |
| E130 | 5.68 | 378 | 1 | |
| E131 | 7.36 | 360 | 6 | 168.0 |
| E132 | 6.64 | 374 | 6 | 180.6 |
| E133 | 8.22 | 422 | 6 | 156.2 |
| E134 | | | | 175.8 |
| E135 | 7.86 | 408 | 6 | 196.3 |
| E136 | 5.57 | 389 | 1 | |
| E137 | 8.10 | 422 | 6 | 174.1 |
| E138 | 7.77 | 374 | 6 | 169.4 |
| E139 | 7.61 | 358 | 6 | 126.7 |
| E140 | | | | 127.5 |
| E141 | 6.23 | 360 | 6 | 225.7 |
| E142 | 8.25 | 422 | 6 | 154.7 |
| E143 | 8.03 | 408 | 6 | 137.5 |
| E144 | 7.84 | 394 | 6 | 145.5 |
| E145 | 7.52 | 346 | 6 | 144.2 |
| E146 | 8.51 | 423 | 6 | 135.4 |
| E147 | 8.01 | 435 | 6 | 146.8 |
| E148 | 7.21 | 410 | 6 | 224.9 |
| E149 | 8.57 | 375 | 6 | 144.1 |
| E150 | 6.77 | 415 | 6 | 248.8 |
| E151 | 3.74 | 508 | 12 | |
| E152 | 7.39 | 429 | 6 | 234.0 |
| E153 | 6.7 | 403 | 6 | 231.4 |
| E154 | 7.17 | 429 | 6 | |
| E155 | 3.76 | 480 | 12 | |
| E156 | 7.61 | 403 | 6 | 186.5 |
| E157 | 7.63 | 415 | 6 | 192.6 |
| E158 | 7.92 | 429 | 6 | |
| E159 | 7.96 | 429 | 6 | |
| E160 | 1.24 | 443 | 7 | 248.3 |
| E161 | 1.29 | 457 | 7 | 227.2 |
| E162 | 1.2 | 413 | 7 | 244.1 |
| E163 | 1.24 | 431 | 7 | |
| E164 | 1.13 | 387 | 7 | 230.2 |
| E165 | 7.45 | 461 | 6 | 247.5 |
| E166 | 1.2 | 413 | 7 | 211.2 |
| E167 | 6.19 | 387 | 6 | 296.8 |
| E168 | 6.40 | 399 | 6 | 279.3 |
| E169 | 6.90 | 413 | 6 | |
| E170 | 3.67 | 478 | 11 | |
| E171 | 1.11 | 431 | 7 | 270.0 |
| E172 | 7.16 | 390 | 6 | |
| E173 | 7.73 | 376 | 6 | 127.9 |
| E174 | 1.18 | 445 | 7 | 276.3 |
| E175 | 1.1 | 419 | 7 | 283.6 |

TABLE 3-continued

Analytical data - Retention time ($R_t$ in minutes), $(MH)^+$ peak, LCMS procedure and melting points (m.p. is defined as melting point).

| Co. Nr. | $R_t$ | $[M + H]^+$ | LCMS Procedure | m.p. (° C.) |
|---|---|---|---|---|
| E176 | 3.63 | 474 | 12 | |
| E177 | 1.17 | 445 | 7 | 260.9 |
| E178 | 3.68 | 446 | 12 | |
| E179 | 7.41 | 457 | 6 | 291.3 |
| E180 | 7.05 | 443 | 6 | 292.6 |
| E181 | 7.28 | 435 | 6 | 277.5 |
| E182 | 7.33 | 447 | 6 | 282.2 |
| E183 | 4.76 | 450 | 11 | |
| E184 | 7.71 | 461 | 6 | 264.4 |
| E185 | 6.68 | 413 | 6 | 278.7 |
| E186 | 7.05 | 372 | 6 | |
| E187 | 7.82 | 378 | 6 | 177.4 |
| E188 | 7.52 | 392 | 6 | 176.6 |
| E189 | 6.48 | 378 | 6 | 138.0 |
| E190 | 1.04 | 386 | 7 | |
| E191 | 7.49 | 403 | 6 | |
| E192 | 7.87 | 429 | 6 | 187.9 |
| E193 | 7.84 | 429 | 6 | |
| E194 | 5.64 | 378 | 1 | 177.7 |
| E195 | 8.23 | 422 | 6 | 151.9 |
| E196 | 7.86 | 358 | 6 | 110.4 |
| E197 | 6.24 | 360 | 6 | 225.1 |
| E198 | 6.71 | 346 | 6 | 210.3 |
| E199 | 7.17 | 410 | 6 | 224.4 |
| E200 | 7.01 | 431 | 6 | 280.9 |
| E201 | 7.36 | 457 | 6 | 270.3 |
| E202 | 4.93 | 354 | 1 | 133.2 |
| E203 | 4.77 | 368 | 10 | |
| E204 | 5.40 | 392 | 10 | |
| E205 | 7.33 | 402 | 6 | |
| E206 | 1.26 | 388 | 7 | |
| E207 | 7.68 | 364 | 6 | 200.2 |
| E208 | 7.08 | 378 | 6 | 199.6 |
| E212 | 7.11 | 431 | 6 | 249.4 |
| E213 | 6.84 | 419 | 6 | 252.1 |
| E214 | 7.06 | 431 | 6 | 213.7 |
| E215 | 7.09 | 405 | 6 | 296.1 |
| E217 | 1.29 | 461 | 7 | 281.4 |
| E218 | 7.34 | 449 | 6 | 278.8 |
| E219 | 6.95 | 415 | 6 | 254.0 |
| E220 | 8.19 | 436 | 6 | |
| E221 | 7.01 | 427 | 6 | 264.4 |
| E222 | 0.99 | 441 | 12 | 257.8 |
| E223 | 7.02 | 423 | 6 | 264.2 |
| E224 | 7.23 | 437 | 6 | 256.2 |
| E225 | 7.65 | 463 | 6 | 248.8 |
| E226 | 7.26 | 449 | 6 | |
| E227 | 6.42 | 435 | 6 | 263.0 |
| E228 | 6.53 | 389 | 6 | 284.5 |
| E229 | 6.69 | 461 | 6 | 265.7 |
| E230 | 6.89 | 415 | 6 | 287.4 |
| E231 | 7.3 | 429 | 6 | 273.9 |
| E232 | 1.01 | 373 | 7 | 282.1 |
| E233 | 1.14 | 451 | 7 | 184.0 |
| E234 | 0.99 | 401 | 7 | 200.2 |
| E235 | 1.12 | 445 | 7 | 178.0 |
| E236 | 7.11 | 475 | 6 | 268.7 |
| E237 | 0.9 | 387 | 13 | 289.0 |
| E238 | 0.91 | 399 | 13 | 289.2 |
| E239 | 0.97 | 413 | 13 | 286.7 |
| E240 | 6.81 | 391 | 6 | 297.4 |
| E241 | 7.14 | 417 | 6 | 295.7 |
| E242 | 7.56 | 431 | 6 | 291.9 |
| E243 | 7.12 | 435 | 6 | 284.6 |
| E244 | 7.71 | 475 | 6 | 278.4 |
| E245 | 7.02 | 389 | 6 | 280.7 |
| E246 | 1.17 | 403 | 7 | 290.2 |
| E247 | 1.18 | 415 | 7 | 289.3 |
| E248 | 1.07 | 429 | 13 | 287.0 |
| E249 | 6.67 | 449 | 6 | 256.5 |
| E250 | 6.83 | 403 | 6 | 283.2 |
| E251 | 7.45 | 423 | 6 | 286.2 |
| E252 | 7.67 | 437 | 6 | 284.5 |
| E253 | 7.72 | 449 | 6 | 286.3 |
| E254 | 8.06 | 463 | 6 | 291.8 |
| E255 | 6.95 | 423 | 6 | 232.7 |
| E256 | 7.19 | 437 | 6 | 231.8 |
| E257 | 7.28 | 449 | 6 | 244.4 |
| E258 | 7.68 | 463 | 6 | 233.2 |
| E259 | 6.98 | 423 | 6 | 241.9 |
| E260 | 7.24 | 437 | 6 | |
| E261 | 7.3 | 449 | 6 | 241.0 |
| E262 | 7.69 | 463 | 6 | 246.8 |
| E263 | | | | 154.9 |
| E264 | 1.12 | 419 | 7 | |
| E265 | 1.11 | 417 | 7 | |
| E270 | | | | 140.5 |
| E271 | | | | 205.9 |
| E273 | | | | 207.4 |
| E275 | 7.39 | 445 | 6 | 244.0 |
| E277 | 5.41 | 364 | 1 | 131.4 |
| E280 | 1.25 | 432 | 7 | |
| E281 | 5.89 | 471 | 1 | 223.6 |
| E282 | 5.88 | 471 | 1 | 221.7 |
| E283 | 5.90 | 471 | 1 | 222.4 |

TABLE 4

Analytical data - Retention time ($R_t$ in minutes), $(MH)^-$ peak, LCMS procedure and melting points (m.p. is defined as melting point).

| Co. Nr. | $R_t$ | $[M - H]^-$ | LCMS Procedure | m.p. (° C.) |
|---|---|---|---|---|
| E209 | 6.15 | 389 | 6 | |
| E210 | 6.49 | 403 | 6 | 241.5 |
| E216 | 0.88 | 399 | 13 | 246.2 |
| E211 | 6.55 | 415 | 6 | 237.3 |

Optical Rotation

For some compounds, the optical rotation was measured using a Perkin Elmer 341 polarimeter (results shown in Table 5). $[\alpha]_D^{20}$ indicates the optical rotation measured with light at the wavelength of 589 nm or 365 nm at a temperature of 20° C. The cell pathlength is 1 dm. Behind the actual value, the concentration of the solution which was used to measure the optical rotation is mentioned. All measurements were performed in methanol, except for Co. No. E282 and E283. For the measurement of Co. No. E282 and E283 DMF was used as the solvent.

TABLE 5

Optical rotation

| Co. No. | $[\alpha]_D^{20}$ | wavelength (nm) | concentration (w/v %) |
|---|---|---|---|
| E24 | −69.33° | 365 | 0.1428 |
| E30 | +10.15° | 589 | 0.2068 |
| E17 | +13.74° | 589 | 0.2402 |
| E21 | +12.18° | 589 | 0.3858 |
| E19 | +18.58° | 589 | 0.3714 |
| E20 | +17.10° | 589 | 0.4270 |
| E18 | +12.90° | 589 | 0.4652 |
| E22 | +11.19° | 589 | 0.4112 |
| E26 | +7.32° | 589 | 0.4374 |
| E25 | +17.01° | 589 | 0.4468 |
| E28 | +16.86° | 589 | 0.4924 |
| E27 | +12.00° | 589 | 0.4250 |
| E29 | +12.23° | 589 | 0.4906 |

TABLE 5-continued

Optical rotation

| Co. No. | $[\alpha]_D^{20}$ | wavelength (nm) | concentration (w/v %) |
|---|---|---|---|
| E23 | +15.64° | 589 | 0.4412 |
| E126 | −11.93° | 589 | 0.3940 |
| E128 | −12.14° | 589 | 0.3542 |
| E129 | +14.83° | 589 | 0.4720 |
| E131 | +10.84° | 589 | 0.3966 |
| E132 | +12.07° | 589 | 0.4392 |
| E133 | +10.20° | 589 | 0.4214 |
| E134 | −10.41° | 589 | 0.3746 |
| E137 | +11.59° | 589 | 0.3968 |
| E138 | +8.35° | 589 | 0.4310 |
| E139 | +10.63° | 589 | 0.4702 |
| E149 | +15.52° | 589 | 0.4060 |
| E148 | +14.58° | 589 | 0.4048 |
| E146 | +13.4° | 589 | 0.2612 |
| E145 | +19.76° | 589 | 0.5062 |
| E140 | +15.31° | 589 | 0.3658 |
| E144 | +19.6° | 589 | 0.3826 |
| E142 | +14.14° | 589 | 0.4384 |
| E196 | +15.53° | 589 | 0.4056 |
| E195 | −14.44° | 589 | 0.4294 |
| E198 | −13.01° | 589 | 0.3844 |
| E197 | −14.85° | 589 | 0.3502 |
| E199 | −12.63° | 589 | 0.3562 |
| E189 | +11.53° | 589 | 0.2342 |
| E172 | +13.46° | 589 | 0.327 |
| E173 | +11.85° | 589 | 0.3206 |
| E188 | +13.39° | 589 | 0.433 |
| E187 | +11.28° | 589 | 0.3812 |
| E207 | +13.72° | 589 | 0.532 |
| E208 | +15.34° | 589 | 0.4888 |
| E282 | −24.61° | 365 | 0.4064 |
| E283 | +26.05° | 365 | 0.3916 |

NMR

For a number of compounds, $^1$H NMR spectra were recorded on a Bruker DPX-360 or on a Bruker DPX-400 spectrometer with standard pulse sequences, operating at 360 MHz and 400 MHz respectively, using DMSO-$d_6$ as solvent. Chemical shifts (δ) are reported in parts per million (ppm) relative to tetramethylsilane (TMS), which was used as internal standard.

Compound E137:
$^1$H NMR (400 MHz, DMSO-$d_6$) δ ppm 0.89 (t, J=7.4 Hz, 3 H), 1.37-1.50 (m, 1 H), 1.51-1.63 (m, 1 H), 2.57 (s, 3 H), 2.93 (dd, J=15.1, 7.8 Hz, 1 H), 3.00 (dd, J=15.1, 4.8 Hz, 1 H), 3.81 (s, 3 H), 3.90 (qt, J=7.4, 5.0 Hz, 1 H), 4.90 (d, J=5.2 Hz, 1 H), 6.70 (t, J=1.8 Hz, 1 H), 7.47 (t, J=1.7 Hz, 1 H), 7.54 (dd, J=5.6, 2.1 Hz, 1 H), 7.56 (t, J=2.1 Hz, 1 H), 7.60 (d, J=2.0 Hz, 1 H), 8.61 (d, J=5.4 Hz, 1 H), 9.82 (s, 1H)

13C NMR (101 MHz, DMSO-$d_6$) δ ppm 9.79 (s, 1 C), 24.17 (s, 1 C), 29.58 (s, 1 C), 33.99 (s, 1 C), 55.33 (s, 1 C), 70.22 (s, 1 C), 101.07 (q, J=3.7 Hz, 1 C), 105.05-105.28 (m, 2 C), 115.08 (s, 1 C), 116.85 (s, 1 C), 124.14 (q, J=272.1 Hz, 1 C), 130.46 (q, J=31.5 Hz, 1 C), 143.30 (s, 1 C), 144.17 (s, 1 C), 150.33 (s, 1 C), 153.91 (s, 1 C), 159.19 (s, 1 C), 159.73 (s, 1 C), 160.30 (s, 1 C)

Compound E190:
$^1$H NMR (360 MHz, DMSO-$d_6$) δ ppm 0.88 (t, J=7.3 Hz, 3 H), 1.35-1.48 (m, 1 H), 1.48-1.60 (m, 1 H), 2.52 (s, 6 H), 2.89 (dd, J=15.0, 7.7 Hz, 1 H), 2.97 (dd, J=15.0, 5.1 Hz, 1 H), 3.73 (s, 3 H), 3.88 (qt, J=7.4, 5.1 Hz, 1 H), 4.91 (d, J=5.3 Hz, 1 H), 6.29 (dt, J=11.0, 2.3 Hz, 1 H), 7.00-7.05 (m, 2 H), 7.38 (s, 2 H), 9.66 (s, 1 H)

Compound E205:
$^1$H NMR (360 MHz, DMSO-$d_6$) δ ppm 0.88 (t, J=7.4 Hz, 3 H), 1.34-1.48 (m, 1 H), 1.48-1.60 (m, 1 H), 2.51 (s, 6 H), 2.89 (dd, J=15.0, 7.7 Hz, 1 H), 2.96 (dd, J=15.0, 4.8 Hz, 1 H), 3.74 (s, 3 H), 3.87 (qt, J=7.4, 5.1 Hz, 1 H), 4.90 (d, J=5.5 Hz, 1 H), 6.49 (t, J=2.0 Hz, 1 H), 7.18 (t, J=1.9 Hz, 1 H), 7.23 (t, J=2.1 Hz, 1 H), 7.38 (s, 2 H), 9.67 (s, 1 H)

Compound E187:
$^1$H NMR (360 MHz, DMSO-$d_6$) δ ppm 0.89 (t, J=7.4 Hz, 3 H), 1.37-1.61 (m, 1 H), 1.37-1.61 (m, 1 H), 2.57 (s, 3 H), 2.91 (dd, J=15.0, 8.1 Hz, 1 H), 2.99 (dd, J=15.0, 4.8 Hz, 1 H), 3.88 (qt, J=7.5, 5.0 Hz, 1 H), 4.94 (d, J=5.2 Hz, 1 H), 7.42 (dd, J=11.0, 6.2 Hz, 2 H), 7.56 (dd, J=5.4, 2.1 Hz, 1 H), 7.61 (d, J=2.0 Hz, 1 H), 8.61 (d, J=5.4 Hz, 1 H), 9.95 (s, 1 H)

Compound E200:
$^1$H NMR (400 MHz, DMSO-$d_6$) δ ppm 0.99 (t, J=7.3 Hz, 3 H), 2.50 (s, 6 H), 3.07 (qd, J=7.2, 5.5 Hz, 2 H), 3.84 (s, 2 H), 7.26 (dd, J=8.8, 2.0 Hz, 1 H), 7.30 (d, J=8.8 Hz, 1 H), 7.36 (s, 2 H), 7.69 (d, J=2.0 Hz, 1 H), 8.28 (t, J=5.5 Hz, 1 H), 9.68 (s, 1 H)

Compound E180:
$^1$H NMR (360 MHz, DMSO-$d_6$) δ ppm 0.31-0.40 (m, 2 H), 0.56-0.65 (m, 2 H), 2.50 (s, 6 H), 2.53-2.63 (m, 1 H), 3.81 (s, 2 H), 7.26 (dd, J=8.8, 2.2 Hz, 1 H), 7.31 (d, J=8.8 Hz, 1 H), 7.35 (s, 2 H), 7.69 (d, J=2.2 Hz, 1 H), 8.39 (d, J=4.1 Hz, 1 H), 9.72 (s, 1 H)

Compound E182:
$^1$H NMR (360 MHz, DMSO-$d_6$) δ ppm 0.32-0.37 (m, 2 H), 0.59-0.65 (m, 2 H), 2.50 (s, 6 H), 2.54-2.63 (m, 1 H), 3.83 (s, 2 H), 6.78-6.83 (m, 1 H), 7.33 (s, 2 H), 7.38 (t, J=8.2 Hz, 1 H), 7.51 (dd, J=8.2, 2.1 Hz, 1 H), 7.64-7.69 (m, 1 H), 8.41 (d, J=4.1 Hz, 1 H), 9.82 (s, 1 H)

Compound E153:
$^1$H NMR (400 MHz, DMSO-$d_6$) δ ppm 0.99 (t, J=7.2 Hz, 3 H), 2.50 (s, 6 H), 3.07 (qd, J=7.2, 5.5 Hz, 1 H), 3.85 (s, 2 H), 7.06 (ddd, J=8.1, 6.5, 1.6 Hz, 1 H), 7.16 (td, J=8.2, 1.5 Hz, 1 H), 7.36 (s, 2 H), 8.09 (td, J=8.4, 1.5 Hz, 1 H), 8.30 (t, J=5.5 Hz, 1 H), 9.29 (s, 1 H)

Compound E188:
$^1$H NMR (360 MHz, DMSO-$d_6$) δ ppm 0.88 (t, J=7.4 Hz, 3 H), 1.36-1.60 (m, 1 H), 1.36-1.60 (m, 1 H), 2.52 (s, 6 H), 2.89 (dd, J=15.0, 7.7 Hz, 1 H), 2.97 (dd, J=15.0, 4.8 Hz, 1 H), 3.88 (tq, J=7.4, 5.0 Hz, 1 H), 4.91 (d, J=5.3 Hz, 1 H), 7.41 (dd, J=11.0, 6.2 Hz, 2 H), 7.40 (s, 2 H), 9.93 (s, 1 H)

Compound E186:
$^1$H NMR (360 MHz, DMSO-$d_6$) δ ppm 0.89 (t, J=7.4 Hz, 3 H), 1.37-1.61 (m, 1 H), 1.37-1.61 (m, 1 H), 2.57 (s, 3 H), 2.91 (dd, J=15.0, 7.7 Hz, 1 H), 2.99 (dd, J=15.0, 4.9 Hz, 1 H), 3.73 (s, 3 H), 3.89 (tq, J=7.4, 5.1 Hz, 1 H), 4.94 (d, J=5.2 Hz, 1 H), 6.30 (dt, J=11.1, 2.2 Hz, 1 H), 7.01-7.06 (m, 1 H), 7.02 (d, J=2.3 Hz, 1 H), 7.55 (dd, J=5.4, 2.1 Hz, 1 H), 7.60 (d, J=2.0 Hz, 1 H), 8.60 (d, J=5.4 Hz, 1 H), 9.70 (s, 1 H)

Compound E127:
$^1$H NMR (360 MHz, DMSO-$d_6$) δ ppm 0.88 (t, J=7.4 Hz, 3 H), 1.36-1.59 (m, 1 H), 1.36-1.59 (m, 1 H), 2.51 (s, 6 H), 2.89 (dd, J=15.0, 7.9 Hz, 1 H), 2.97 (dd, J=15.0, 4.8 Hz, 1 H), 3.88 (tq, J=7.5, 5.0 Hz, 1 H), 4.92 (d, J=5.2 Hz, 1 H), 7.21-7.31 (m, J=10.0, 10.0, 8.5, 2.4 Hz, 1 H), 7.39 (s, 2 H), 7.86-7.94 (m, J=9.2, 9.2, 5.3, 2.5 Hz, 1 H), 9.31 (s, 1 H)

Compound E235:
$^1$H NMR (360 MHz, DMSO-$d_6$) δ ppm 2.53 (s, 6 H), 2.79 (s, 3 H), 2.88 (t, J=6.5 Hz, 2 H), 2.99 (s, 3 H), 3.08 (t, J=6.5 Hz, 2 H), 7.26 (dd, J=8.8, 2.1 Hz, 1 H), 7.30 (d, J=8.8 Hz, 1 H), 7.39 (s, 2 H), 7.69 (d, J=2.0 Hz, 1 H), 9.69 (s, 1 H)

Compound E234:
$^1$H NMR (360 MHz, DMSO-$d_6$) δ ppm 2.79 (s, 3 H), 2.87 (t, J=6.5 Hz, 2 H), 2.99 (s, 3 H), 3.08 (t, J=6.5 Hz, 2 H), 7.25-7.37 (m, 2 H), 7.38 (s, 2 H), 7.64 (ddd, J=13.8, 7.3, 2.3 Hz, 1 H), 9.69 (s, 1 H)

Compound E130:

$^1$H NMR (360 MHz, DMSO-$d_6$) δ ppm 0.88 (t, J=7.4 Hz, 3 H), 1.35-1.48 (m, 1 H), 1.47-1.60 (m, 1 H), 2.56 (s, 3 H), 2.90 (dd, J=15.0, 8.1 Hz, 1 H), 2.98 (dd, J=15.0, 4.4 Hz, 1 H), 3.88 (qt, J=7.6, 4.9 Hz, 1 H), 4.95 (d, J=5.2 Hz, 1 H), 7.21-7.32 (m, 1 H), 7.60 (d, J=2.0 Hz, 1 H), 7.55 (dd, J=5.4, 2.1 Hz, 1 H), 7.87-7.94 (m, 1 H), 8.59 (d, J=5.4 Hz, 1 H), 9.36 (s, 1 H)

Compound E167:

$^1$H NMR (360 MHz, DMSO-$d_6$) δ ppm 0.99 (t, J=7.2 Hz, 3 H), 2.50 (s, 6 H), 3.07 (qd, J=7.2, 5.4 Hz, 2 H), 3.84 (s, 2 H), 7.25-7.38 (m, 4 H), 7.64 (ddd, J=13.6, 7.2, 2.6 Hz, 1 H), 8.31 (t, J=5.5 Hz, 1 H), 9.72 (s, 1 H)

Compound E189:

$^1$H NMR (360 MHz, DMSO-$d_6$) δ ppm 1.16 (d, J=6.2 Hz, 3 H), 2.51 (s, 6 H), 2.86-2.98 (m, 2 H), 4.07-4.18 (m, 1 H), 4.94 (d, J=4.8 Hz, 1 H), 7.22-7.31 (m, J=10.0, 10.0, 8.4, 2.3 Hz, 1 H), 7.37 (s, 2 H), 7.85-7.93 (m, J=9.2, 9.2, 5.3, 2.5 Hz, 1 H), 9.32 (s, 1 H)

SFC-MS

For some compounds SFC-MS (Supercritical fluid chromatography-mass spectrometry) was measured with an analytical SFC system from Berger Instruments (Newark, Del., USA) comprising a dual pump control module (FCM-1200) for delivery of carbon dioxide ($CO_2$) and modifier, a thermal control module for column heating (TCM2100) with temperature control in the range of 1-150° C. and column selection valves (Valco, VICI, Houston, Tex., USA) for six different columns. The photodiode array detector (Agilent 1100, Waldbronn, Germany) is equipped with a high-pressure flow cell (up to 400 bar) and configured with a CTC LC Mini PAL auto sampler (Leap Technologies, Carrboro, N.C., USA). A ZQ mass spectrometer (Waters, Milford, Mass., USA) with an orthogonal Z-electrospray interface is coupled with the SFC-system. Instrument control, data collection and processing were performed with an integrated platform consisting of the SFC ProNTo software and Masslynx software.

For Co. No.E24 an enantiomeric excess was found of 100% when a screening was performed with 4 different columns (Chiralcel OJ-H, Chiralpak AD-H, Chiralcel OD-H, Chiralpak AS-H; 500×4.6 mm; Daicel Chemical Industries Ltd) and 3 different solvents (MeOH, EtOH, 2-propanol; the solvent is containing 0.2% 2-propylamine) SFC-MS was carried out with one of the columns mentioned above with a flow rate of 3 ml/min. Two mobile phases (mobile phase A: $CO_2$; mobile phase B: one of the solvents mentioned above containing 0.2% 2-propylamine) were employed to run a condition from 10% B to 40% B in 18.75 min. Then a gradient was applied from 40% B to 50% B in 2 min. and hold for 3.6 min. Column temperature was set at 50° C.

Identical SFC-MS conditions as for Co. No.E24, were used for the SFC-MS measurements of Co. No. E10, E17, E19, E20, E18, E22, E126, E208, E207, E144, E198, E197, E199 and E189. For all these compounds an enantiomeric excess of 100% was found under the screening conditions.

For Co. No. E30 an enantiomeric purity of 97.48% was found when SFC-MS was carried out on a Chiralcel OJ-H column (500×4.6 mm) (Daicel Chemical Industries Ltd) with a flow rate of 3 ml/min. Two mobile phases (mobile phase A: $CO_2$; mobile phase B: EtOH containing 0.2% 2-propylamine) were employed to run a condition from 10% B to 40% B in 18.75 min. Then a gradient was applied from 40% B to 50% B in 2 min. and hold for 3.6 min. Column temperature was set at 50° C.

Identical SFC-MS conditions as for Co. No. E30, were used for the SFC-MS measurements of Co. No. E137. Identical conditions were also used for the SFC-MS measurements of Co. No. E139. Under these conditions an enantiomeric purity of 93.57% was found. Identical conditions were also used for the SFC-MS measurements of Co. No. E172. Under these conditions an enantiomeric purity of 97.73% was found. Identical conditions were also used for the SFC-MS measurements of Co. No. E173. Under these conditions an enantiomeric purity of 97.29% was found. Identical conditions were also used for the SFC-MS measurements of Co. No. E145. Under these conditions an enantiomeric purity of 99.01% was found.

For Co. No. E129 an enantiomeric purity of 96.83% was found when SFC-MS was carried out on a Chiralcel OJ-H column (500×4.6 mm) (Daicel Chemical Industries Ltd) with a flow rate of 3 ml/min. Two mobile phases (mobile phase A: $CO_2$; mobile phase B: MeOH containing 0.2% 2-propylamine) were employed to run a condition from 10% B to 40% B in 18.75 min. Then a gradient was applied from 40% B to 50% B in 2 min. and hold for 3.6 min. Column temperature was set at 50° C.

For Co. No. E21 an enantiomeric purity of 99.40% was found when SFC-MS was carried out on a Chiralcel OD-H column (500×4.6 mm) (Daicel Chemical Industries Ltd) with a flow rate of 3 ml/min. Two mobile phases (mobile phase A: $CO_2$; mobile phase B: MeOH containing 0.2% 2-propylamine) were employed to run a condition from 10% B to 40% B in 18.75 min. Then a gradient was applied from 40% B to 50% B in 2 min. and hold for 3.6 min. Column temperature was set at 50° C.

Identical SFC-MS conditions as for Co. No. E21, were used for the SFC-MS measurements of Co. No. E25. Under these conditions an enantiomeric purity of 99.76% was found For Co. No. E26 an enantiomeric purity of 99.36% was found when SFC-MS was carried out on a Chiralcel OD-H column (500×4.6 mm) (Daicel Chemical Industries Ltd) with a flow rate of 3 ml/min. Two mobile phases (mobile phase A: $CO_2$; mobile phase B: EtOH containing 0.2% 2-propylamine) were employed to run a condition from 10% B to 40% B in 18.75 min. Then a gradient was applied from 40% B to 50% B in 2 min. and hold for 3.6 min. Column temperature was set at 50° C.

For Co. No. E28 an enantiomeric purity of 97.52% was found when SFC-MS was carried out on a Chiralpak AD-H column (500×4.6 mm) (Daicel Chemical Industries Ltd) with a flow rate of 3 ml/min. Two mobile phases (mobile phase A: $CO_2$; mobile phase B: methanol containing 0.2% 2-propylamine) were employed to run a condition from 10% B to 40% B in 18.75 min. Then a gradient was applied from 40% B to 50% B in 2 min. and hold for 3.6 min. Column temperature was set at 50° C.

Identical SFC-MS conditions as for Co. No. E28, were used for the SFC-MS measurements of Co. No. E133. Under these conditions an enantiomeric purity of 98.34% was found. Identical conditions were also used for the SFC-MS measurements of Co. No. E187. Under these conditions an enantiomeric purity of 97.87% was found.

For Co. No. E27 an enantiomeric purity of 98.69% was found when SFC-MS was carried out on a Chiralpak AD-H column (500×4.6 mm) (Daicel Chemical Industries Ltd) with a flow rate of 3 ml/min. Two mobile phases (mobile phase A: $CO_2$; mobile phase B: EtOH containing 0.2% 2-propylamine) were employed to run a condition from 10% B to 40% B in 18.75 min. Then a gradient was applied from 40% B to 50% B in 2 min. and hold for 3.6 min. Column temperature was set at 50° C.

Identical SFC-MS conditions as for Co. No. E27, were used for the SFC-MS measurements of Co. No. E128. Under these conditions an enantiomeric purity of 99.30% was found. Identical conditions were also used for the SFC-MS measurements of Co. No. E132. Under these conditions an enantiomeric purity of 97.11% was found. Identical conditions were also used for the SFC-MS measurements of Co. No. E138. Under these conditions an enantiomeric purity of 96.77% was found. Identical conditions were also used for the SFC-MS measurements of Co. No. E148. Under these conditions an enantiomeric purity of 99.25% was found. Identical conditions were also used for the SFC-MS measurements of Co. No. E149. Under these conditions an enantiomeric purity of 99.11% was found.

For Co. No. E29 an enantiomeric purity of 97.89% was found when SFC-MS was carried out on a Chiralpak AD-H column (500×4.6 mm) (Daicel Chemical Industries Ltd) with a flow rate of 3 ml/min. Two mobile phases (mobile phase A: $CO_2$; mobile phase B: 2-propanol containing 0.2% 2-propylamine) were employed to run a condition from 10% B to 40% B in 18.75 min. Then a gradient was applied from 40% B to 50% B in 2 min. and hold for 3.6 min. Column temperature was set at 50° C.

For Co. No. E131 an enantiomeric purity of 99.60% was found when SFC-MS was carried out on a Chiralpak AD-H column (500×4.6 mm) (Daicel Chemical Industries Ltd) with a flow rate of 3 ml/min. Two mobile phases (mobile phase A: $CO_2$; mobile phase B: MeOH containing 0.2% 2-propylamine) were employed to run a condition from 10% B to 40% B in 18.75 min. Then a gradient was applied from 40% B to 50% B in 2 min. and hold for 3.6 min. Column temperature was set at 50° C.

Identical SFC-MS conditions as for Co. No. E131, were used for the SFC-MS measurements of Co. No. E146. Under these conditions an enantiomeric purity of 99.55% was found. Identical conditions were also used for the SFC-MS measurements of Co. No. E142. Under these conditions an enantiomeric purity of 99.09% was found.

For Co. No. E282 an enantiomeric purity of 100% was found when SFC-MS was carried out on a Chiralpak AD-H column (500×4.6 mm) (Daicel Chemical Industries Ltd) with a flow rate of 3 ml/min. Two mobile phases (mobile phase A: $CO_2$; mobile phase B: methanol containing 0.2% 2-propylamine) were employed. First 15% B was hold for 17.16 min. Then a gradient was applied from 15% B to 50% B in 7 min. and hold for 1.34 min. Column temperature was set at 50° C. This measurement was compared against the racemic mixture.

For Co. No. E196 an enantiomeric purity of 93.73% was found when SFC-MS was carried out on a Chiralpak AS-H column (500×4.6 mm) (Daicel Chemical Industries Ltd) with a flow rate of 3 ml/min. Two mobile phases (mobile phase A: $CO_2$; mobile phase B: ethanol containing 0.2% 2-propylamine) were employed. First 15% B was hold for 18 min. Then a gradient was applied from 15% B to 50% B in 3.5 min. and hold for 3.1 min. Column temperature was set at 50° C.

For Co. No. E195 an enantiomeric purity of 99.51% was found when SFC-MS was carried out on a Chiralpak AS-H column (500×4.6 mm) (Daicel Chemical Industries Ltd) with a flow rate of 3 ml/min. Two mobile phases (mobile phase A: $CO_2$; mobile phase B: ethanol containing 0.2% 2-propylamine) were employed to run a condition from 10% B to 40% B in 18.75 min. Then a gradient was applied from 40% B to 50% B in 2 min. and hold for 3.6 min. Column temperature was set at 50° C.

D. PHARMACOLOGICAL EXAMPLES

Example D.1 a $Ca^{2+}$ Flux Imaging (FLIPR) (Protocol A)

Stable expression in mammalian cells in general and rat GH4Cl cells in particular, of cDNA clones encoding the human α7 wild-type sequence (hα7-wt nAChR) and in which the coding region is placed downstream of a promoter results in the appearance of functional α7 nAChRs on the surface of the mammalian cells. This technique has provided a powerful means of assessing the function of α7 wild-type protein. Given the fact that the cation permeability of the α7 nicotinic receptor preferentially favours calcium, fluorescent imaging of $Ca^{2+}$ flux through the hα7-wt nAChR stably expressed in the GH4Cl cell line was used as a first means of assaying modulator activity of the compounds of the present invention.

Materials a) Assay buffer

Hanks buffered saline solution (HBSS, Invitrogen, Belgium), supplemented with 10 mM HEPES (Invitrogen, Belgium), $CaCl_2$ to a final concentration of 5 mM, 0.1% Bovine serum albumin (Sigma-Aldrich NV, Belgium), 2.5 mM probenecid (Sigma-Aldrich NV, Belgium).

b) Calcium-sensitive dye—Fluo-4AM

Fluo-4AM (Molecular Probes, USA) was dissolved in DMSO containing 10% Pluronic acid (Molecular Probes, USA) to give a stock solution which was aliquoted and stored at −20° C. until later use. On the day of the experiment Fluo-4AM stock was defrosted and diluted in DMEM/F12 (Invitrogen, Belgium) to give a final concentration of 4 μM.

c) 96-well plates

BD Biocoat poly-D-lysine 96-well black/clear plates (BD Biosciences, Belgium)

d) Calcium flux measurement

A Fluorimetric Imaging Plate Reader (FLIPR, Molecular Devices Corporation, Sunnyvale, USA) was used to measure intracellular free-calcium flux signals Method Monolayers of hα7-wt nAChR-expressing cells were grown in multi-well plates, in particular black-sided, transparent bottomed 96 well plates coated with poly-D-lysine for 24 hours prior to loading with a fluorescent calcium indicator, in a particular embodiment loading with fluo-3 or fluo-4AM for up to 90 minutes, in an even more particular embodiment loading with fluo-4AM for up to 90 minutes, and in a preferred embodiment loading with fluo-4AM for up to 60 minutes.

PAM activity was detected in real time by applying the compounds to be tested to the loaded cells along with a α7 nicotinic receptor agonist during constant monitoring of cellular fluorescence in a FLIPR. Compounds giving peak fluorescent responses greater than the response due to agonist alone, were considered to be α7 nAChR PAM's. In a particular embodiment, the α7 nicotinic receptor agonist was choline, a more particular embodiment choline applied at a submaximal concentration of 100 μM. In a further setting of the present invention the compounds to be tested were applied prior to the α7 nicotinic receptor agonist, in a particular embodiment up to 20 minutes prior to the agonist, a more particular embodiment up to 10 minutes prior to the agonist, and an even more particular embodiment 10 minutes prior to the agonist.

A control response to choline was calculated on each plate from the difference in peak in fluorescence in wells receiving either choline or assay buffer alone. Compounds of the present invention were tested at a concentration range from 0.1 μM to 50 μM. Compounds were considered to have an interesting activity when their efficacy was at least 500% when tested at the concentration where they have a maximal effect, typically between 0.1 μM and 50 μM (the efficacy of 100 μM choline was defined as 100% in the absence of a PAM). The compounds also have a potentiating effect on the response to choline when measured by whole-cell patch clamp electrophysiology in GH4Cl cells stably over-expressing the human wild-type α7 receptor.

Example D.1 b

Ca$^{2+}$ Flux Imaging (FDSS) (Protocol B)

Materials
a) Assay buffer
Hanks buffered saline solution (HBSS, Invitrogen, Belgium), supplemented with 10 mM HEPES (Invitrogen, Belgium), CaCl$_2$ to a final concentration of 5 mM, 0.1% Bovine serum albumin (Sigma-Aldrich NV, Belgium).
b) Calcium-sensitive dye—Fluo-4AM
Fluo-4AM (Molecular Probes, USA) was dissolved in DMSO containing 10% Pluronic acid (Molecular Probes, USA) to give a stock solution which was diluted in assay buffer supplemented with 5 mM probenicid (Sigma, Al-drich NV, Belgium) to give a final concentration of 2 µM.
c) 384-well plates
Black 384 well plate black/clear plates, PDL pre-coated (Corning, Incorporated, USA)
d) Calcium flux measurement
A Functional drug screening system (FDSS, Hamamatsu) was used to measure intracellular free-calcium flux signals.

Method
Monolayers of hα7-wt nAChR-expressing cells were grown in multi-well plates, in particular black-sided, transparent bottomed 384 well plates coated with poly-D-lysine for 24 hours prior to loading with a fluorescent calcium indicator, in a particular embodiment loading with fluo-4AM for up to 120 minutes.

PAM activity was detected in real time by applying the compounds to be tested to the loaded cells along with a α7 nicotinic receptor agonist during constant monitoring of cellular fluorescence in a FDSS. Compounds giving peak fluorescent responses greater than the response due to agonist alone, were considered to be α7 nAChR PAM's. In a particular embodiment, the α7 nicotinic receptor agonist was choline, a more particular embodiment choline applied at a sub-maximal concentration of 100 µM. In a further setting of the present invention the compounds to be tested were applied prior to the α7 nicotinic receptor agonist, in a particular embodiment up to 10 minutes prior to the agonist.

A control response to choline was calculated on each plate from the difference in peak in fluorescence in wells receiving either choline or assay buffer alone. Compounds of the present invention were tested at a concentration range from 0.01 µM to 30 µM. Compounds were considered to have an interesting activity when they potentiated the choline signal at least with 500% when tested at a concentration of 30 µM (the efficacy of 100 µM choline was defined as 100% in the absence of a PAM). The compounds also have a potentiating effect on the response to choline when measured by whole-cell patch clamp electrophysiology in GH4Cl cells stably over-expressing the human wild-type α7 receptor.

Example D.2

Patch-clamp Current Recording

Patch-clamp recording from mammalian cells has provided a powerful means of assessing the function of membrane-bound proteins thought to be subunits of ligand-gated ion channels. Activation of such proteins by endogenous or exogenous ligands cause opening of a pore associated with the receptor through which ions flow down their electrochemical gradient. In the case of the hα7-wt nAChR-expressing GH4Cl recombinant cell line the preferential permeability to calcium of this receptor means that calcium flows into the cell upon activation by ACh, choline and other nicotinic ligands giving rise to a calcium current. Since this receptor rapidly desensitizes in the presence of agonist it is important an application system is used which is capable of very rapid switching of solutions (<100 ms) to prevent partial or full desensitisation of receptor responses coincident with the time of agonist application. Consequently, a second convenient technique to assess the enhancement of nicotinic efficacy is patch-clamp recording from hα7-wt nAChR-expressing GH4Cl cells coupled with a rapid-application system.

Materials
a) Assay buffers
The external recording solution consisted of 152 mM NaCl, 5 mM KCl, 1 mM MgCl$_2$, 1 mM Calcium, 10 mM HEPES; pH 7.3. The internal recording solution consisted of 140 mM CsCl, 10 mM HEPES, 10 mM EGTA, 1 mM MgCl$_2$, pH 7.3.
b) Patch-clamp recording was carried out using a Patch-clamp amplifier (Multiclamp 700A, Axon Instruments, Calif., USA). hα7-wt nAChR-expressing GH4Cl cells were patch-clamp in the whole cell configuration (Hamill et al, 1981) with a borosilicate glass electrode of 1.5-3 MΩ tip resistance when filled with the internal recording solution. Recordings were made on cells with membrane resistance >500 MΩ and more preferably 1GΩ and series resistance <15 MΩ with at least 60% series resistance compensation. Membrane potential was clamped at −70 mV.
c) Agonists
ACh, choline, were purchased from Sigma-Aldrich NV, Belgium.
d) Compound application
A 16-channel Dynflow DF-16 microfluidics system (Cellectricon, Sweden) for rapid switching of solutions (switching resolution time <100 ms) was used to apply control, agonist and PAM compounds to hα7-wt nAChR-expressing GH4Cl cells.

Method
hα7-wt nAChR-expressing GH4Cl cells were plated in external recording solution in the Dynaflow perfusion chamber and were allowed to settle for up to 20 minutes. Individual cells were whole-cell patched and gently lifted off the chamber bottom with the patch pipette into a continuously-flowing perfusion stream (12 µl/min) of external recording solution. PAM activity was detected in real time by pre-applying the compounds to be tested to the loaded cells followed by an α7 nicotinic receptor agonist during constant monitoring of cellular membrane current. Compounds giving current responses greater than the response due to agonist alone, were considered to be α7 nAChR PAM's. In a particular embodiment, the α7 nicotinic receptor agonist was activated by a non-selective nicotinic agonist, in a more particular embodiment the agonist was choline, and an even more particular embodiment choline applied at a sub-maximal concentration of 1 mM. In a further setting of the present invention the compounds to be tested were applied prior to the α7 nicotinic receptor agonist, in a more particular embodiment up to 30 seconds prior to the agonist and even more particularly 5 seconds prior to the agonist. A control response was calculated from the area under the curve of the current elicited in each cell to an application of submaximal choline for 250 ms.

Area under the curve is the integration of net current over time and is a common representation of the total ion flux through the channel. Increases in agonist efficacy elicited by a positive allosteric modulator were calculated as percent potentiation of "area under curve" (AUC) of the agonist response. Potentiation greater than control AUC caused by compounds of the invention indicates that they are expected to have useful therapeutic activity. $EC_{50}$ values (potency), maximal effect (% efficacy), and Hill slopes were estimated by fitting the data to the logistic equation using GraphPad Prism (GraphPad Software, Inc., San Diego, Calif.).

PAM types are as defined on pages 19 and 20 hereinbefore.

An $EC_{50}$ (or $pEC_{50}$) was determined as a concentration relating to half the maximal effect, when a clear sigmoidal curve with top plateau was obtained. The $EC_{50}$ (or $pEC_{50}$) was defined as lower than maximal concentration in case the compound activity did not reach a top plateau at maximal concentration (indicated in table 6 as "<5")

TABLE 6

Potency ($pEC_{50}$) (according to Ex. D.2) and % efficacy (according to Ex. D.1b) for a number of compounds.

| ID | $pEC_{50}$ | % Efficacy | Pam type |
|---|---|---|---|
| E2 | 5.99 | 1392 | 3 |
| E3 | 7.36 | 1938 | 4 |
| E4 | 5.42 | 1546 | |
| E5 | 5.93 | 2144 | 4 |
| E6 | 6.07 | 2581 | |
| E7 | 6.00 | 1625 | 2 |
| E8 | 6.29 | 1345 | 0 |
| E9 | 6.36 | 1200 | |
| E10 | 5.98 | 3262 | 2 |
| E11 | 6.86 | 341 | |
| E12 | 5.65 | 1299 | |
| E13 | 6.62 | 2300 | 0 |
| E14 | 5.40 | 1067 | |
| E15 | 6.96 | 1650 | 0 |
| E16 | 6.28 | 1925 | |
| E17 | 5.45 | 1286 | |
| E18 | 5.48 | 1460 | |
| E19 | 5.52 | 445 | |
| E20 | 5.35 | 1474 | |
| E21 | 5.75 | 1613 | 1 |
| E22 | 6.07 | 1717 | 0 |
| E23 | 5.66 | 3608 | |
| E25 | 5.32 | 7623 | 2 |
| E27 | 5.72 | 2669 | 1 |
| E28 | 5.72 | 1850 | 1 |
| E29 | 5.94 | 4058 | 1 |
| E30 | 6.17 | 2922 | 2 |
| E31 | 5.65 | 1449 | 2 |
| E35 | 5.93 | 2345 | 3 |
| E36 | 5.76 | 1910 | 4 |
| E38 | 5.51 | 253 | |
| E39 | 5.59 | 673.5 | |
| E40 | 5.72 | 495 | |
| E42 | 5.56 | 5135 | |
| E43 | 5.70 | 1675 | 2 |
| E44 | 6.18 | 3432 | |
| E46 | 5.99 | 1455 | |
| E47 | 5.82 | 697.5 | |
| E48 | <5 | | |
| E52 | <4.52 | | |
| E54 | 5.64 | 2602 | 2 |
| E55 | 6.28 | 1772 | 4 |
| E57 | 5.97 | 3236 | 3 |
| E58 | 6.47 | 4420 | |
| E59 | 6.61 | 2752 | 4 |
| E60 | 6.55 | 2717 | 0 |
| E61 | 7.07 | 3349 | |
| E62 | 7.52 | 4157 | 4 |
| E63 | 7.22 | 1917 | 4 |
| E64 | 6.28 | 3401 | 4 |
| E65 | 7.15 | 2905 | 4 |
| E66 | 6.62 | 3710 | 4 |
| E67 | 6.35 | 3318 | 4 |
| E68 | 6.98 | 4466 | |
| E69 | 6.49 | 6312 | |
| E71 | 6.21 | 2223 | 4 |
| E72 | 6.47 | 4948 | |
| E73 | 6.87 | 2850 | 4 |
| E74 | 7.14 | 3825 | 4 |
| E75 | 6.73 | 5421 | 4 |
| E76 | 6.39 | 2294 | |
| E77 | 7.40 | 3385 | 4 |
| E78 | 6.51 | 5581 | |
| E79 | 5.90 | 2450 | |
| E108 | 5.87 | 2048 | |
| E114 | 6.82 | 3808 | |
| E115 | 6.80 | 3934 | |
| E116 | 5.53 | 3861 | |
| E117 | 6.72 | 2547 | 4 |
| E118 | 6.16 | 2576 | |
| E119 | 6.97 | 2536 | 4 |
| E126 | 5.73 | 2331 | 2 |
| E127 | 6.57 | 2696 | 2 |
| E128 | 6.90 | 994 | 4 |
| E129 | 6.61 | 1307 | 2 |
| E130 | 6.57 | 5521 | 2 |
| E131 | 5.86 | 3760 | 2 |
| E132 | 6.62 | 4284 | 2 |
| E133 | 6.44 | 4328 | 4 |
| E134 | 5.98 | 2526 | 2 |
| E135 | 6.26 | 4874 | 4 |
| E136 | 6.81 | 4015 | 3 |
| E137 | 6.98 | 2415 | 4 |
| E138 | 6.53 | 3859 | 2 |
| E139 | 6.49 | 3462 | 2 |
| E140 | 5.79 | 2873 | 2 |
| E141 | 5.86 | 961 | 2 |
| E142 | 6.74 | 2094 | 4 |
| E143 | 6.04 | 1367 | 4 |
| E144 | 5.53 | 4417 | |
| E145 | 5.61 | 2103 | |
| E146 | ~6.44 | 2051 | |
| E147 | 6.72 | 2825 | 3 |
| E148 | 6.28 | 4247 | |
| E149 | 5.86 | 1765 | |
| E150 | 6.38 | 1947 | 2 |
| E151 | 7.42 | 2064 | 4 |
| E152 | 6.61 | 1665 | 2 |
| E153 | 6.25 | 1790 | 2 |
| E154 | 6.66 | 1824 | 2 |
| E155 | 7.54 | 3139 | 1 |
| E157 | 5.42 | 492 | 2 |
| E158 | 5.86 | 328.5 | 1 |
| E159 | 5.76 | 592.5 | 1 |
| E160 | 5.67 | 1612 | 2 |
| E161 | 5.88 | 1095 | 2 |
| E162 | 5.54 | 623 | 1 |
| E163 | 5.60 | 1202 | 4 |
| E165 | 6.68 | 1373 | 1 |
| E166 | 5.63 | 589 | 1 |
| E167 | 6.21 | 1682 | 2 |
| E168 | 6.29 | 1260 | 2 |
| E169 | 6.53 | 1154 | 2 |
| E170 | 7.40 | 1768 | 4 |
| E171 | 6.30 | 1652 | 4 |
| E172 | 6.52 | 2517 | 2 |
| E173 | 6.39 | 3328 | 2 |
| E174 | 6.79 | 1996 | 2 |
| E175 | 6.26 | 1924 | 4 |
| E176 | 7.57 | 2773 | 4 |
| E177 | 6.66 | 1444 | 2 |
| E178 | 7.44 | 1217 | 4 |
| E179 | 7.01 | 1760 | 1 |
| E180 | 6.52 | 2262 | 2 |

TABLE 6-continued

Potency (pEC$_{50}$) (according to Ex. D.2) and % efficacy (according to Ex. D.1b) for a number of compounds.

| ID | pEC$_{50}$ | % Efficacy | Pam type |
|---|---|---|---|
| E181 | 6.29 | 2075 | 2 |
| E182 | 6.48 | 1176 | 2 |
| E183 | 7.57 | 717.5 | 1 |
| E184 | 6.59 | 1324 | 2 |
| E185 | 6.33 | 3341 | 2 |
| E186 | 5.99 | 3867 | 4 |
| E187 | 6.65 | 2023 | 2 |
| E188 | 6.65 | 2505 | 2 |
| E189 | 6.20 | 2035 | 2 |
| E190 | 6.40 | 2937 | 2 |
| E192 | 5.80 | 397 | 1 |
| E193 | ~5.52 | 327 | |
| E194 | 5.30 | 1191 | |
| E195 | 5.44 | 1856 | |
| E196 | 6.04 | 1286 | 2 |
| E197 | 5.75 | 1803 | 2 |
| E198 | 5.73 | 808 | 2 |
| E199 | 5.97 | 2128 | 2 |
| E200 | 6.39 | 1920 | 2 |
| E201 | 6.52 | 2069 | 2 |
| E202 | 5.56 | 2039 | 2 |
| E203 | 5.87 | 1972 | 2 |
| E204 | 6.25 | 1557 | 0 |
| E205 | 6.81 | 2862 | 2 |
| E206 | 6.77 | 2964 | 4 |
| E207 | 5.88 | 1885 | 2 |
| E208 | 6.13 | 1792 | 2 |
| E209 | 6.14 | 1463 | 2 |
| E210 | 6.38 | 1337 | 2 |
| E211 | 6.43 | 1259 | 2 |
| E212 | 6.60 | 1143 | 2 |
| E213 | 6.33 | 909 | 2 |
| E214 | 6.88 | 730.5 | 2 |
| E215 | 6.67 | 658 | 2 |
| E216 | 6.22 | 576.5 | 4 |
| E217 | | | 4 |
| E218 | | | 4 |
| E219 | 6.57 | 702.5 | 4 |
| E220 | 5.69 | 645.5 | |
| E221 | 6.68 | 620 | 4 |
| E222 | 7.08 | 440 | 1 |
| E223 | 6.50 | 603 | |
| E224 | 6.69 | 599.5 | 1 |
| E225 | 7.00 | 659.5 | 0 |
| E226 | 6.92 | 711 | 1 |
| E227 | 6.34 | 653.5 | 4 |
| E228 | 6.69 | 489 | |
| E229 | 6.87 | 680 | 4 |
| E230 | 6.85 | 417 | |
| E231 | 7.24 | 606.5 | |
| E232 | 6.06 | 289 | |
| E233 | ~7.53 | | |
| E234 | 7.21 | 459 | |
| E235 | 7.54 | 419 | |
| E236 | 6.92 | 391 | |
| E237 | 6.39 | 522 | |
| E238 | 6.24 | 382 | |
| E239 | 6.90 | 372 | |
| E240 | 6.31 | 628 | |
| E241 | 6.86 | 653 | |
| E242 | 7.02 | 675.5 | |
| E243 | 6.69 | 802 | |
| E244 | 7.50 | 701 | |
| E245 | 6.40 | 614 | |
| E246 | 6.56 | 494 | |
| E247 | 6.67 | 663 | |
| E248 | 6.97 | 421 | |
| E249 | 6.95 | 418 | 4 |
| E250 | 6.98 | 545.5 | |
| E251 | 6.58 | 658 | |
| E252 | 6.71 | 930 | |
| E253 | 7.04 | 950 | |
| E254 | 7.12 | 662 | |
| E264 | ~7.54 | | |
| E265 | 7.43 | 616.5 | |
| E275 | 5.98 | 1704 | 2 |
| E277 | 5.20 | 2237 | |

E. COMPOSITION EXAMPLES

"Active ingredient" as used throughout these examples relates to a final compound of formula (I), the pharmaceutically acceptable salts thereof, the solvates and the stereochemically isomeric forms thereof.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:
1. A compound according to formula (I)

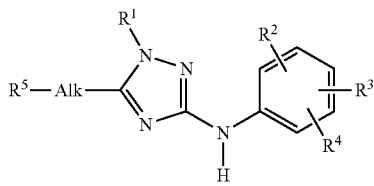

or a stereoisomeric form thereof, wherein
$R^1$ is 2,6-dimethyl-4-pyridinyl;
$R^2$ is hydrogen, halo, $C_{1-3}$alkyl, $C_{1-3}$alkyloxy or trifluoromethoxy;
$R^3$ is hydrogen, halo, or trifluoromethyl;
$R^4$ is hydrogen, or halo;
Alk is straight or branched $C_{1-6}$alkanediyl or $C_{2-6}$alkenediyl;
$R^5$ is hydrogen, hydroxy, $C_{1-3}$alkyloxy, halo, $R^6R^7N-C(=O)-$ or $R^8-O-C(=O)-$;
$R^6$ is $C_{1-3}$alkyl, $C_{3-6}$cycloalkyl or $(C_{3-6}$cycloalkyl)$C_{1-3}$alkyl;
$R^7$ is hydrogen or $C_{1-3}$alkyl; or
$R^8$ is hydrogen or $C_{1-4}$alkyl;
or a pharmaceutically acceptable addition salt thereof.

2. The compound according to formula (I) according to claim 1, wherein
$R^2$ is hydrogen, halo, methyl, methoxy or trifluoromethoxy;
$R^3$ is hydrogen, halo, or trifluoromethyl;
$R^4$ is hydrogen, or halo;
Alk is straight or branched $C_{1-6}$alkanediyl;
$R^5$ is hydroxyl or $R^6R^7N-C(=O)-$;
$R^6$ is methyl, ethyl, cyclopropyl, cyclobutyl or (cyclopropyl)methyl;
$R^7$ is hydrogen or methyl; or a pharmaceutically acceptable addition salt thereof.

3. A compound according to claim 1 selected from
(alphaS)-1-(2,6-dimethyl-4-pyridinyl)-alpha-ethyl-3-[(2,3,4-trifluorophenyl)amino]-1H-1,2,4-triazole-5-ethanol;
(alphaS)-1-(2,6-dimethyl-4-pyridinyl)-alpha-methyl-3-[(2,3,4-trifluorophenyl)amino]-1H-1,2,4-triazole-5-ethanol;
3-[(3,4-difluorophenyl)amino]-1-(2,6-dimethyl-4-pyridinyl)-N-ethyl-1H-1,2,4-triazole-5-acetamide;
N-cyclopropyl-1-(2,6-dimethyl-4-pyridinyl)-3-[[3-(trifluoromethoxy)phenyl]amino]-1H-1,2,4-triazole-5-acetamide;
3-[(3-chloro-2-fluorophenyl)amino]-1-(2,6-dimethyl-4-pyridinyl)-N-ethyl-1H-1,2,4-triazole-5-acetamide;
(alphaS)-1-(2,6-dimethyl-4-pyridinyl)-alpha-ethyl-3-[(3,4,5-trifluorophenyl)amino]-1H-1,2,4-triazole-5-ethanol;
(alphaS)-1-(2,6-dimethyl-4-pyridinyl)-alpha-ethyl-3-[(3-fluoro-5-methoxyphenyl)amino]-1H-1,2,4-triazole-5-ethanol;
(alphaS)-3-[(3-chloro-5-methoxyphenyl)amino]-1-(2,6-dimethyl-4-pyridinyl)-alpha-ethyl-1H-1,2,4-triazole-5-ethanol;
3-[(3,4-difluorophenyl)amino]-1-(2,6-dimethyl-4-pyridinyl)-N,N-dimethyl-1H-1,2,4-triazole-5-propanamide;
or an acid addition salts therof.

4. A pharmaceutical composition comprising a pharmaceutically acceptable carrier and as active ingredient a therapeutically effective amount of a compound as claimed in claim 1.

* * * * *